(12) United States Patent
Holmquist et al.

(10) Patent No.: US 12,025,619 B2
(45) Date of Patent: Jul. 2, 2024

(54) METHODS AND SYSTEMS FOR DETECTING PROSTAGLANDINS BY LC-MS/MS

(71) Applicant: Laboratory Corporation of America Holdings, Burlington, NC (US)

(72) Inventors: Brett Holmquist, Thousand Oaks, CA (US); Mary Katherine Morr Kelemen, Thousand Oaks, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 274 days.

(21) Appl. No.: 17/472,136

(22) Filed: Sep. 10, 2021

(65) Prior Publication Data

US 2022/0082570 A1 Mar. 17, 2022

Related U.S. Application Data

(60) Provisional application No. 63/076,544, filed on Sep. 10, 2020.

(51) Int. Cl.
*G01N 30/06* (2006.01)
*G01N 30/72* (2006.01)
*G01N 33/68* (2006.01)
*G01N 30/88* (2006.01)

(52) U.S. Cl.
CPC ......... *G01N 33/6848* (2013.01); *G01N 30/06* (2013.01); *G01N 30/7233* (2013.01); *G01N 2030/8818* (2013.01)

(58) Field of Classification Search
CPC ........... G01N 33/6848; G01N 30/7233; G01N 2030/8818
USPC ................................ 250/281, 282, 283, 288
See application file for complete search history.

(56) References Cited

U.S. PATENT DOCUMENTS

| | | | |
|---|---|---|---|
| 5,772,874 A | 6/1998 | Quinn et al. | |
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 2003/0157084 A1* | 8/2003 | Jakobsson | A61P 13/00 424/94.4 |

OTHER PUBLICATIONS

Fu, J. et al., "Metabolomics Profiling of the Free and Total Oxidised Lipids in Urine by LC-MS/MS: Application in Patients with Rheumatoid Arthritis," Anal. Bioanal. Chem. 408(23):6307-6319 (2016).

(Continued)

*Primary Examiner* — Nicole M Ippolito
(74) *Attorney, Agent, or Firm* — Kilpatrick Townsend & Stockton LLP

(57) ABSTRACT

Disclosed are methods, systems, and computer program products for using liquid chromatography/tandem mass spectrometry (LC-MS/MS) for the analysis of endogenous biomarkers, such as $PGD_2$, in a biological sample. More specifically, the methods, systems, and computer program products are described for detecting and quantifying the amount of an $PGD_2$ in a sample. The quantitative analysis may be helpful in making clinical diagnoses.

21 Claims, 5 Drawing Sheets

(56) References Cited

OTHER PUBLICATIONS

Miller, T. et al., "A Rapid UPLC-MS/MS Assay for Eicosanoids in Human Plasma: Application to Evaluate Niacin Responsivity," Prostaglandins Leukot. Essent. Fatty Acids 136:153-159 (2017).

Pier, B. et al., "Comprehensive Profiling of Prostaglandins in Human Ovarian Follicular Fluid Using Mass Spectrometry," Prostaglandins and Other Lipid Mediators 134:7-15 (2018).

Rago, B. and Fu, C., "Development of a High-Throughput Ultra Performance Liquid Chromatography-Mass Spectrometry Assay to Profile 18 Eicosanoids as Exploratory Biomarkers for Atherosclerotic Diseases," J. Chromatog. B 936:25-32 (2013).

Song, Y. et al., "An Integrated Platform for Directly Widely-Targeted Quantitative Analysis of Feces Part I: Platform Configuration and Method Validation," J. Chromatog. A 1454:58-66 (2016).

PCT/US2021/049896, International Search Report and Written Opinion, dated Dec. 20, 2021, 16 pages.

Giles, H., and Leff, P., "The biology and pharmacology of $PGD_2$," Prostaglandins 35(2), 277-300 (1988).

Hayaishi, O., "Sleep-wake regulation by prostaglandins $D_2$ and $E_2$," J. Biol. Chem. 263(29), 14593-14596 (1988).

Kikuchi, Y. et al., "Preclinical studies of antitumor prostaglandins by using human ovarian cancer cells," Cancer Metastasis Rev. 13(3-4), 309-315 (1994).

Onoe, H., et al., "Prostaglandin $D_2$, a cerebral sleep-inducing substance in monkeys.," Proc. Natl. Acad. Sci. U.S.A. 85(11), 4082-4086 (1988).

Roberts, L.J., II, and Sweetman, B.J., "Metabolic fate of endogenously synthesized prostaglandin $D_2$ in a human female with mastocytosis," Prostaglandins 30(3), 383-400 (1985).

Yost, R. and Enke, C., in Ch. 8 of Tandem Mass Spectrometry, Ed. McLafferty, pub. John Wiley and Sons (1983).

Zimmer, D. et al., "Comparison of turbulent-flow chromatography with automated solid-phase extraction in 96-well plates and liquid-liquid extraction used as plasma sample preparation techniques for liquid chromatography-tandem mass spectrometry," J. Chromatogr. A, 854:23-35 (1999).

* cited by examiner

METHODS AND SYSTEMS FOR DETECTING PROSTAGLANDINS BY LC-MS/MS

RELATED APPLICATIONS

This application claims priority to U.S. provisional patent application No. 63/076,544 filed on Sep. 10, 2020. The disclosure of U.S. provisional patent application No. 63/076,544, is incorporated by reference in its entirety herein.

FIELD OF THE INVENTION

The presently disclosed subject matter relates to methods and systems for the analysis of the prostaglandins such as prostaglandin $D_2$ ($PGD_2$). In certain embodiments, the measurement of $PGD_2$ may be used for clinical diagnosis.

BACKGROUND

Prostaglandins are fatty acids derived from arachidonic acid metabolism. One such prostaglandin, prostaglandin $D_2$ ($PGD_2$), is derived mainly from prostaglandin H2. The activity of $PDG_2$ is highest in the brain, spinal cord, intestines, and stomach, and $PGD_2$ is the major prostaglandin produced by uterine tissue. $PGD_2$ is involved in a variety of physiological functions, including regulation of body temperature, hormone release, modulation of pain response, and sleep-wake cycles. $PGD_2$ is a known bronchoconstrictor, neuromodulator, and anti-antithrombin agent. $PGD_2$ has also been demonstrated to have an anti-metastatic effect on malignant tumor cells. Thus, $PGD_2$ has been demonstrated to play a role in both inflammatory and homeostatic functions.

$PGD_2$ a known biomarker of several clinical conditions. For example, $PGD_2$ is a major eicosanoid product of mast cells and is released in large quantities during allergic and asthmatic analaphylaxis (Roberts, L. J., II, and Sweetman, B. J., "Metabolic fate of endogenously synthesized prostaglandin $D_2$ in a human female with mastocytosis," *Prostaglandins* 30(3), 383-400 (1985)). Mastocytosis patients produce excessive amounts of $PGD_2$, which causes vasodilation, flushing, hypotension, and syncopal episodes (Roberts et al., 1985). $PGD_2$ is also produced in the brain via an alternative pathway involving a soluble, secreted PGD-synthase also known as β-trace (Hayaishi, O., "Sleep-wake regulation by prostaglandins $D_2$ and $E_2$," *J. Biol. Chem.* 263(29), 14593-14596 (1988) and Onoe, H., et al., "Prostaglandin $D_2$, a cerebral sleep-inducing substance in monkeys.," *Proc. Natl. Acad. Sci. U.S.A.* 85(11), 4082-4086 (1988)). In the brain, $PGD_2$ produces normal physiological sleep and lowering of body temperature (Hayaishi, 1988 and Onoe et al., 1988). Further pharmacological actions include inhibition of platelet aggregation and relaxation of vascular smooth muscle (Giles, H., and Leff, P., "The biology and pharmacology of $PGD_2$" *Prostaglandins* 35(2), 277-300 (1988)). $PGD_2$ inhibits human ovarian tumor cell proliferation with an $IC_{50}$ of 6.8 µM (Kikuchi, Y. et al., "Preclinical studies of antitumor prostaglandins by using human ovarian cancer cells," *Cancer Metastasis Rev.* 13(3-4), 309-315 (1994)).

Thus, there is a need to develop analytical techniques that can be used for the measurement of prostaglandins such as $PGD_2$.

SUMMARY

Embodiments of the present disclosure comprise compositions, methods, and systems for the detection of prostaglandins. In an embodiment, the prostaglandin is $PGD_2$. The present disclosure may be embodied in a variety of ways.

In certain embodiments, disclosed is a method for determining the presence or amount of at least one biomarker of interest in a sample, the method comprising: providing a sample believed to contain at least one biomarker of interest; chromatographically separating the at least one biomarker of interest from other components in the sample; and analyzing the chromatographically separated at least one biomarker of interest by mass spectrometry to determine the presence or amount of the at least one biomarker of interest in the sample.

In some embodiments, the biomarker of interest is a prostaglandin. In one embodiment, the prostaglandin is $PGD_2$. Or, the biomarker of interest may be other prostaglandins. In some embodiments, the disclosed subject matter provides methods and systems for the quantitative analysis of $PGD_2$. In an embodiment, the methods and systems of the disclosure allow for measurement of $PGD_2$ without the need for derivatization processes.

For example, in one embodiment, disclosed is a method for determining the presence or amount of $PGD_2$ in a sample by tandem mass spectrometry. The method may comprise any one of the steps of: (a) obtaining a sample from a subject; (b) optionally adding a stable isotope labeled $PGD_2$ to the sample as an internal standard; (c) performing HPLC; and (d) measuring the $PGD_2$ (both labeled and unlabeled) by tandem mass spectrometry. In an embodiment, the tandem mass spectrometry may comprise the steps of: (i) generating a precursor ion of the $PGD_2$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$ in the sample. In an embodiment, the step of relating the detected ions to the presence or amount of the $PGD_2$ in the sample is quantitative. In an embodiment, the tandem mass spectrometry is coupled to HPLC. The HPLC step may directly precede the tandem mass spectrometry analysis (i.e., LC-MS/MS). In some embodiments, the HPLC is high turbulence liquid chromatography (HTLC). In some embodiments, solid phase extraction is used to partially purify the $PGD_2$ prior to HPLC. Also in some embodiments, a second stable isotope labeled $PGD_2$ (i.e., a different isotope) is added to the sample as an internal standard after the extraction but prior to the LC-MS/MS. In some embodiments, duplicate sets of charcoal stripped calibrators are analyzed in each batch. The method may alternatively be used to measure other prostaglandins, e.g., $PGI_2$, $PGE_2$ or PGF and subtypes thereof.

Another aspect of the disclosure is a system for performing the methods. In some embodiments, the system comprises: a station or component for providing a test sample suspected of containing $PGD_2$; a station or component for partially purifying the $PGD_2$ from other components in the sample; a station or component for chromatographically separating $PGD_2$ from other components in the sample; and a station or component for analyzing the chromatographically separated $PGD_2$ by mass spectrometry to determine the presence or amount of the $PGD_2$ in the test sample. The system may alternatively be used to measure other prostaglandins, e.g., $PGI_2$, $PGE_2$ or PGF and subtypes thereof.

An additional aspect of the disclosure is a computer program product tangibly embodied in a non-transitory machine-readable storage medium, including instructions configured to cause one or more data processors to perform any of the method steps or to control any of the stations or components of the system. For example, the computer program product may contain instructions to perform actions to measure the presence or amount of $PGD_2$ in a sample comprising at least one of the following steps: (a) obtaining a sample from a subject; (b) optionally adding a stable isotope-labeled $PGD_2$ to the sample as an internal standard; (c) performing solid phase extraction; (d) performing HTLC; and (e) measuring the $PGD_2$ by tandem mass spectrometry.

Certain objects of the disclosure, having been stated hereinabove, will become further evident as the description proceeds when taken in connection with the accompanying figures and examples as described herein below.

BRIEF DESCRIPTION OF THE FIGURES

The present disclosure may be better understood by referring to the following non-limiting figures.

DETAILED DESCRIPTION OF THE INVENTION

Figure 1:
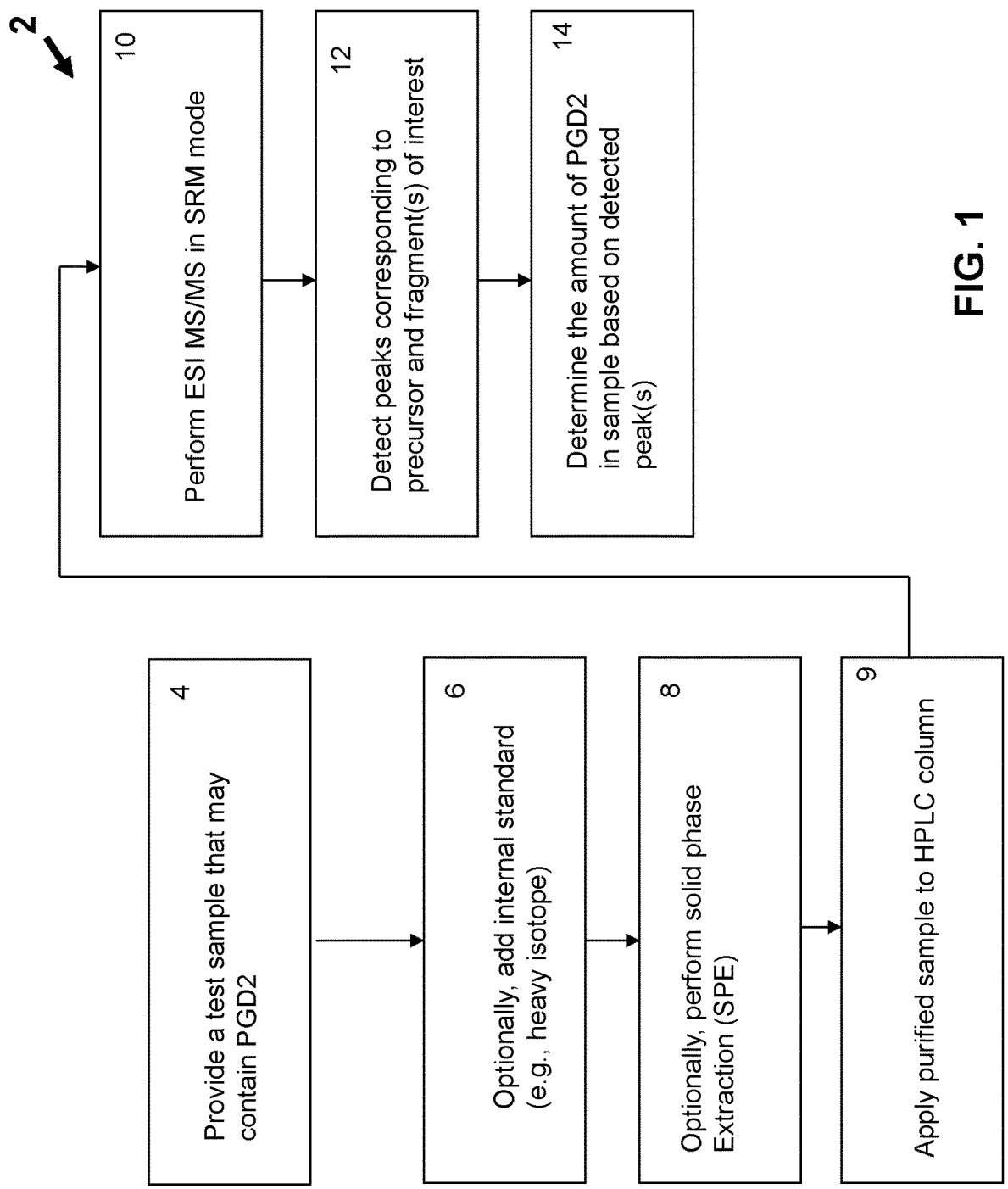
FIG. 1 shows a flow chart of a method for quantitative analysis of $PGD_2$ in accordance with one embodiment of the present disclosure.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Abbreviations

AS=auto sampler
APCI=atmospheric pressure chemical ionization
DB=double blank
ESI=electrospray ionization
HTLC=high turbulence (throughput) liquid chromatography
HPLC=high performance liquid chromatography
IS=internal standard
LC-MS/MS=liquid chromatography with tandem mass spectrometry
LLE=liquid-liquid extraction
LOQ=limits of quantification
LLOQ=lower limit of quantification
SRM—selected reaction monitoring
SST=system suitability test
ULOQ=upper limit of quantification Definitions Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed herein unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "biological sample" encompasses any sample obtained from a biological source. A biological sample can, by way of non-limiting example, include blood, plasma, amniotic fluid, sera, urine, feces, epidermal sample, skin sample, cheek swab, sperm, cultured cells, bone marrow sample and/or chorionic villi. Convenient biological samples may be obtained by, for example, scraping cells from the surface of the buccal cavity. The term biological sample encompasses samples which have been processed to release or otherwise make available a prostaglandin for detection as described herein. The biological sample may be obtained from a stage of life such as a fetus, young adult, adult, and the like. Fixed or frozen tissues also may be used. In some embodiments, the test sample is not a biological sample, but comprises a non-biological sample, e.g., obtained during the manufacture or laboratory analysis of a synthetic analyte, which can be analyzed to determine the composition and/or yield of the manufacturing and/or analysis process.

As used herein, the terms "subject," "individual," and "patient" are used interchangeably. The use of these terms does not imply any kind of relationship to a medical professional, such as a physician. A "subject" may be an animal. Thus, in some embodiments, the biological sample is obtained from a mammalian animal, including, but not limited to a human, a dog, a cat, a horse, a rat, a monkey, and the like. In some embodiments, the biological sample is obtained from a human subject. In some embodiments, the subject is a patient, that is, a living person presenting themselves in a clinical setting for diagnosis, prognosis, or treatment of a disease or condition.

As used herein, the term "chromatography" refers to a process in which a chemical mixture carried by a liquid or gas is separated into components as a result of differential distribution of the chemical entities as they flow around or over a stationary liquid or solid phase.

As used herein, the phrase "liquid chromatography" or "LC" is used to refer to a process for the separation of one or more molecules or analytes in a sample from other analytes in the sample. LC involves the slowing of one or more analytes of a fluid solution as the fluid uniformly moves through a column of a finely divided substance. The slowing results from the distribution of the components of the mixture between one or more stationery phases and the mobile phase. LC includes, for example, reverse phase liquid chromatography (RPLC) and high pressure liquid chromatography (HPLC). In some cases, LC refers to reverse phase LC with a hydrophobic stationary phase in combination with a mobile phase comprised of water and/or water-miscible organic solvents, such as methanol or acetonitrile. In some case, LC may refer to ion exchange chromatography, affinity chromatography, normal phase liquid chromatography, or hydrophilic interaction chromatography.

As used herein, the term "HPLC" or "high performance liquid chromatography" refers to liquid chromatography in which the degree of separation is increased by forcing the mobile phase under pressure through a stationary phase, typically a densely packed column. The chromatographic column typically includes a medium (i.e., a packing material) to facilitate separation of chemical moieties (i.e., fractionation). The medium may include minute particles. The particles can include a bonded surface that interacts with the various chemical moieties to facilitate separation of the chemical moieties such as the biomarker analytes quantified in the experiments herein. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In the method, the sample (or pre-purified sample) may be applied to the column at the inlet port, eluted with a solvent or solvent mixture, and discharged at the outlet port. Different solvent modes may be selected for eluting different analytes of interest. For example, liquid chromatography may be performed using a gradient mode, an isocratic mode, or a polytyptic (i.e. mixed) mode.

As used herein, the term "HTLC" refers to high turbulence liquid chromatography Liquid chromatography may, in certain embodiments, comprise high turbulence liquid chromatography or high throughput liquid chromatography (HTLC). See, e.g., Zimmer et al., J. Chromatogr. A 854:23-35 (1999); see also, U.S. Pat. Nos. 5,968,367; 5,919,368; 5,795,469; and 5,772,874. Traditional HPLC analysis relies on column packings in which laminar flow of the sample through the column is the basis for separation of the analyte of interest from the sample. In such columns, separation is a diffusional process. Turbulent flow, such as that provided by HTLC columns and methods, may enhance the rate of mass transfer, improving the separation characteristics provided.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 3-10 μm. Or, for HTLC the analytical column may comprise particles having an average diameter of about 25-75 μm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns," which typically are used to separate or extract retained materials from non-retained materials to obtained a "purified" sample for further purification or analysis. In some embodiments, the extraction column is a functionalized silica or polymer-silica hybrid or polymeric particle or monolithic silica stationary phase, such as a Poroshell SBC-18 column.

As used herein the term "capillary electrophoresis" (CE) refers to a process for the separation of one or more molecules or analytes in a sample from other analytes in the sample, based on their ionic mobility in an electrolyte solution while exposed to an electric field. CE includes, for example, capillary zone electrophoresis (CZE).

As used herein, the term "separate" or "purify" or the like are not used necessarily to refer to the removal of all materials other than the analyte of interest from a sample matrix. Instead, in some embodiments, the terms are used to refer to a procedure that enriches the amount of one or more analytes of interest relative to one or more other components present in the sample matrix. In some embodiments, a "separation" or "purification" may be used to remove or decrease the amount of one or more components from a sample that could interfere with the detection of the analyte, for example, by mass spectrometry.

As used herein, the term "mass spectrometry" or "MS" refers to a technique for the identification and/or quantitation of molecules in a sample. MS includes ionizing the molecules in a sample to form charged molecules (ions) in gas phase; separating the charged molecules according to their mass-to-charge (m/z) ratio; and detecting the charged molecules. MS allows for both the qualitative and quantitative detection of molecules in a sample. The molecules may be ionized and detected by any suitable means known to one of skill in the art. As used herein, a "mass spectrometer" is an apparatus that includes a means for ionizing molecules and detecting charged molecules.

In certain embodiments, "tandem mass spectrometry" (MS/MS) is used. Tandem mass spectrometry (MS/MS) is the name given to a group of mass spectrometric methods wherein "parent or precursor" ions generated from a sample are fragmented to yield one or more "fragment, daughter or product" ions, which are subsequently mass analyzed by a second MS procedure. As used herein, parent and precursor ion are used interchangeably. Also, as used herein fragment and product ions are used interchangeably. As used herein, fragment, daughter and product ions are used interchangeably. MS/MS methods are useful for the analysis of complex mixtures, especially biological samples, in part because the selectivity of MS/MS can minimize the need for extensive sample clean-up prior to analysis. In an example of an MS/MS method (i.e., triple quadrupole MS/MS), precursor ions are generated from a sample and passed through a first mass filter (quadrupole 1 or Q1) to select those ions having a particular mass-to-charge ratio. These ions are then fragmented, typically by collisions with neutral gas molecules in the second quadrupole (Q2), to yield product (fragment) ions which are selected in the third quadrupole (Q3), the mass spectrum of which is recorded by an electron multiplier detector. The product ion spectra so produced are indicative of the structure of the precursor ion, and the two stages of mass filtering can eliminate ions from interfering species present in the conventional mass spectrum of a complex mixture.

The term "ionization" and "ionizing" as used herein refers to the process of generating an analyte ion having a net electrical charge equal to one or more electron units. Negative ions are those ions having a net negative charge of one or more electron units, while positive ions are those ions having a net positive charge of one or more electron units.

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g. ammonia) is subjected to electron impact, and analyte ions are formed by the interaction of reagent gas ions and analyte molecules.

The term "field desorption" as used herein refers to methods in which a non-volatile test sample is placed on an ionization surface, and an intense electric field is used to generate analyte ions.

The term "desorption" as used herein refers to the removal of an analyte from a surface and/or the entry of an analyte into a gaseous phase.

The term "matrix-assisted laser desorption ionization," or "MALDI" as used herein refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Upon reaching the end of the tube, the solution may be vaporized (nebulized) into a jet or spray of very small droplets of solution in solvent vapor. This mist of droplet can flow through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to mass spectroscopy methods that are similar to ESI, however, APCI produces ions by ion-molecule reactions that occur within a plasma at atmospheric pressure. The plasma is maintained by an electric discharge between the spray capillary and a counter electrode. Then, ions are typically extracted into a mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" ("APPI") as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant.

The term "inductively coupled plasma" as used herein refers to methods in which a sample is interacted with a partially ionized gas at a sufficiently high temperature to atomize and ionize most elements.

As used herein, the term "isotopically labeled," "stable isotopically labeled" or "stable isotope labeled" or similar such terms encompasses the process or product, respectively, of enriching a molecule with a non-radioactive isotope of a given atom so as to alter the average mass of said atom within a molecule and thereby alter the average mass of said molecule. Generally, this is accomplished by replacing the light isotopes more frequently found in nature and in natural molecules (e.g., carbon-12 or nitrogen-14), with the less common heavy isotopes (e.g., carbon-13 or nitrogen-15).

As used herein, a "quadrupole analyzer" is a type of mass analyzer used in MS. It consists of four circular rods (two pairs) that are set highly parallel to each other. The quadrupole may be in triple quadrupole format as is known in the art. The quadrupole analyzer is the component of the instrument that organizes the charged particles of the sample based on their mass-to-charge ratio. One of skill in the art would understand that use of a quadrupole analyzer can lead to increased specificity of results. One pair of rods is set at a positive electrical potential and the other set of rods is at a negative potential. To be detected, an ion must pass through the center of a trajectory path bordered and parallel to the aligned rods. When the quadrupoles are operated at a given amplitude of direct current and radio frequency voltages, only ions of a given mass-to-charge ratio will resonate and have a stable trajectory to pass through the quadrupole and be detected. As used herein, "positive ion mode" refers to a mode wherein positively charged ions are detected by the mass analyzer, and "negative ion mode" refers to a mode wherein negatively charged ions are detected by the mass analyzer.

As used herein selected reaction monitoring (SRM) refers to the technique of using tandem mass spectrometry to select and measure a particular fragment ion of a selected precursor ion. For "selected ion monitoring" or "SIM," the amplitude of the direct current and the radio frequency voltages are set to observe only a specific mass.

As used herein, the term multiple reaction monitoring (MRM) refers to the technique of using tandem mass spectrometry to select and measure more than one parent/precursor and fragment/product pairs within a given analysis. MRM is the application of SRM to multiple product ions from one or more precursor ions.

The term "centrifugation" refers to a process that involves the application of the centripetal force for the sedimentation of heterogeneous mixtures with a centrifuge. The increase the effective gravitational force on a sample, for example, contained in a tube, to more rapidly and completely cause the precipitate (pellet) to gather on the bottom of the tube. The remaining solution is termed "supernatant."

As used herein, the term "prostaglandin D2" or "$PGD_2$" refers to a prostaglandin that binds to the prostaglandin $D_2$ receptor (PTGDR) ($DP_1$) and the chemo attract an receptor-homologus molecule expressed on TH2 cells (CRTH2) ($DP_2$).

As used herein, the term "accuracy" refers to closeness of the agreement between a test result and the accepted reference value expressed as absolute and/or relative bias.

As used herein, the term "analyte" refers to a compound being measured or detected and/or component represented in the name of a measurable quantity.

As used herein, the term "analytical measurement range" (AMR) refers to the range of analyte values that a method can directly measure on the specimen without any dilution, concentration, or other pretreatment not part of the usual assay process.

As used herein, the term "analytic interferences" refers to an artifactual increase or decrease in apparent concentrations, activity, or intensity of an analyte due to the presence of a substance that reacts specifically or nonspecifically with either the detection reagent or the signal itself.

As used herein, the term "interferences" refers to the influence of the presence of hemolysis, lipemia, and icterus on the measurement procedure's ability to accurately measure an analyte.

As used herein, the term "specificity" refers to the ability of the measurement procedure to discriminate the analyte of interest when presented with substances potentially found within a sample. In an embodiment, it is expressed as a percent (%) cross-reactivity and/or response to substances other than analyte of interest in the absence of the analyte of interest.

As used herein, the term "selectivity" refers to the ability of the measurement procedure to accurately measure the analyte of interest without contribution of the substances potentially found within a sample. In an embodiment, it is expressed as a % cross-reactivity and/or response to substances other than analyte of interest in the presence of the analyte of interest.

As used herein, the term "maximum dilution" or "maximum concentration" or "clinical reportable range" refers to the established laboratory specifications for the maximum dilution and/or concentration that may be performed to obtain a reportable numeric result.

As used herein, the term "Limit of Blank" (LOB) refers to the highest measurement result that is likely to be observed for a blank sample (with a stated probability). LOB is typically expressed as mean plus 1.645×SD (or 2×SD) of blank measurements.

As used herein, the term "Limit of Detection" (LOD) refers to the lowest amount of analyte in a sample that can be detected (with stated probability). LOD is typically expressed as LOB plus 1.645×SD (or 2×SD) of low sample measurements.

As used herein, the term "Lower Limit of Quantitation" (LLOQ) refers to the lowest amount of analyte in a sample that can be quantitatively determined with stated acceptable precision and accuracy.

As used herein, the term "Upper Limit of Quantitation" (ULOQ) refers to the highest amount of analyte in a sample that can be quantitatively determined without dilution.

As used herein, the term "Intra-run Imprecision" refers to the closeness of the agreement between the results of successive measurements of the same measure and carried under the same conditions of measurements (same analytical run).

As used herein, the term "Inter-run Imprecision" refers to the closeness of the agreement between independent test results obtained under stipulated conditions (different analytical runs and/or operators, laboratories, instruments, reagent lots, calibrators, etc.).

As used herein, the term "Reference Interval" refers to an interval that, when applied to the population serviced by the laboratory, correctly includes most of the subjects with characteristics similar to the reference group and excludes the others.

As used herein, the term "biomarker" or "marker" refers to one or more nucleic acids, polypeptides and/or other biomolecules (e.g., $PGD_2$) that can be used to diagnose, or to aid in the diagnosis or prognosis of a disease or syndrome of interest, either alone or in combination with other biomarkers; monitor the progression of a disease or syndrome of interest; and/or monitor the effectiveness of a treatment for a syndrome or a disease of interest.

As used herein, the term "on-line" refers to purification or separation steps that are performed in such a way that the test sample is disposed, e.g., injected, into a system in which the various components of the system are operationally connected and, in some embodiments, in fluid communication with one another.

In contrast to the term "on-line", the term "off-line" refers to a purification, separation, or extraction procedure that is performed separately from previous and/or subsequent purification or separation steps and/or analysis steps. In such off-line procedures, the analytes of interests typically are separated, for example, on an extraction column or by liquid/liquid extraction, from the other components in the sample matrix and then collected for subsequent introduction into another chromatographic or detector system. Off-line procedures typically require manual intervention on the part of the operator.

Methods for the analysis of $PGD_2$ by LC-MS/MS

Embodiments of the present disclosure relate to methods and systems for the measurement of prostaglandins. In an embodiment, the prostaglandin is prostaglandin ($PGD_2$). The present disclosure may be embodied in a variety of ways. The measurement of the prostaglandin, e.g., $PGD_2$, may be used for clinical diagnosis. In an embodiment, the disclosed methods and systems allow for measurement of the prostaglandin, e.g., $PGD_2$, without the need for derivatization processes. In certain embodiments, the biological samples suitable for analysis by the methods and systems of the disclosure can include any sample that can contain the prostaglandin of interest. In an embodiment, $PGD_2$ or other prostaglandin is endogenous to a subject.

In one embodiment, the disclosure comprises a method for determining the presence or amount of $PGD_2$ in a biological sample comprising: providing a biological sample believed to contain $PGD_2$; optionally, chromatographically separating $PGD_2$ from other components in the sample; and analyzing the chromatographically separated $PGD_2$ by tandem mass spectrometry to determine the presence or amount of $PGD_2$ in the biological sample. In some embodiments, the biological sample is obtained from a human or another mammal. In some instances the biological sample is a urine sample. In other instances the biological sample is serum.

In certain embodiments, disclosed is a method for determining the presence or amount of $PGD_2$ in a biological sample by tandem mass spectrometry. The method may comprise any one of the steps of: (a) obtaining a biological sample from a subject; (b) optionally adding a stable isotope-labeled $PGD_2$ to the biological sample as an internal standard; (c) optionally performing solid phase extraction; (d) performing HPLC; and (e) measuring the $PGD_2$ (both labeled and unlabeled) by mass spectrometry. In certain embodiments, the mass spectrometry is tandem mass spectrometry (MS/MS). For example, in one embodiment, the tandem MS/MS spectrometry comprises use of a triple quadrupole tandem mass spectrometer.

In an embodiment, the tandem mass spectrometry may comprise the steps of: (i) generating a precursor ion of $PGD_2$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$ in the sample. In an embodiment, the step of relating the detected ions to the presence or amount of the $PGD_2$ in the sample is quantitative. In certain embodiments, the tandem mass spectrometry uses negative ion mode electrospray ionization (ESI). Also, in certain embodiments, quantification of the analyte of interest (i.e., $PGD_2$) and the optional internal standard is performed in selected reaction monitoring mode (SRM).

In certain embodiments, the tandem mass spectrometry is coupled to HPLC. The HPLC step may directly precede the tandem mass spectrometry analysis (i.e., LC-MS/MS). In some embodiments, the HPLC is high turbulence liquid chromatography (HTLC).

In some embodiments, a solid phase extraction is used to partially purify the $PGD_2$ prior to HPLC. Also in some embodiments, a second stable isotope labeled $PGD_2$ (i.e., a different isotope) is added to the sample as an internal standard after the extraction but prior to the LC-MS/MS. In some embodiments, duplicate sets of charcoal stripped calibrators are analyzed in each batch. The method may alternatively be used to measure other prostaglandins, e.g., $PGI_2$, $PGE_2$ or PGF and subtypes thereof.

In an embodiment, the LC-MS/MS is performed on-line. Thus, as disclosed herein, any one of the steps of the method may be controlled by a computer. In some embodiments, the computer comprises one or more data processors and/or a non-transitory computer readable storage medium containing instructions (e.g. software program). Thus, also disclosed herein is a non-transitory computer readable storage medium containing instructions which, when executed on one or more computers, cause the one or more computers to perform actions comprising at least one of the steps of the methods disclosed herein.

The method may, in certain embodiments, comprise the measurement of multiple m/z precursor-fragment transitions. For example, in certain embodiments, and as explained in more detail herein, a first fragment is selected for quantitation of $PGD_2$, whereas an additional fragment or fragments may be chosen as a qualitative standard(s). In some embodiments, the method further comprises detection of an internal standard (which as described herein may be added prior to the extraction steps and/or prior to the HPLC/HTLC step). In some embodiments, the internal standard is a stable isotope labeled $PGD_2$, such as $PGD_2$-$d_9$ or $PGD_2$-$d_4$ as discussed in more detail herein. Thus, in some embodiments, the internal standard is detected by: (i) generating a precursor ion of $PGD_2$-$d_9$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$-$d_9$ of the internal standard.

For example, for $PGD_2$, the transition of a precursor ion of about 351.3 m/z to a fragment ion of about 233.1 m/z may be measured. For the internal standard $PGD_2$-$d_9$, the transition of a precursor ion of about 360.4 m/z to a fragment ion of about 232.9 m/z may be measured.

The internal standard may be used for qualitative and/or quantitative purposes. For example, using isotope dilution mass spectrometry, a stable isotope-labeled analogue of the analyte is added to the sample as an internal standard is measure concurrently with the analyte by LC-MS/MS. In some embodiments, the methods further comprise dual isotope dilution. In some embodiments the method comprise adding a first stable isotope labeled $PGD_2$ to the sample as an internal standard. In further embodiments, the method comprises adding a second stable isotope labeled $PGD_2$ to the sample as an internal standard. In certain instances, a first isotope is added to the extraction step and a second isotope is assed after the extraction step, but prior to the LC-MS/MS. In some embodiments, the first isotope is $PGD_2$-$d_4$ ([2H4]$PGD_2$) and the second is $PGD_2$-$d_9$ ([2H9]$PGD_2$). In other embodiments, the first isotope is [2H9]$PGD_2$ and the second is [2H4]$PGD_2$. In some embodiments, the precursor ion $PGD_2$-$d_4$ has a mass/charge ratio (m/z) of about 355.4 and the one or more fragment ions for quantitation comprise a fragment ion with a m/z of about 275.300, 237.300, 193.2, or 255.5.

Sample preparation can be used to simplify complex sample matrices, remove components, allow for analytes present at low concentration in samples to be concentrated, as well as facilitate solvent switching. In some embodiments, the methods of the disclosure comprise at least partial purification of $PGD_2$ prior to LC-MS/MS. In some embodiments, the methods may comprise at least one purification step, such as protein precipitation, liquid-liquid extraction (LLE), solid phase extraction (SPE), immunopurification, and any combination thereof. In certain embodiments, the sample is subjected to an extraction column. In some embodiments, the column is a SPE column. In some instances, the extraction and/or mass spectrometry are performed on-line. The partial purification method may also include sample dilution prior to analysis by LC-MS/MS.

The method may also comprise the use of calibration standards. In an embodiment, such standards are run through each of the steps of the method so as to correct for sample loss during any step. In some embodiments, duplicate sets of charcoal stripped calibrators are analyzed in each batch. The back-calculated amount of the individual analyte in the sample may then be determined from calibration curves generated by spiking known amounts of each purified analyte into charcoal stripped urine or serum to generate a final concentration of purified analyte of interest. In an embodiment, the calibration standard are purified $PGD_2$ that is within the range of about 1.0 to 1,000 pg/mL. Or, narrower or larger ranges may be used.

An example of a method (2) of the present disclosure is shown in FIG. 1. Thus, in an embodiment, the method may include a step of providing a sample, for example, a serum or urine sample believed to contain $PGD_2$ (4). In some embodiments, an appropriate internal standard is added to the sample (6). For example, in some embodiments for analyzing $PGD_2$ in biological samples, at least one of $PGD_2$-$D_9$ is added as an internal standard for the measurement of $PGD_2$. Or, other stable labeled isotopes of $PGD_2$ may be used.

In some embodiments, the analyte of interest (i.e., $PGD_2$) is partially purified by solid phase extraction (SPE) (8) of the biological sample prior to HPLC. Additionally and/or alternatively, the sample may be diluted in a solvent that can be used for LC or MS in subsequent purification steps. In an embodiment, the SPE is used to concentrate and partially purify the analyte. For example, the SPE may remove phospholipids and/or fibrinogen from the biological samples. In some embodiments, the SPE is a polymeric SPE sorbent combined with matrix removal. After SPE, the sample can be centrifuged (e.g., 2000 rpm or 1207g) for about 1 minute, the supernatant decanted, and the pelleted sample evaporated to remove residual solvent and then reconstituted in a solvent appropriate for LC or HPLC (e.g., acetonitrile:water).

Still referring to FIG. 1, the method may further include liquid chromatography (9) as a means to separate the analyte of interest from other components in the sample. In an embodiment, two liquid chromatography steps are used. For example, the method may comprise a first extraction column liquid chromatography followed by transfer of the biomarker of interest to a second HPLC analytical column. In other embodiments, only one HPLC step is used. In some embodiments, HTLC is used.

For example, the reconstituted extract may be applied onto a HPLC or HTLC system, wherein the analytes are eluted using an isocratic separation through an extraction column. In certain embodiments, the mobile phase that is used comprises a gradient.

The LC may, in certain embodiments, comprise high turbulence liquid chromatography or high throughput liquid chromatography (HTLC) (sometimes referred to as turbulent flow liquid chromatography (TFLC). In some embodiments, HTLC, alone or in combination with one or more purification methods, may be used to purify the biomarker of interest prior to mass spectrometry. Also, in some embodiments, the use of a HTLC sample preparation method can eliminate the need for other sample preparation methods including SPE. Thus, in some embodiments, the test sample, e.g., a biological fluid, can be disposed, e.g., injected, directly onto a high turbulence liquid chromatography system.

For example, in one embodiment, an Aria TX4 HTLC System (Thermo Scientific MA) consisting of 4-1100 Series Quaternary Pumps, 4-1100 Series Binary Pumps, 8-1100 Series Vacuum Degasser or 8-1200 Series Binary Pumps, 8-1200 Series Vacuum Degasser is used. In this embodiment, the sample is reconstituted in 10% acetonitrile in reagent grade water prior to application to the HTLC column. In an embodiment, the Pump A mobile phase is 0.1% formic acid in water and the Pump B mobile phase is 100% acetonitrile.

The separated analytes are then introduced into a mass spectrometer (MS) system (10). In some embodiments, a tandem MS/MS system is used. In an embodiment, an API 4000, API 5000, or API 5500 (or equivalent) Tandem Mass Spectrometer, Danaher (Toronto, CA) is used. The analyte of interest (i.e., $PGD_2$) may then be quantified based upon the amount of the characteristic transitions measured by tandem MS as detailed herein. In some embodiments, the tandem mass spectrometer comprises a triple quadrupole mass spectrometer.

In mass spectrometry, analytes are ionized to produce gas phase ions suitable for resolution in the mass analyzer. Ionization occurs in the ion source. There are several ion sources known in the art. In some embodiments, the analyte may be ionized by any method known in the art. For example, ionization may be performed using any of the following ion sources: atmospheric pressure chemical ionization (APCI), atmospheric pressure photoionization (APPI), electron impact ionization (EI), electrospray ionization (ESI), matrix assisted laser desorption (MALDI), surface enhanced laser desorption ionization (SELDI), thermospray ionization, inductively coupled plasma (ICP), and fast atom bombardment (FAB). $PGD_2$ may be ionized in positive or negative ion mode. In one embodiment, ESI is used.

After the sample has been ionized, the charged ions may be analyzed to determine mass-to-charge ratios (m/z). For example, quadrupole mass spectrometers, ion trap mass spectrometers, and time-of-flight (TOF) mass spectrometers can be used to produce a mass spectra for an analyte of interest. Ions may be detected using any detection mode generally known in the art, including but not limited to selective ion monitoring (SIM), multiple reaction monitoring (MRM), and selected reaction monitoring (SRM).

In certain embodiments, the mass spectrometer uses a "quadrupole" system. In a "quadrupole" or "quadrupole ion trap" mass spectrometer, ions in an oscillating radio frequency (RF) field experience a force proportional to the direct current (DC) potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

In an embodiment, the methods and systems of the present disclosure use a triple quadrupole MS/MS (see e.g., Yost, Enke in Ch. 8 of Tandem Mass Spectrometry, Ed. McLafferty, pub. John Wiley and Sons, 1983). Triple quadrupole MS/MS instruments typically consist of two quadrupole mass filters separated by a fragmentation means. Quadrupole 1 (Q1) is a mass filter that allows for selection of precursor ions and Q3 allows for selection of product ions based on mass-to-charge ratios. Quadrupole 2 (Q2) is the collision cell where the precursor ions selected in Q1 are fragmented into product ions. While in Q2, precursor ions are collided with neutral molecules such as argon, nitrogen, or helium causing the precursor ions to fragment in process called collision-induced dissociation (CID). The fragments are then accelerated into the third quadrupole (Q3) mass filter, which scans through the mass range and produces a mass spectrum as the fragment ions hit a detector.

In certain embodiments, tandem mass spectrometry is used. See, e.g., U.S. Pat. No. 6,107,623, entitled "Methods and Apparatus for Tandem Mass Spectrometry," which is hereby incorporated by reference in its entirety. The selectivity of the MS technique can be enhanced by using "tandem mass spectrometry," or "MS/MS." MS/MS methods are useful for the analysis of complex mixtures, especially biological samples, in part because the selectivity of MS/MS can minimize the need for extensive sample cleanup prior to analysis.

In one embodiment, the instrument may comprise a quadrupole mass filter operated in the RF only mode as an ion containment or transmission device. In an embodiment, the quadrupole may further comprise a collision gas at a pressure of between 1 and 10 millitorr. Many other types of "hybrid" tandem mass spectrometers are also known, and can be used in the methods and systems of the present disclosure including various combinations of magnetic sector analyzers and quadrupole filters. These hybrid instruments often comprise high resolution magnetic sector analyzers (i.e., analyzers comprising both magnetic and electrostatic sectors arranged in a double-focusing combination) as either or both of the mass filters. Use of high resolution mass filters may be highly effective in reducing chemical noise to very low levels.

The mass spectrometer provides the user with an ion scan displaying the relative ion abundance (peaks) of the ions in the mass spectrum (12). Thus, the mass spectrum can be used to determine the amount of analyte (i.e., $PGD_2$) present in the sample (14). In some instances, the back-calculated amount of each analyte in each sample may be determined by comparison of the sample response or response ratio when employing internal standardization to calibration curves generated by spiking a known amount of purified analyte material into a standard test sample, e.g., charcoal stripped human urine. In one embodiment, calibrators are prepared at known concentrations to generate a response or response ratio when employing internal standardization versus concentration calibration curve. In an embodiment, this determination is performed at least in part by a computer or data analysis system and/or a non-transitory computer readable storage medium containing instructions which, when executed on the one or more data processors, cause the one or more data processors to perform actions to make this determination.

In various embodiments, the method includes a detailed review of raw data, quality control, review and interpretation of patient results followed by release to the laboratory system. For example, in certain embodiments, duplicate calibration curves are used for each batch of samples. In certain embodiments, a total of 25% of standard points may be excluded from the combined curves if the back-calculated concentrations exceed the theoretical concentrations by >20% at the LLOQ or >15% at other concentrations. Or, other cut-offs may be used. In an embodiment, a result may be reported below the lowest, or above the highest remaining standard. In an embodiment, the standard curve correlation coefficient is $(r)>0.98$. Also, in certain embodiments, the method requires that control pools be within acceptable limits as is known in the art. In an embodiment, all chromatographic peak shapes are reviewed for consistency. For example, where peak distortion is observed; a contaminant may be present. In an embodiment, the method includes ensuring that the correct peak is integrated where multiple peaks are observed within the chromatogram by confirming that the retention time of the peak integrated corresponds to calibrators and quality control samples. For example, the method may include review of the internal standard peak area vs. mass spectrum index plot. In an embodiment, internal standard peak areas more than 50% greater than the neighboring peaks may be submitted for repeat analysis and/or internal standard peak areas more than 33% less than the neighboring peaks may be submitted for repeat analysis. Or, other cut-offs may be used. In an embodiment, this review and analysis is done by a computer or data analysis system and/or a non-transitory computer readable storage medium containing instructions, which when executed on the one or more data processors, cause the one or more data processors to perform actions to perform this analysis and/or review.

Systems for the Analysis of $PGD_2$

Also disclosed are systems for determining the presence or amount of a prostaglandin, e.g., $PGD_2$, in a sample. For example, in some embodiments the system may comprise: a station or component for providing a biological sample believed to contain a prostaglandin of interest such as $PGD_2$; optionally a station or stations (or component(s)) for sample extractions (i.e., clean-up or prepurification) and/or chromatographically separating the prostaglandin (e.g., $PGD_2$) from other components in the biological sample; and a station or component for analyzing the chromatographically separated prostaglandin (e.g. $PGD_2$) by mass spectrometry to determine the presence or amount of the prostaglandin (e.g., $PGD_2$) in the biological sample. In an embodiment, the sample is a biological sample obtained from a human or another mammal. For example, the sample may be human serum or urine.

In an embodiment, the mass spectrometry is tandem mass spectrometry (MS/MS). In an embodiment, the mass spectrometry is operated in electrospray ionization (ESI) mode. In an embodiment, quantification of $PGD_2$ is performed in selected reaction monitoring mode (SRM). For example, the station for tandem mass spectrometry may comprise a Sciex API4000, API5000, or API5500 tandem mass spectrometer (or equivalent), Danaher (Toronto, CA).

In one embodiment, the station for chromatographic separation comprises at least one component, e.g., apparatus, to perform liquid chromatography (LC). In one embodiment, the station for liquid chromatography comprises a column for extraction chromatography. Additionally or alternatively, the station for liquid chromatography comprises a column for analytical chromatography. In certain embodiments, the column for extraction chromatography and analytical chromatography comprise a single station or single column. Various columns comprising stationary phases and mobile phases that may be used for extraction or analytical LC are described herein. In some embodiments, the extraction column is a functionalized silica or polymer-silica hybrid or polymeric particle or monolithic silica stationary phase. In some embodiments, a core-shell silica solid support is use. A column used for analytical liquid chromatography may be varied depending on the column that was used for the extraction liquid chromatography step. For example, in certain embodiments, the analytical column comprises particles having an average diameter of about 5 μm. In other embodiments, the analytical column comprises particles having an average diameter of about 2.6 µm. In some embodiments, the analytical column is a functionalized silica or polymer-silica hybrid, or a polymeric particle or monolithic silica stationary phase. Thus, in some embodiments, the stationary phase is C18 with TMS endcapping. For example, in some embodiments the LC column is a Phenomenex Kinetex 2.6 µm C18(2) 100 Å, 150×4.6 mm.

In some embodiments, HPLC is used to purify the $PGD_2$ from other components in the sample that co-purify with the $PGD_2$ after extraction and/or dilution of the sample. Or, in other embodiments, HTLC is used to purify the $PGD_2$ from other components in the sample. For example, in one embodiment, an Aria TX4 HTLC System (Thermo Scientific MA) consisting of 4-1100 Series Quaternary Pumps, 4-1100 Series Binary Pumps, 8-1100 Series Vacuum Degasser or 8-1200 Series Binary Pumps, 8-1200 Series Vacuum Degasser is used.

In an embodiment, the system may further comprise a station or component for partially purifying the $PGD_2$ from other components in the sample as for example by liquid-liquid extraction (LLE) and/or dilution. Or, in some embodiments, solid phase extraction (SPE) may be used. Thus, in certain embodiments, the system may also comprise a station for extracting the $PGD_2$ from the biological sample and/or diluting the sample. The station for partial purification (e.g., SPE) may comprise equipment and reagents for addition of solvents to the sample and removal of waste fractions. In some cases a isotopically-labeled internal standard such as $PGD_2$-$d_9$ (SantaCruz—SC-224218) is used to standardize losses of the biomarker that may occur during the procedures. Thus, the station for SPE may comprise a hood or other safety features required for working with solvents and/or isotopes.

Also, in certain embodiments, at least one of the stations is automated and/or controlled by a computer. For example, as described herein, in certain embodiments, at least some of the steps are automated such that little to no manual intervention is required. For example, as disclosed herein, any one of the stations or components may be controlled by a data processor or a computer. Also disclosed herein is a data processor and/or a non-transitory computer readable storage medium containing instructions (i.e., software) which, when executed on the one or more data processors or computers, cause the one or more data processors or computers to perform actions for at least one of the stations of the system.

Figure 2:
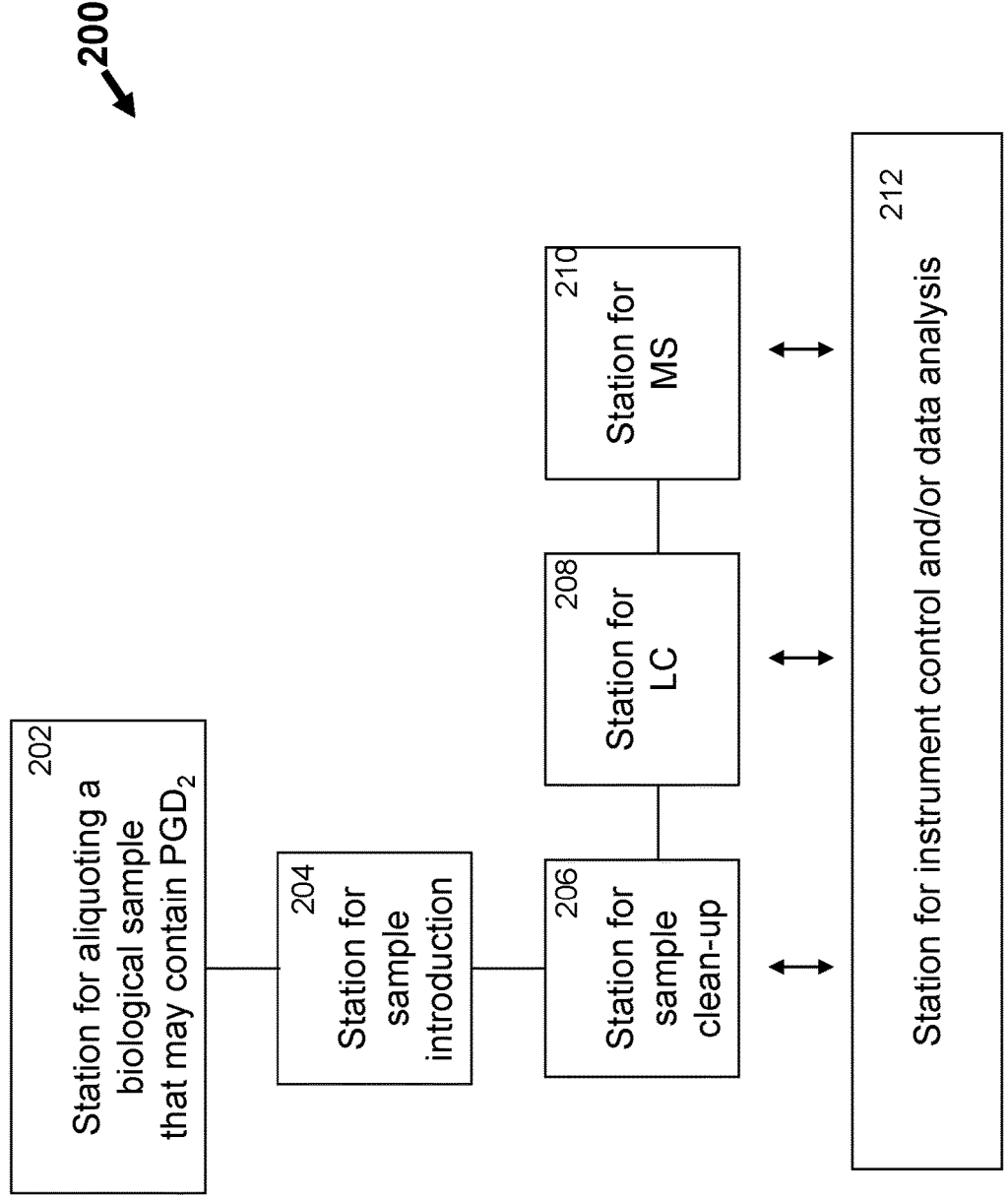
FIG. 2 shows a system for quantitative analysis of $PGD_2$ in accordance with one embodiment of the present disclosure.

FIG. 2 shows an embodiment of a system (200) of the present invention. As shown in FIG. 2, the system may comprise a station for aliquoting a sample (202) that may comprise a biomarker (e.g., $PGD_2$) of interest into sampling containers. In one embodiment, the sample is aliquoted into a container or containers to facilitate SPE or sample dilution. The station for aliquoting may comprise receptacles to discard the portion of the sample that is not used in the analysis. The station for aliquoting a sample (202) may further comprise a station for adding an internal standard to the sample. In an embodiment, the internal standard comprises the biomarker (e.g., $PGD_2$) of interest labeled with a non-natural isotope. Thus, the station for adding an internal standard may comprise safety features to facilitate adding an isotopically labeled internal standard solutions to the sample. The system may also, in some embodiments, comprise a station (206) for sample clean-up (i.e., purification of the analyte away from other components in the sample and/or dilution of the sample). In some embodiments, the station for sample clean-up comprises a station for SPE, liquid-liquid extraction, protein precipitation, dilution of the samples or other types of purification procedures.

The system may also comprise a station for liquid chromatography (LC) of the sample (108). As described herein, in an embodiment, the station for liquid chromatography may comprise an extraction liquid chromatography column, or the station may comprise HPLC and no extraction column. Or, as discussed in more detail below, other types of liquid chromatography, such as high turbulence liquid chromatography (HTLC) may be used. For example, in one embodiment, an Aria TX4 HTLC System (Thermo Scientific MA) consisting of 4-1100 Series Quaternary Pumps, 4-1100 Series Binary Pumps, 8-1100 Series Vacuum Degasser or 8-1200 Series Binary Pumps, 8-1200 Series Vacuum Degasser is used. In this embodiment, the sample may be reconstituted in 10% acetonitrile in reagent grade water prior to application to the HTLC column. In an embodiment, the Pump A mobile phase is acetonitrile:methanol:water (5:5:90) and the Pump B mobile phase is acetonitrile:methanol:water (45:45:10).

Thus, the station for liquid chromatography may comprise a column comprising the stationary phase, as well as containers or receptacles comprising solvents that are used as the mobile phase. The station may comprise the appropriate lines and valves to adjust the amounts of individual solvents being applied to the column or columns. Also, the station may comprise a means to remove and discard those fractions from the LC that do not comprise the biomarker of interest. In an embodiment, the fractions that do not contain the biomarker of interest are continuously removed from the column and sent to a waste receptacle for decontamination and to be discarded.

Also, the system may comprise a station for characterization and quantification of the $PGD_2$ biomarker (FIG. 2). In one embodiment, the system may comprise a station for mass spectrometry (MS) of the $PGD_2$ biomarker(s) (210). In an embodiment, the station for mass spectrometry comprises a station for tandem mass spectrometry (MS/MS). The system may further comprise a station (212) for instrument control and data analysis, wherein the station interacts with the station (206) for sample clean-up, the station (208) for LC, and/or the station (210) for MS. Also, the station for instrument control and data analysis may further comprise a stations for characterization and quantification (212). The station (212) for data analysis may be part of the MS/MS station or a separate station and may comprise a computer and/or software for analysis of the MS/MS results. In an embodiment, the station (212) for instrument control and/or data analysis comprises a computer or data processor and/or a non-transitory computer readable storage medium (e.g., software) containing instructions, which when executed on the one or more data processors, cause the one or more data processors to perform the data analysis. In an embodiment, the analysis comprises both identification and quantification of the biomarker of interest (e.g., $PGD_2$). In an embodiment, the analysis system comprises a computer (300).

Figure 3:
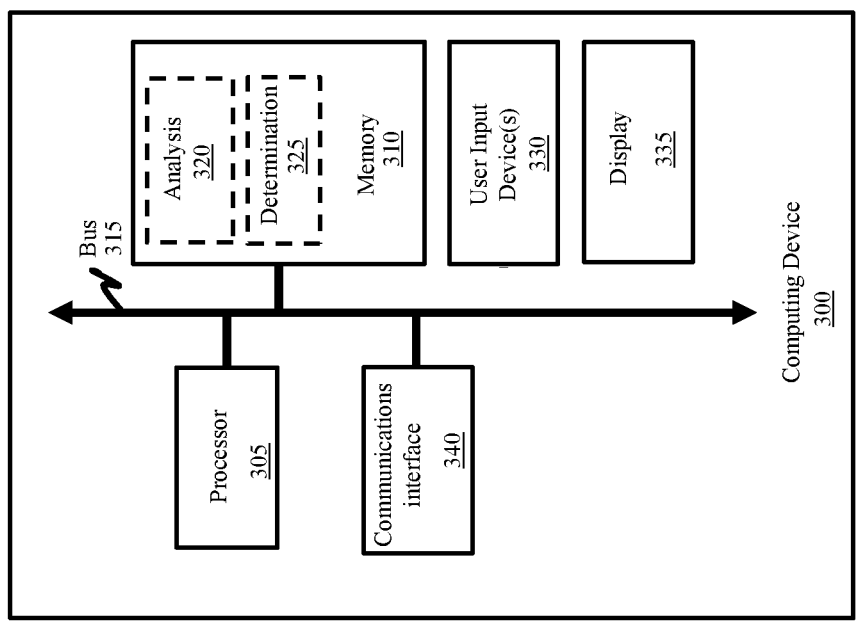
FIG. 3 shows an exemplary computing device in accordance with various embodiments of the disclosure.

FIG. 3 shows a block diagram of a computer 300 used for detection and/or quantification of a biomarker of interest (e.g., $PGD_2$). As illustrated in FIG. 3, modules, engines, or components (e.g., program, code, or instructions) executable by one or more processors may be used to implement the various subsystems of an analyzer system according to various embodiments. The modules, engines, or components may be stored on a non-transitory computer medium. As needed, one or more of the modules, engines, or components may be loaded into system memory (e.g., RAM) and executed by one or more processors of the analyzer system. In the example depicted in FIG. 3, modules, engines, or components are shown for implementing the methods or running any of the systems of the disclosure.

Thus, FIG. 3 illustrates an example computing device 300 suitable for use with systems and the methods according to this disclosure. The example computing device 300 includes a processor 305 which is in communication with the memory 310 and other components of the computing device 300 using one or more communications buses 315. The processor 305 is configured to execute processor-executable instructions stored in the memory 310 to perform one or more methods or operate one or more stations for detecting biomarker of interest (e.g., $PGD_2$) according to different examples. In this example, the memory 310 may store processor-executable instructions 325 that can analyze 320 results for sample as discussed herein.

The computing device 300 in this example may also include one or more user input devices 330, such as a keyboard, mouse, touchscreen, microphone, etc., to accept user input. The computing device 300 may also include a display 335 to provide visual output to a user such as a user interface. The computing device 300 may also include a communications interface 340. In some examples, the communications interface 340 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

In some embodiments, one or more of the purification or separation steps can be performed "on-line." The on-line system may comprise an autosampler for removing aliquots of the sample from one container and transferring such aliquots into another container. For example, an autosampler may be used to transfer the sample after extraction onto an LC extraction column. The on-line system may comprise one or more injection ports for injecting the fractions isolated from the LC extraction columns onto the LC analytical column and/or one or more injection ports for injecting the LC purified sample into the MS system. Thus, the on-line system may comprise one or more columns, including but not limited to an HTLC column. In such "on-line" systems, the test sample and/or analytes of interest can be passed from one component of the system to another without exiting the system, e.g., without having to be collected and then disposed into another component of the system.

In some embodiments, the on-line purification or separation method is highly automated. In such embodiments, the steps can be performed without the need for operator intervention once the process is set-up and initiated. For example, in one embodiment, the system, or portions of the system (e.g., HTLC, MS/MS and data analysis) may be controlled by a computer. Thus, in certain embodiments, the system may comprise software for controlling the various components of the system, including pumps, valves, autosamplers, and the like. Such software can be used to optimize the extraction process through the precise timing of sample and solute additions and flow rate.

Figure 4:
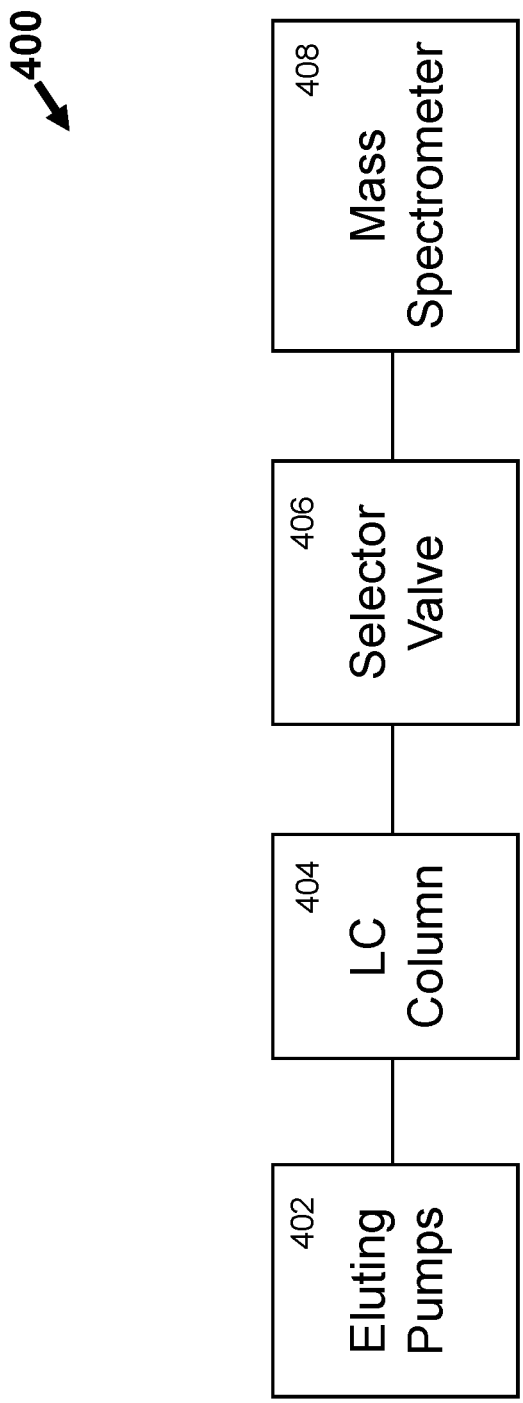
FIG. 4 shows a diagram for an on-line LC-MS/MS system in accordance with one embodiment of the present disclosure.

For example, FIG. 4 shows an embodiment, of an on-line plumbing diagram in which eluting pumps (402) are coupled to an LC column (404), which is coupled to a selector valve (406), which is coupled to the mass spectrometer (408).

Although some or all of the steps in the method and the stations or components comprising the system may be on-line, in certain embodiments, some or all of the steps may be performed "off-line."

Thus, the disclosure provides methods and systems for applying liquid chromatography and mass spectrometry as a means to separate a biomarker analyte of interest, such as $PGD_2$, from other components that may be present in a sample. The methods and systems may comprise an off-line liquid-liquid extraction and/or sample dilution step as a means to partially purify the sample prior to HTLC and tandem mass spectrometry. The methods and systems may be used for clinical diagnosis.

The systems and methods may, in certain embodiments, provide for a multiplexed assay. For example, certain embodiments of the present invention may comprise a multiplexed liquid chromatography tandem mass spectrometry (LC-MS/MS) or two-dimensional or tandem liquid chromatography-tandem mass spectrometry (LC)-LC-MS/MS) methods for the quantitative analysis of $PGD_2$ is biological samples.

Embodiments may provide certain advantages. In an embodiment, an accurate, precise, simple and fast HPLC-MS/MS isotope dilution commercially available method has been developed to allow quantitative measurements of $PGD_2$ in urine or serum. Reference intervals can be developed for adult men, adult women, and pediatric subjects. Also, in an embodiment, good correlation with other assay systems will allow result interpretation for clinical conditions, including mastocytosis using published data.

In certain embodiments, the methods and systems may provide greater sensitivity than the sensitivities previously attainable for $PGD_2$. Also, embodiments of the methods and systems may provide for rapid throughput that has previously not been attainable for many of the analytes being measured.

As another advantage, the specificity and sensitivity provided by the disclosed methods and systems may allow for the analysis of analytes from a variety of materials. For example, the disclosed methods and systems can be applied to the quantification of analytes of interest in complex sample matrices, including, but not limited to urine or serum. Also, using the disclosed methods and systems allows for measurement of $PGD_2$ without derivatization and at levels as low as 1 pg/mL. Thus, the methods and systems are suitable for clinical applications and/or clinical trials.

As additional potential advantages, in certain embodiments, the disclosed systems and methods provide approaches for addressing isobaric interferences, varied sample content, including hemolysed and lipemic samples, while attaining low pg/mL limits of quantification (LLOQ) of the target analytes. Accordingly, embodiments of the disclosed methods and systems may provide for the quantitative, sensitive, and specific detection of clinical biomarkers used in clinical diagnosis. For example, in some embodiments the lower limit of detection using a sample aliquot of 400 μL is at least 10 pg/mL, 5 pg/mL, 2 pg/mL, or 1 pg/mL. In certain embodiments, the lower limit of detection using a sample aliquot of 500 μL is at least 10 pg/mL, 5 pg/mL, 2 pg/mL, or 1 pg/mL.

Embodiments of the methods and systems of the present disclosure may provide for rapid throughput that has previously not been attainable for many of the analytes being measured. For example, using the methods and systems of the present disclosure, multiple samples may be analyzed for PGD$_2$ using 96 well plates and a multiplex system of four LC-MS/MS systems, significantly increasing the throughput.

EXAMPLES

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter.

Example 1. Measurement of PGD$_2$ in Urine by SPE-LC-MS/MS

Specimens. All studies were performed using urine samples. Acceptable sample volumes are shown in TABLE 1. The minimum sample volume was determined to be 1 mL of urine.

TABLE 1

| Specimen Collection | |
|---|---|
| Adult: | 5 mL urine is acceptable |
| Pediatric: | 2.5 mL urine is acceptable |
| Minimum: | 1 mL urine is acceptable |

Urine samples were collected into plastic containers. Specimens were stored according to the following conditions:

Short Term Storage
  Urine Frozen (≤−10° C. and ≤−55° C.): 8 days
  Urine Refrigerated (2-8° C.): 3 days
  Urine Room Temperature (15-30° C.): 3 days
  Urine Freeze/Thaw (≤−10° C.): 6 Cycles
Long Term Storage
  Urine Frozen (≤−10° C.): Stability testing in process
Shipping Conditions:
  Urine Frozen (≤−10° C.):—on dry ice PGD$_2$ was stable for at least 3 days at 4° C. and at room temperature and 8 days frozen (≤−10° C. or ≤−55° C.). PGD$_2$ was stable for at least 6 freeze-thaw cycles (≤−10° C. or ≤−55° C.).

Assay parameters. The assay was conducted according to the parameters provided in TABLE 2.

TABLE 2

| Assay parameters | | | |
|---|---|---|---|
| Parameter | Value or Criteria | | |
| Reportable Range | AMR (LLOQ-ULOQ) | Maximum Dilution/ Concentration | Units of Measure |
| Prostaglandin D$_2$ | 1-1000 pg/mL | X10/10000 pg/mL | pg/mL |
| Max Dilution | Reduced volume of 40 µL is allowable. | | |
| Preferred Specimen | Urine | | |

Acceptance criteria. For acceptance, no more than 25% of all standard curve values may be deleted. Previous standard curve data may be used to identify standard points to delete. Standard curve regression was based upon individual replicates, and each replicate was considered a point for acceptance rules.

Controls. Three levels of control pools were prepared from human urine pools, spiked or diluted is required to meet target values. For very low quality control (QC) levels that were not feasible to use human urine matrix, charcoal stripped human urine was used as a diluent for the human urine pools.

A control result was defined as the mean of two duplicates with coefficient variation (CV)<20%. The mean of both duplicates was used in determining acceptance.

Dilutions. Sample dilutions were made with standard matrix, with a maximum allowable dilution factor of ×10. The recommended dilution scheme is shown in TABLE 3.

TABLE 3

| Recommended Dilution Scheme | | | |
|---|---|---|---|
| Dilution Level | Sample | Volume of Sample (µL) | Volume of Diluent, S0 (µL) |
| X10 | Neat Human Urine | 20 | 180 |

Sample preparation. Frozen standards, controls, and samples were thawed and vortexed three times. An aliquot (e.g., 400 µL) of the standard, control, or sample (neat or diluted) were pipetted into 12×75 mm borosilicate glass tubes. When sufficient volume was unavailable, samples were added in lower amounts. The acceptable volume for reduced volume analysis was determined to be at least 40 µL. 100 µL of internal standard was pipetted into each tube, except for four tubes that were left empty as double blanks. The glass tubes were covered with parafilm and vortexed 10 times. 1.2 mL of 1% Formic Acid in water was added to all tubes, including the double blanks. The glass tubes were covered with parafilm and vortexed 10 times. The appropriate dilution factor was applied to reduce volume analyses.

SPE plate processing. A Strata X Pro 96-well plate (Phenomenex Catalog #8E-5536-TGA, or equivalent) was placed on top of a waste collection plate. 1 mL of methanol was added to each well and the wells were drained by gravity without the use of positive pressure. 1 mL of 5% methanol in water was then added to each of the wells drained by gravity without the use of positive pressure. The entire volume of diluted standards, controls, and samples were transferred to the corresponding wells of the plate. The wells were first drained by gravity and then positive pressure was applied on low setting. 1 mL of 5% methanol in water was added to each of the wells of the 96-well plate and the wells were drained by gravity and then positive pressure was applied on low setting. 1 mL of 20% methanol in water with 2% ammonium hydroxide was then added to each of the wells and the wells drained by gravity and then positive pressure was applied on low setting. Next, 1 mL of 5% methanol in water was added to each of the wells and after the wells were drained by gravity, positive pressure was applied on low setting. Next, 1 mL of 30% methanol in water with 2% formic acid was added to each of the wells and after the wells were drained by gravity, positive pressure was applied on low setting. 1 mL of 5% methanol in water was then added to each of the wells and the wells drained by gravity followed by positive pressure applied on low setting. Next, 1 mL of 40% methanol in water was added to each of the wells and the wells were drained by gravity and then positive pressure was applied on low setting. The positive pressure setting was switched to high for 1 minute. Next, the plate was placed on top of a new 1.2 mL 96-well collection plate and 300 µL of 2% acetic acid in chloroform was added to each of the wells of the sample/standard plate. The wells were drained by gravity and then positive pressure was applied on low setting. Again, 300 µL of 2% acetic acid in chloroform was added to each of the wells. The wells were again drained by gravity, and then positive pressure was applied on low setting. The 1.2 mL 96-well plate with collected samples was then placed into a TurboVap 96 Concentration Workstation (Biotage Life Sciences) for approximately 30 mins at 40° C. until samples were dry. Then, 120 µL of $PGD_2$ reconstitution solution (3.33 ng/mL $PGD_2$-$d_4$ internal standard in 1:3 methanol:10 mM ammonium acetate) was added to all wells, the plate was sealed, and mixed four times for 30 seconds (for a total of 2 minutes). The 96-well plate was then positioned in the LC-MS/MS Autosampler.

HTLC-MS/MS Procedure. For HTLC purification of $PGD_2$, a Phenomenex Kinetex 2.6 µm C18(2) 100 Å, 150×4.6 mm column was used. All LC system reagents were filled and LC pumps were primed to remove any bubbles from mobile phase lines or to remove mobile phase from previous assays. The mass spectrometer was then equilibrated for 1 minute. The Aria system (Aria OS Version 1.4 or greater, Cohesive Technologies (MA, USA)) was started. Aria TX4 HTLC System, Cohesive Technologies, (MA, USA) consisting of 4 each: 1100 Series Quaternary Pump, 1100 Series Binary Pump, 1100 Series Vacuum Degasser, or 8 Series 1200 Binary Pump and 4 Series 1200 Vacuum Degasser were started and primed at 5 mL per minute for 5 minutes for each solvent to be used. Test injections were performed using $UPGD_2$ system suitability test (SST). The loading pump was run using a gradient starting with 60% mobile phase A (0.1% formic acid in water) and 40% mobile phase B (100% acetonitrile) at a flow rate of 0.8 mL/min. The eluting pump was run with 100% mobile phase A and 0% mobile phase B at a flow rate of 0.00 mL/min.

Figure 5:
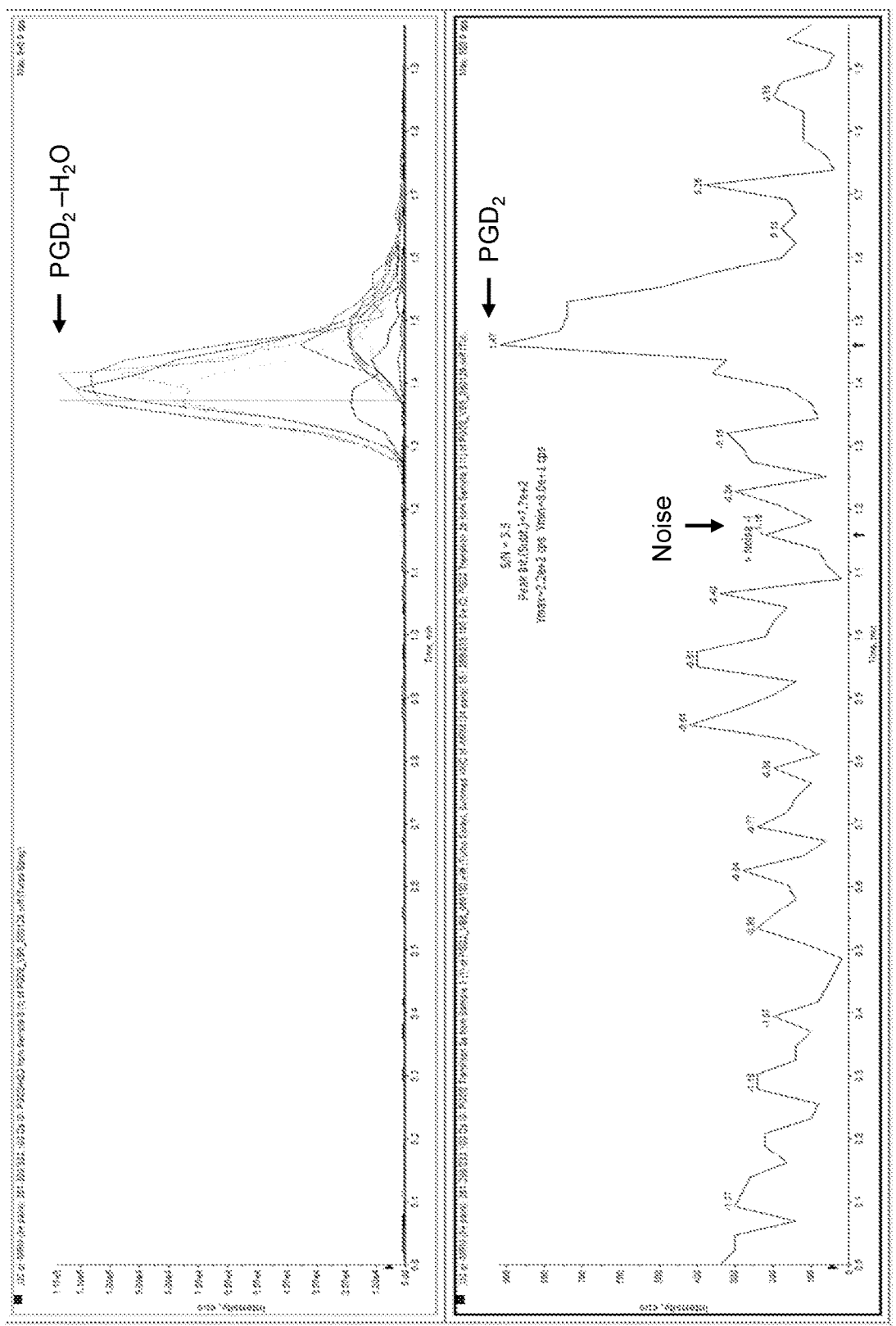
FIG. 5 depicts a plot of a $PGD_2$ system suitability testing (SST) chromatogram in accordance with an embodiments of the present disclosure.

For MS/MS, an AB SCIEX API5000 triple quadrupole mass spectrometer, operating in negative ion electrospray ionization (ESI) mode (Turboionspray) was used for detection. Quantification of analyte and internal standard was performed in selected reaction monitoring mode (SRM) with the use of ion summing. For $PGD_2$ the 351.3→233.1 transition was monitored. For the internal standard ($PGD_2$-$d_9$), the 360.4→232.9 transition was monitored. A resulting MS/MS scan of the $PGD_2$ system suitability test (SST) is shown in FIG. 5. For FIG. 5, $PGD_2$-$H_2O$ peaks of 351.300 and 333.100 and $PGD_2$ SST peaks of 351.298 and 233.100 were analyzed. The signal:noise (S/N) ratio was 5.5. The peak intensity was 7.7e+2 counts per second (cps) with a Ymax of 2.2e+2 cps and Ymin of 8.0e+1 cps.

For detection of multiple product ions from one or more precursor ions the mass spectrometer was operated in multiple reaction monitoring (MRM) mode. The following transitions were monitored for each of the analytes listed below:

PGD2-H2O: 351.300→333.100
d9-PGD2-H2O: 360.400→342.200
d4-PGD2-H2O: 355.400→337.000
PGD2-2H2O: 351.300→315.300
d9-PGD2-2H2O: 360.400→324.400
d4-PGD2-2H2O: 355.400→319.200
PGD2: 351.3→271.2; 351.298→271.200; 351.299→271.200; 351.301→271.200; 351.302→271.200; 351.299→233.100; 351.298→233.1; 351.301→233.100; 351.302→233.100; 351.300→189.100; 351.298→189.100; 351.299→189.100; 351.301→189.100; 351.302→189.100; 351.300→251.200; 351.298→251.200; 351.299→251.200; 351.301→251.200; 351.302→251.200
d9-PGD2: 360.400→280.100; 360.400→232.900; 360.400→189.000; 360.400→250.900
d4-PGD2: 355.400→275.300; 355.400→237.300; 355.400→193.201; 355.400→255.500

Calculations. Integration parameters were set using the Quantitation Wizard in the Analyst Version 1.4 or greater. Sciex, (CA, USA)) program. A standard curve was generated and a metric plot was generated with index on the x-axis vs. the internal standard on the y-axis. Standard curves were used to determine the amount of $PGD_2$ present in each sample. Duplicate calibration curves were used for each batch of samples. A total of 25% of standard points may be excluded from the combined curves if the back-calculated concentrations exceed the theoretical concentrations by >20% at the LLOQ or >15% at other concentrations. No result was reported below the lowest, or above the highest remaining standard. Samples with values less than the minimum reportable dose were calculated and reported as "less than" value. All chromatographic peak shapes were reviewed for consistency. Observation of peak distortion indicated the presence of a contaminant. Where multiple peaks were observed within the chromatogram, to ensure the correct peak was integrated, the retention of the peak integrated was confirmed to correspond to calibrators and quality control samples. Internal standard peak areas vs. index plot were visually reviewed for gross indications of processing and/or technical errors. All internal standard peak areas that visually appeared to be >50% of the neighboring peaks were considered for repeat analysis. All internal standard peak areas that visually appeared to be 33% less than the neighboring peaks were considered for repeat analysis. Such anomalies are good indicators of reagent addition or pipetting errors or technical malfunctions of equipment.

Example 2. Validation of the Measurement of PGD2 in Urine by SPE-LC-MS/MS

Standard Material. The standard lots were prepared by diluting the material from two separate vials of commercially available Prostaglandin D2 MaxSpec Standard purchased from Cayman Chemical Company into a pool of Mass Spect Gold Urine (GoldenWest BioSolutions) with 3.6 µg/mL indomethacin added for stability. The calibration standards used for validation ranged in concentration from 1-1000 pg/mL.

Controls. Clinical Quality Control pools used during this validation were prepared by diluting commercially available Prostaglandin D2 MaxSpec Standard purchased from Cayman Chemical Company into human urine pools. Three control pools were used in each validation batch.

Test procedures. The assay steps were performed according to Urinary Prostaglandin D2 by SPE and LCMS, as described in Example 1. The validation was completed in 10 independent assays (one of which was analyzed twice for establishment of autosampler stability).

Acceptance Criteria. The acceptance criteria for each of the following validation assays are shown in TABLE 4.

TABLE 4

Acceptance Criteria

| PARAMETER | MATERIAL | ACCEPTANCE CRITERIA |
| --- | --- | --- |
| Intra-assay Standard Accuracy and Precision | Five levels of Prostaglandin D2 diluted in charcoal stripped human urine at LLOQ, low, mid, high, and ULOQ target concentrations. Preparation of accuracy and precision samples was independent of standard preparation. Twenty replicates of each level were analyzed in a single batch. | Runs include an LLOQ calibrator level Exempt from QC acceptance criteria Bias ≤ ± 15%; (LLOQ ± 20%) CV ≤ 15%; (LLOQ ≤ 20%) |
| Inter-assay Standard Accuracy and Precision | The above samples were analyzed in six batches, with a minimum of three replicates at each level. Batch processing was performed using different reagent lots as available. | Runs include an LLOQ calibrator level Exempt from QC acceptance criteria Mean inter-assay bias ≤ ± 15%; (LLOQ ± 20%) and at least 2/3 of intra-assay bias values ≤ ± 15% CV ≤ 15%; (LLOQ ≤ 20%) and at least 2/3 of intra-assay CV values within range |
| Intra-assay Sample Precision | Human urine with high, medium and low concentrations of Prostaglandin D2. Six replicates of each level was analyzed in a single batch. | CV ≤ 15%; (LLOQ ≤ 20%) |
| Inter-assay Sample Precision | The above samples were analyzed three times on different days with different lots of reagent if possible. | CV ≤ 15%; (LLOQ ≤ 20%) and at least 2/3 of intra-assay CV values within range |
| Lower Limit of Quantitation (LLOQ) | Prostaglandin D2 diluted in charcoal stripped human urine. Inaccuracy and Imprecision data was used. | Lowest concentration meeting accuracy and precision criteria Response at LLOQ is ≥ 5 times the response of zero calibrator |
| Upper Limit of Quantitation (ULOQ) | Prostaglandin D2 diluted in charcoal stripped human urine. Inaccuracy and Imprecision data was used. | Highest concentration meeting accuracy and precision criteria |
| Blank Matrix Effect | Six lots of blank matrix were analyzed in triplicate | Blank and zero calibrator are free of interference at the retention times of analyte and Internal Standard Response of lowest standard is at least 5 times blank response Double blank response at the IS retention time is ≤ 5% of average IS of calibrators and QC in the same run |
| Internal Standard Interference | Internal Standard in blank matrix was injected as sample. | Blank with IS added <LLOQ. |
| LC system carry-over evaluation | The high standard (10000 pg/mL) followed by a double blank was analyzed in four runs. | Response of the blank following a high sample should be less than the LLOQ. |
| Spike and Recovery | Human urine and calibrator with low level concentrations of Prostaglandin D2 were spiked with Prostaglandin standard material to low, mid and high concentration. Baseline and spiked samples were tested in triplicate. | Mean % Recovery from expected (baseline concentration plus spike) 85-115% (80-120% at LLOQ) At least two-thirds of the sample replicates tested within 85-115% recovery. |
| Dilution Linearity (AMR verification) | Diluted human urine (X2, X4, and X10). Three urine samples were analyzed neat and diluted X2, X4, and X10. Five replicates for each dilution were analyzed for each urine sample. | CV ≤ 15%; (LLOQ ≤ 20%) 85-115% of expected values (based on measurement of neat, undiluted urine) at each dilution level (80-120% if near LLOQ) |
| Extraction Recovery | Urine samples were spiked before and after SPE processing at low, medium and high concentrations. Recovery of samples spiked before SPE processing was compared to those spiked after SPE processing. | No other criteria |
| Autosampler Stability | Autosampler stability was evaluated using calibrators and quality control samples. Duplicate sample sets were included with the batch. The first sample set was injected, then after 3 days the entire batch was injected or re-injected. | Mean post-storage recovery 85-115% (80-120% at LLOQ) of the mean pre-storage concentration with at least two-thirds of the sample replicates tested within 85-115% recovery. |

TABLE 4-continued

Acceptance Criteria

| PARAMETER | MATERIAL | ACCEPTANCE CRITERIA |
|---|---|---|
| Short-term Stability | Short-term sample stability was determined by testing freshly collected human urine (spiked if necessary) that was stored under conditions likely to be encountered in sample handling and laboratory analysis. One aliquot of each sample was analyzed on the same day as preparation, and an additional aliquot of each sample was placed into storage at ≤−55° C. The other aliquots were incubated at room temperature (15-30° C.), refrigerated (2-8° C.), and frozen (≤−10° C.) conditions, then placed into storage at ≤−55° C. until analysis. All samples were analyzed in triplicate. Excluding those tested on the same day as preparation, all samples for a given donor were analyzed in a single batch. | Mean % Recovery from baseline 85-115% (80-120% at LLOQ), with at least two-thirds of the sample replicates at a particular condition tested within 85-115% recovery. |
| Freeze/thaw Stability | Sample freeze/thaw stability was determined using aliquots of the collected human urine used to evaluate short-term stability. One set of aliquots at each level was analyzed on the day of draw, another set was stored at ≤−55° C., and the remaining set will be subjected to an additional 6 freeze/thaw cycles. All samples were analyzed in triplicate. Excluding those tested on the same day as peparation, all samples for a given donor were analyzed in a single batch. | Mean % Recovery from baseline 85-115% (80-120% at LLOQ), with at least two-thirds of the sample replicates at a particular condition tested within 85-115% recovery. |
| Long-term Stability | Baseline determination for long-term ≤−10° C. frozen stability will be performed as part of the short-term and freeze/thaw stability studies. Final measurements to be completed in a minimum of triplicate in future testing. | Mean % Recovery from baseline 85-115% (80%-120% at LLOQ), with at least two-thirds of the sample replicates at a particular condition tested within 85%-115% recovery. |
| Reference Interval Verification | 122 normal patients were analyzed. To qualify as normal, a subject must attest to being in good health and not have a known history of related disease or conditions. | Use EP Evaluator or other appropriate method to establish reference interval. |
| Selectivity | Potential interferents in presence of Prostaglandin D2. A low sample was spiked with candidate substances and analyzed in singlicate. Refer to Deviation 2. | Spiked specimen has 85-115% of expected values for analyte |
| Specificity | Potential interferents were analyzed in absence of analyte by diluting potential interferents in reconstitution buffer. | The measured concentration will be calculated from the standard curve. Ther percent cross-reaction will be calculated as the ratio of the measured concentration to the actual spike concentration of each substance, expressed as a percentage. Insignificant cross-reaction will be defined by a value of <5%. Response <LLOQ |
| Calibration or Standard Curve Precision | Prostaglandin D2 calibrators. | Minimum of six points per curve generated. Goodness of fit is demonstrated by standard curve back-fit calculations. An average variability in concentration of <15% of the expected value is acceptable (20% at LLOQ). |
| Units of measure to report | | pg/mL |
| ULOQ | | 1,000 pg/mL |
| LLOQ | | 1 pg/mL |
| AMR (Analytical Measurement Range) | | 1-4,000 pg/mL |
| Max Dilution Limit | | X4 |
| Primary sample type used | | urine |

Inter- and intra-assay standard accuracy and precision. Five levels of Prostaglandin D2 spiked into charcoal stripped human urine were assayed over seven assay batches. All levels were analyzed twenty times in a single batch and three times in 5 batches, with the exception of accuracy sample Level AA at 1 pg/mL. One validation batch (PGD2_VB1_052020) had low level contamination that was traced to the Reconstitution Solution and therefore analysis of 20 replicates of the 1 pg/mL accuracy sample was repeated for this batch. Accuracy at the low end of the calibration curve was negatively impacted and accuracy and imprecision at 1 pg/mL was omitted from overall validation calculations. The experiment for analysis of 20 replicates of the accuracy sample Level AA at 1 pg/mL was repeated. A total of 175 individual results (20×5+15×5) were collected and analyzed. The samples were chosen to fall within different regions of the reportable range. Accuracy and precision results are summarized in TABLE 5 for the five concentrations ranging from 1-1000 pg/mL. Inter-assay and Intra-assay study results met acceptance criteria for accuracy and precision (TABLE 4).

TABLE 5

Inter- and Intra-Assay Standard Accuracy and Precision
Method Validation: Inaccuracy and Imprecision
Component: Prostaglandin D2
Sample Matrix: Charcoal Stripped Human Urine

| Accuracy Sample Identification | AA | A1 | A5 | A6 | A7 |
|---|---|---|---|---|---|
| Target Concentration (pg/mL) | 1.00 | 10.0 | 300 | 500 | 1000 |
| 85% (80% at AA) of Target Concentration (pg/mL) | 0.800 | 8.50 | 255 | 425 | 850 |
| 115% (120% at AA) of Target Concentration (pg/mL) | 1.20 | 11.5 | 345 | 575 | 1150 |
| Batch # | Measured Concentration (pg/mL) | | | | |
| PGD2_VB1_052020 | | | | | |
| Intra-assay Mean | 1.660 | 10.32 | 325.3 | 525.0 | 1028.7 |
| Intra-assay Standard Deviation | 0.662 | 0.49 | 8.1 | 18.7 | 71.6 |
| Intra-assay Inaccuracy (% Bias) | 66.0 | 3.2 | 8.4 | 5.0 | 2.9 |
| Intra-assay Imprecision (% CV) | 39.9 | 4.7 | 2.5 | 3.6 | 7.0 |
| # Replicates within 85-115% (80-120% at LLOQ) of Target Concentration | 4 | 3 | 3 | 3 | 3 |
| % Replicates within 85-115% (80-120% at LLOQ) of Target Concentration | 20.0% | 100.0% | 100.0% | 100.0% | 100.0% |
| N | 20 | 3 | 3 | 3 | 3 |
| PGD2_VB2_052120 | | | | | |
| Intra-assay Mean | 1.160 | 8.88 | 290.0 | 524.3 | 1019.3 |
| Intra-assay Standard Deviation | 0.157 | 0.52 | 15.4 | 12.9 | 69.9 |
| Intra-assay Inaccuracy (% Bias) | 16.0 | −11.3 | −3.3 | 4.9 | 1.9 |
| Intra-assay Imprecision (% CV) | 13.5 | 5.9 | 5.3 | 2.5 | 6.9 |
| # Replicates within 85-115% (80-120% at LLOQ) of Target Concentration | 14 | 14 | 3 | 3 | 3 |
| % Replicates within 85-115% (80-120% at LLOQ) of Target Concentration | 70.0% | 70.0% | 100.0% | 100.0% | 100.0% |
| N | 20 | 20 | 3 | 3 | 3 |
| PGD2_VB3_052620 | | | | | |
| Intra-assay Mean | 0.940 | 9.94 | 269.6 | 458.6 | 991.3 |
| Intra-assay Standard Deviation | 0.178 | 0.48 | 12.1 | 18.2 | 11.6 |
| Intra-assay Inaccuracy (% Bias) | −6.0 | −0.6 | −10.2 | −8.3 | −0.9 |
| Intra-assay Imprecision (% CV) | 18.9 | 4.9 | 4.5 | 4.0 | 1.2 |
| # Replicates within 85-115% (80-120% at LLOQ) of Target Concentration | 2 | 3 | 18 | 19 | 3 |
| % Replicates within 85-115% (80-120% at LLOQ) of Target Concentration | 66.7% | 100.0% | 90.0% | 95.0% | 100.0% |
| N | 3 | 3 | 20 | 20 | 3 |
| PGD2_VB4_052720 | | | | | |
| Intra-assay Mean | 1.161 | 9.70 | 324.0 | 567.7 | 1068.5 |
| Intra-assay Standard Deviation | 0.263 | 0.49 | 20.2 | 32.5 | 33.3 |
| Intra-assay Inaccuracy (% Bias) | 16.1 | −3.0 | 8.0 | 13.5 | 6.8 |
| Intra-assay Imprecision (% CV) | 22.7 | 5.0 | 6.2 | 5.7 | 3.1 |
| # Replicates within 85-115% (80-120% at LLOQ) of Target Concentration | 2 | 3 | 3 | 2 | 20 |
| % Replicates within 85-115% (80-120% at LLOQ) of Target Concentration | 66.7% | 100.0% | 100.0% | 66.7% | 100.0% |
| n | 3 | 3 | 3 | 3 | 20 |
| PGD2_VB5_052820 | | | | | |
| Intra-assay Mean | 0.957 | 10.40 | 335.7 | 523.3 | 1034.0 |
| Intra-assay Standard Deviation | 0.046 | 0.60 | 17.0 | 30.6 | 63.2 |
| Intra-assay Inaccuracy (% Bias) | −4.3 | 4.0 | 11.9 | 4.7 | 3.4 |
| Intra-assay Imprecision (% CV) | 4.8 | 5.7 | 5.1 | 5.8 | 6.1 |
| # Replicates within 85-115% (80-120% at A1) of Target Concentration | 3 | 3 | 2 | 3 | 3 |
| % Replicates within 85-115% (80-120% at A1) of Target Concentration | 100.0% | 100.0% | 66.7% | 100.0% | 100.0% |
| n | 3 | 3 | 3 | 3 | 3 |

TABLE 5-continued

PGD2_VB6_060120

| | | | | | |
|---|---|---|---|---|---|
| Intra-assay Mean | 0.874 | 10.67 | 311.3 | 485.7 | 951.3 |
| Intra-assay Standard Deviation | 0.060 | 0.74 | 16.9 | 31.1 | 41.8 |
| Intra-assay Inaccuracy (% Bias) | −12.6 | 6.7 | 3.8 | −2.9 | −4.9 |
| Intra-assay Imprecision (% CV) | 6.8 | 6.9 | 5.4 | 6.4 | 4.4 |
| # Replicates within 85-115% (80-120% at LLOQ) of Target Concentration | 3 | 3 | 3 | 3 | 3 |
| % Replicates within 85-115% (80-120% at LLOQ) of Target Concentration | 100.0% | 100.0% | 100.0% | 100.0% | 100.0% |
| n | 3 | 3 | 3 | 3 | 3 |

PGD2_VB8_060420

| | | | | | |
|---|---|---|---|---|---|
| Intra-assay Mean | 0.837 | NA | NA | NA | NA |
| Intra-assay Standard Deviation | 0.090 | NA | NA | NA | NA |
| Intra-assay Inaccuracy (% Bias) | −16.3 | NA | NA | NA | NA |
| Intra-assay Imprecision (% CV) | 10.7 | NA | NA | NA | NA |
| # Replicates within 85-115% (80-120% at LLOQ) of Target Concentration | 2 | NA | NA | NA | NA |
| % Replicates within 85-115% (80-120% at LLOQ) of Target Concentration | 66.7% | NA | NA | NA | NA |
| n | 3 | NA | NA | NA | NA |
| Average Intra-assay Inaccuracy (% Bias) | 8.4 | −0.1 | 3.1 | 2.8 | 1.6 |
| Average Intra-assay Imprecision (% CV) | 16.7 | 5.5 | 4.8 | 4.7 | 4.8 |
| Inter-assay Mean | 1.072 | 9.45 | 290.0 | 487.1 | 1041.2 |
| Inter-assay Standard Deviation | 0.192 | 0.86 | 29.0 | 42.5 | 54.6 |
| Inter-assay Inaccuracy (% Bias) | 7.2 | −5.5 | −3.3 | −2.6 | 4.1 |
| Inter-assay Imprecision (% CV) | 17.9 | 9.1 | 10.0 | 8.7 | 5.2 |
| n | 35 | 35 | 35 | 35 | 35 |

Sample precision. 6 replicates of three levels of Prostaglandin D2 spiked into human urine pools were assayed on 4 separate days. A total of 24 individual results (6×4) were collected and analyzed for sample precision. Results are summarized in TABLE 6. Results showed that the acceptance criteria were met.

TABLE 6

Sample Precision
Method Validation: Imprecision
Component: Prostaglandin D2
Sample Matrix: Human Urine

| Sample Identification Batch # | Normal Pool 1: UPG2 QC1, Lot 20142 | Normal Pool 2: UPG2 QC 2, Lot 20142 | Normal Pool 3: UPG3 QC3, Lot 20141 |
|---|---|---|---|
| | Measured Concentration (pg/mL) | | |
| PGD2_VB1_052020 | | | |
| Intra-assay Mean | NA | NA | 804.5 |
| Intra-assay Standard Deviation | NA | NA | 27.6 |
| Intra-assay Imprecision (% CV) | NA | NA | 3.4 |
| N | NA | NA | 6 |
| PGD2_VB2_052120 | | | |
| Intra-assay Mean | 6.64 | 118.8 | 728.3 |
| Intra-assay Standard Deviation | 0.87 | 4.1 | 16.4 |
| Intra-assay Imprecision (% CV) | 13.2 | 3.4 | 2.2 |
| N | 6 | 6 | 6 |
| PGD2_VB3_052620 | | | |
| Intra-assay Mean | 6.02 | 102.8 | 669.0 |
| Intra-assay Standard Deviation | 0.85 | 10.0 | 18.4 |
| Intra-assay Imprecision (% CV) | 14.2 | 9.7 | 2.8 |
| N | 6 | 6 | 6 |
| PGD2_VB4_052720 | | | |
| Intra-assay Mean | 5.95 | 107.2 | 724.0 |
| Intra-assay Standard Deviation | 0.47 | 9.7 | 27.4 |
| Intra-assay Imprecision (% CV) | 7.9 | 9.1 | 3.8 |
| N | 6 | 6 | 6 |
| PGD2_VB5_052820 | | | |
| Intra-assay Mean | 6.40 | 101.2 | NA |
| Intra-assay Standard Deviation | 1.02 | 8.0 | NA |
| Intra-assay Imprecision (% CV) | 16.0 | 7.9 | NA |
| N | 6 | 6 | 0 |
| Average Intra-assay Imprecision (% CV) | 12.8 | 7.5 | 3.1 |
| Inter-assay Mean | 6.25 | 107.51 | 731.46 |
| Inter-assay Standard Deviation | 0.82 | 10.45 | 53.73 |
| Inter-assay Imprecision (% CV) | 13.2 | 9.7 | 7.3 |
| N | 24 | 24 | 24 |

Sensitivity: LLQQ and ULOQ. The Upper and Lower Limits of Quantitation were determined using the materials used to show Intra- and Inter-Assay Accuracy and Imprecision. The Upper and Lower Limits of Quantitation were determined from data collected during Intra- and Inter-Assay Accuracy and Imprecision Testing. The LLOQ is the lowest activity to meet acceptance criteria and the ULOQ is the highest concentration to meet acceptance criteria. The LLOQ could be demonstrated at 1 pg/mL and ULOQ could be demonstrated at 1000 pg/mL.

Blank matrix Effect. To demonstrate blank matrix effect, six lots of potential blank matrix products were analyzed without the addition of internal standard (IS). Three replicates of each product were processed and analyzed to determine the effect of different lots of blank matrix. The blank and zero calibrator were free of interference at the retention times of the analyte (PGD2) and the internal standard. Response of the lowest internal standard was at least five times the response of the blank. The double blank response at the IS retention time was ≤5% of average IS of calibrators and QC in the same run.

Internal Standard Interference. To demonstrate internal standard interference, a single lot of blank matrix product was analyzed with the addition of internal standard. Three replicates of blank matrix were processed and analyzed to determine the effect of internal standard interference. When the IS in blank matrix was injected as the sample, the mean concentration was determined to be 0.00 pg/mL. Internal Standard added to blank matrix meets acceptance criteria (TABLE 4).

LC System carry-over. To demonstrate LC system Carry-Over, the double blank following each of the high standards in four assay batches was analyzed. The mean percent carry-over was 0.0%. Carry-over study results met acceptance criteria (TABLE 4).

Spike and recovery. Human urine and charcoal stripped human urine with low spiked levels of Prostaglandin D2 were additionally spiked with Prostaglandin D2 standard material at low, mid, and high concentrations. Baseline (low spike) and additionally spiked urine were tested in triplicate. Percent recovery was based on mean baseline concentration of low-spiked material plus the additional theoretical spiked concentration (TABLE 4). Results are summarized in TABLE 7.

Dilutional linearity (AMR verification). To demonstrate linearity of dilution, three human urine samples were assayed at reduced volume. The final dilution factors for the samples analyzed were X1 (neat, normal volume), X2, X4 and X10. Each sample and volume was tested five times in one assay. Expected values were calculated based on average concentrations of the samples run at normal volume (400 uL). Results are summarized in TABLE 8. Dilutional Linearity study results met acceptance criteria for urine samples analyzed using the alternative volumes of 200 uL and 100 uL in addition to the standard sample volume for the assay (400 uL) (TABLE 4). Samples analyzed using 40 uL of urine passed for ⅔ samples tested and failed for the third sample. 40 uL of urine is not acceptable for analysis.

TABLE 8

Dilutional Linearity
Method Validation: Linearity (AMR Verification)
Component(s): Prostaglandin D2
Sample Matrix: Human Urine
Validation Batch: PGD2_VB9_060820

| Sample Volume (uL) | 400 | 200 | 100 | 40 |
|---|---|---|---|---|
| Dilution Factor | Neat | X2 | X4 | X10 |
| Sample Identification | | Calculated Concentration (pg/mL) | | |
| Dilution Sample 1 | 46.4 | 53.6 | 55.9 | 57.6 |
| | 52.3 | 48.8 | 57.3 | 49.2 |
| | 48.0 | 55.4 | 49.2 | _71.9_ |

TABLE 7

Spike and Recovery

Method Validation: Spike and Recovery
Component(s): Prostaglandin D2
Sample Matrix: Human Urine and Charcoal Stripped Human Urine
Validation Batch: PGD2_VB6_060120 and PGD2_VB9_060820

| | Concentration Added to Baseline (pg/mL) | | | | | |
|---|---|---|---|---|---|---|
| | 0.0 | 25.0 | 250.0 | 1750.0 | 0.0 | 625.0 |
| | | Measured Concentration (pg/mL) | | | | |
| Human Urine | 3.60 | _23.9_ | _212.0_ | 1780.0 | 5.60 | 666 |
| (Normal Urine 1) | 4.15 | 24.8 | 218.0 | 1660.0 | 5.45 | 613 |
| | 2.14 | 25.2 | 253.0 | 1570.0 | 5.07 | 610 |
| Mean Conc. | 3.30 | 24.6 | 227.7 | 1670.0 | 5.37 | 629.7 |
| Expected Conc. | NA | 28.3 | 253.3 | 1753.3 | NA | 630.4 |
| Recovery (%) | NA | 87.1 | 89.9 | 95.2 | NA | 99.9 |
| 85% of Expected Concentration | NA | 24.1 | 215.3 | 1490.3 | NA | 535.8 |
| 115% of Expected Concentration | NA | 32.5 | 291.3 | 2016.3 | NA | 724.9 |
| N | 3 | 3 | 3 | 3 | 3 | 3 |
| Charcoal Stripped Human | 20.60 | 41.7 | 244.0 | 1630.0 | 18.7 | 649 |
| Urine (A2) | 21.20 | 40.1 | 251.0 | 1560.0 | 16.4 | 621 |
| | 21.00 | 42.9 | 257.0 | 1750.0 | 19.4 | 584 |
| Mean | 20.93 | 41.6 | 250.7 | 1646.7 | 18.17 | 618.0 |
| Expected Conc. | NA | 45.9 | 270.9 | 1770.9 | NA | 643.2 |
| Recovery (%) | NA | 90.5 | 92.5 | 93.0 | NA | 96.1 |
| 85% of Expected Concentration | NA | 39.0 | 230.3 | 1505.3 | NA | 546.7 |
| 115% of Expected Concentration | NA | 52.8 | 311.6 | 2036.6 | NA | 739.6 |
| N | 3 | 3 | 3 | 3 | 3 | 3 |

Note:
Expected concentration is equal to the mean baseline concentration plus the concentration added to baseline.
Note:
Samples listed in _bold italics and underlined_ were not within 85-115% of expected concentration.
Note:
Original high spike of 1750 pg/mL was initially performed at a level outside the ULOQ of the assay platform (1000 pg/mL). Data was included and high spike experiment was repeated at a level within the assay limits.

TABLE 8-continued

Dilutional Linearity
Method Validation: Linearity (AMR Verification)
Component(s): Prostaglandin D2
Sample Matrix: Human Urine
Validation Batch: PGD2_VB9_060820

| Sample Volume (uL) | 400 | 200 | 100 | 40 |
|---|---|---|---|---|
| Dilution Factor | Neat | X2 | X4 | X10 |
| Sample Identification | Calculated Concentration (pg/mL) | | | |
|  | 51.0 | 52.2 | 53.9 | _58.7_ |
|  | 51.3 | 53.7 | 53.7 | 51.8 |
| Mean | 49.8 | 52.7 | 54.0 | 57.8 |
| Imprecision (% CV) | 5.0% | 4.7% | 5.7% | 15.2% |
| Mean % Recovery Compared to Neat | NA | 105.9% | 108.4% | 116.1% |
| 85% of Neat Concentration | 42.3 | NA | NA | NA |
| 115% of Neat Concentration | 57.3 | NA | NA | NA |
| Dilution Sample 2 | 66.9 | 68.9 | 72.6 | _60.9_ |
|  | 73.9 | 74.1 | 78.3 | 64.3 |
|  | 75.7 | 74.9 | 82.8 | 78.0 |
|  | 76.9 | 71.9 | _63.2_ | 79.8 |
|  | 74.5 | 81.0 | 77.5 | 72.1 |
| Mean | 75.3 | 74.2 | 74.9 | 71.0 |
| Imprecision (% CV) | 5.2% | 6.0% | 10.0% | 11.7% |
| Mean % Recovery Compared to Neat | NA | 98.6% | 99.5% | 94.4% |
| 85% of Neat Concentration | 64.0 | NA | NA | NA |
| 115% of Neat Concentration | 86.5 | NA | NA | NA |
| Dilution Sample 3 | 75.7 | 73.8 | 73.2 | 80.1 |
|  | 80.2 | 87.1 | 83.5 | 74.9 |
|  | 84.7 | 87.5 | 88.5 | 75.2 |
|  | 82.5 | 74.3 | 81.6 | 83.6 |
|  | 78.2 | 77.1 | 85.3 | 83.1 |
| Mean | 81.4 | 80.0 | 82.4 | 79.4 |
| Imprecision (% CV) | 4.3% | 8.5% | 7.0% | 5.3% |
| Mean % Recovery Compared to Neat | NA | 98.2% | 101.3% | 97.5% |
| 85% of Neat Concentration | 69.2 | NA | NA | NA |
| 115% of Neat Concentration | 93.6 | NA | NA | NA |
| Mean Imprecision (% CV) | 4.8% | 6.4% | 7.5% | 10.7% |
| Total replicates within 85-115% of Neat | NA | 100.0% | 93.3% | 80.0% |
| Overall Mean % Recovery Compared to Neat | NA | 100.9% | 103.1% | 102.7% |

Note:
Samples listed in _bold italics and underlined_ were not within 85-115% of neat calculated concentration.

Extraction recovery. To demonstrate extraction recovery, human urine and charcoal stripped human urine with low spiked levels of Prostaglandin D2 were additionally spiked with Prostaglandin D2 standard material at low, mid, and high concentrations both before and after SPE plate processing. Each sample was tested in triplicate. Expected values were calculated based on average concentrations found when spiking samples before SPE plate processing. Results are summarized in TABLE 9.

TABLE 9

Extraction Recovery
Method Validation: Extraction Recovery
Component(s): Prostaglandin D2
Sample Matrix: Human Urine
Validation Batch: PGD2_VB6_060120[1] and PGD2_VB9_060820[2]

| | Pre- or Post-Extraction Spike | |
|---|---|---|
| | Pre-Spiked | Post-Spiked |
| Sample Identification | Calculated Concentration (pg/mL) | |
| Low Cal/Acc_Low Spike[1] | 41.7 | 32.1 |
|  | 40.1 | 35.4 |
|  | 42.9 | 39.4 |
| Mean | 41.6 | 35.6 |
| Mean % Recovery Compared to Pre-Spike | NA | 85.7% |
| 85% of Pre-Spike Concentration | 35.3 | NA |
| 115% of Pre-Spike Concentration | 47.8 | NA |
| Low Cal/Acc_Mid Spike[1] | 244 | 279 |
|  | 251 | 310 |
|  | 257 | 266 |
| Mean | 250.7 | 285.0 |
| Mean % Recovery Compared to Pre-Spike | NA | 113.7% |
| 85% of Pre-Spike Concentration | 213.1 | NA |
| 115% of Pre-Spike Concentration | 288 | NA |
| Low Cal/Acc_High Spike[2] | 649 | 668 |
|  | 621 | 686 |
|  | 584 | 651 |
| Mean | 618.0 | 668.3 |
| Mean % Recovery Compared to Pre-Spike | NA | 108.1% |
| 85% of Pre-Spike Concentration | 525 | NA |
| 115% of Pre-Spike Concentration | 711 | NA |
| *Low Cal/Acc_High Spike[1] | 1630* | 1830* |
|  | 1560* | **_2000*_** |
|  | 1750* | **_1900*_** |
| Mean | 1646.7 | 1910.0 |
| Mean % Recovery Compared to Pre-Spike | NA | 116.0% |
| 85% of Pre-Spike Concentration | 1400 | NA |
| 115% of Pre-Spike Concentration | 1894 | NA |
| Low Sample_Low Spike[1] | 23.9 | 21.4 |
|  | 24.8 | 24.0 |
|  | 25.2 | _18.7_ |
| Mean | 24.6 | 21.4 |
| Mean % Recovery Compared to Pre-Spike | NA | 86.7% |
| 85% of Pre-Spike Concentration | 20.9 | NA |
| 115% of Pre-Spike Concentration | 28.3 | NA |
| Low Sample_Mid Spike[1] | 212 | _276_ |
|  | 218 | _267_ |
|  | 253 | _284_ |
| Mean | 227.7 | 275.7 |
| Mean % Recovery Compared to Pre-Spike | NA | 121.1% |
| 85% of Pre-Spike Concentration | 194 | NA |
| 115% of Pre-Spike Concentration | 262 | NA |
| Low Sample_High Spike[2] | 666 | 687 |
|  | 613 | 657 |
|  | 610 | 695 |
| Mean | 629.7 | 679.7 |
| Mean % Recovery Compared to Pre-Spike | NA | 107.9% |
| 85% of Pre-Spike Concentration | 535 | NA |
| 115% of Pre-Spike Concentration | 724 | NA |
| *Low Sample_High Spike[1] | 1780* | 1900* |
|  | 1660* | 1920* |
|  | 1570* | 1820* |
| Mean | 1670.0 | 1880.0 |
| Mean % Recovery Compared to Pre-Spike | NA | 112.6% |
| 85% of Pre-Spike Concentration | 1420 | NA |
| 115% of Pre-Spike Concentration | 1921 | NA |

Note:
Samples listed in _bold italics and underlined_ were not within 85-115% of neat calculated concentration.

Note:
*Original high pre- and post-spike of 1750 pg/mL was accidentally performed at a level outside the ULOQ of the assay platform (1000 pg/mL). Data was included and pre- and post-high spike experiment was repeated at a level within the assay limits.

Autosampler stability. To demonstrate autosampler stability quality control samples, calibrators, and normal urine samples were analyzed. To validate autosampler stability a batch containing two sets of calibrators and QCs was processed as normal. After completion of assay processing the first set of calibrators, QCs, and normal urines was injected and analyzed. After analysis the assay batch was stored refrigerated in the autosampler prior to reinjection of the first set of samples and first time injection of the second set of calibrators and QCs. The 96-well plates containing the processed assay were stored refrigerated in the autosampler for approximately 3 days, 8 hours, and 36 minutes before injection was completed for all samples. Post-storage recoveries were based on target concentrations for the stored, first time injection samples. Reinjected samples were compared to initial injection results to determine recoveries. Autosampler study results met acceptance criteria. Mean post-storage recovery with 85-115% (80-120% at LLOQ) of the mean pre-storage concentration with at least two-thirds of the sample replicates tested within 85-115% recovery (TABLE 4). Assay batches stored refrigerated for up to 3 days and 8 hours were stable and suitable for first time injection or re-injection to determine Prostaglandin D2 concentrations in human urine.

Reference interval. To establish a reference interval one hundred and twenty-two human urine samples were evaluated. The individual urine samples were collected in-house or purchased from GoldenWest BioSolutions and the individuals tested did not have a known history of related disease or condition. The reference range samples were analyzed in six of the validation batches (PGD2_VB4_052720, PGD2_VB5_052820, PGD2_VB6_060120, PGD2_VB7_060320, PGD2_VB8_060420, and PGD2_VB9_060820). Six of the normal samples (Normal Sample IDs 11, 14, 30-31, and 45-46) had to be analyzed at reduced volume because there was limited sample volume available. Two of these normal samples, Normal Sample IDs 30 and 31, both produced results that were below the limit of quantitation for the assay platform (1 pg/mL) and were therefore not included in the data analysis for reference interval establishment. The other normal samples that produced results within the measurable range of the assay when run on reduced volume were included in the data analysis for reference interval establishment. Two of the normal samples (Normal Sample IDs 16 and 45) were flagged by the EP Evaluator Software as outliers and were not included in the data to establish the reference interval. The results for Prostaglandin D2 concentration in human urine were normalized to each patient's urine creatinine level in order to establish a clinical reference range. The following equation was used to normalize the Prostaglandin D2 levels to urine creatinine levels:

$$\text{Normalized Prostaglandin } D2 \text{ Concentration (ng } PGD2/\text{g creatinine)} = \frac{\text{Urine Prostaglandin } D2 \text{ Concentration (pg/mL)} \times 100}{\text{Urine Creatinine Level (mg/dL)}}$$

Results are summarized in Table 10. The reference interval for Normalized Prostaglandin D2 Concentration in urine as determined by the 97.5th percentile will be <52.6 ng PGD2/g creatinine.

TABLE 10

Reference Interval
Method Validation: Reference Interval
Component(s): Prostaglandin D2
Sample Matrix: Human Urine Samples
PGD2_VB4_052720, PGD2_VB5_052820,
PGD2_VB6_060120, PGD2_VB7_060320,
PGD2_VB8_060420, and PGD2_VB9_060820

| Sample ID | Measured Concentration (pg/mL) | Urine Creatinine (mg/dL) | Normalized Urine PGD2 Concentration (ng PGD2/g creatinine) |
|---|---|---|---|
| 1 | 7.18 | 161.69 | 4.44 |
| 2 | 6.30 | 53.60 | 11.8 |
| 3 | 2.66 | 37.63 | 7.07 |
| 4 | 6.52 | 144.97 | 4.50 |
| 5 | 31.3 | 74.66 | 41.9 |
| 6 | 4.61 | 198.59 | 2.32 |
| 7 | 11.1 | 262.57 | 4.23 |
| 8 | 5.03 | 16.91 | 29.7 |
| 9 | 10.7 | 23.10 | 46.3 |
| 10 | 71.8 | 81.54 | 88.1 |
| *11* | *17.3* | *154.53* | *11.2* |
| 12 | 29.7 | 117.30 | 25.3 |
| 13 | 17.2 | 63.91 | 26.9 |
| *14* | *13.8* | *259.20* | *5.32* |
| 15 | 1.52 | 219.12 | 0.694 |
| 16 | 31.5 | 21.80 | 144 |
| 17 | 14.6 | 200.83 | 7.27 |
| 18 | 21.1 | 145.89 | 14.5 |
| 19 | 14.8 | 127.84 | 11.6 |
| 20 | 16.7 | 200.62 | 8.32 |
| 21 | 7.87 | 63.45 | 12.4 |
| 22 | 4.63 | 279.11 | 1.66 |
| 23 | 13.6 | 188.35 | 7.22 |
| 24 | 23.0 | 86.26 | 26.7 |
| 25 | 13.3 | 91.92 | 14.5 |
| 26 | 30.7 | 134.92 | 22.8 |
| 27 | 10.6 | 101.98 | 10.4 |
| 28 | 12.3 | 199.50 | 6.17 |
| 29 | 53.5 | 111.02 | 48.2 |
| *30* | *BLOQ on Dil\** | *66.45* | *BLOQ on Dil\** |
| *31* | *BLOQ on Dil\** | *203.87* | *BLOQ on Dil\** |
| 32 | 25.6 | 163.53 | 15.7 |
| 33 | 17.9 | 320.55 | 5.58 |
| 34 | 10.4 | 149.09 | 6.98 |
| 35 | 12.5 | 58.04 | 21.5 |
| 36 | 2.79 | 58.45 | 4.77 |
| 37 | 23.2 | 110.10 | 21.1 |
| 38 | 31.5 | 143.24 | 22.0 |
| 39 | 9.04 | 307.37 | 2.94 |
| 40 | 13.2 | 82.09 | 16.1 |
| 41 | 5.38 | 149.10 | 3.61 |
| 42 | 14.2 | 257.33 | 5.52 |
| 43 | 1.01 | 124.76 | 0.810 |
| 44 | 7.64 | 231.16 | 3.31 |
| *45* | *223* | *195.17* | *114* |
| *46* | *12.0* | *248.58* | *4.83* |
| 47 | 5.97 | 364.04 | 1.64 |
| 48 | 9.48 | 25.63 | 37.0 |
| 49 | 9.40 | 35.93 | 26.2 |
| 50 | 24.8 | 151.26 | 16.4 |
| 51 | 2.46 | 178.26 | 1.38 |
| 52 | 21.7 | 223.89 | 9.69 |
| 53 | 12.2 | 109.19 | 11.2 |
| 54 | 7.25 | 183.58 | 3.95 |
| 55 | 4.35 | 179.61 | 2.42 |
| 56 | 9.19 | 252.66 | 3.64 |
| 57 | 1.95 | 225.20 | 0.866 |
| 58 | 5.72 | 44.27 | 12.9 |
| 59 | 4.58 | 118.17 | 3.88 |
| 60 | 25.4 | 292.16 | 8.69 |
| 61 | 23.6 | 301.91 | 7.82 |
| 62 | 26.9 | 184.47 | 14.6 |
| 63 | 10.3 | 124.24 | 8.29 |
| 64 | 21.7 | 103.21 | 21.0 |
| 65 | 1.79 | 130.49 | 1.37 |
| 66 | 8.92 | 49.33 | 18.1 |

TABLE 10-continued

Reference Interval
Method Validation: Reference Interval
Component(s): Prostaglandin D2
Sample Matrix: Human Urine Samples
PGD2_VB4_052720, PGD2_VB5_052820,
PGD2_VB6_060120, PGD2_VB7_060320,
PGD2_VB8_060420, and PGD2_VB9_060820

| Sample ID | Measured Concentration (pg/mL) | Urine Creatinine (mg/dL) | Normalized Urine PGD2 Concentration (ng PGD2/g creatinine) |
|---|---|---|---|
| 67 | 8.09 | 141.31 | 5.73 |
| 68 | 4.33 | 95.66 | 4.53 |
| 69 | 3.19 | 247.74 | 1.29 |
| 70 | 0.00 | 220.56 | 0.000 |
| 71 | 8.77 | 182.55 | 4.80 |
| 72 | 10.10 | 324.09 | 3.12 |
| 73 | 1.91 | 291.94 | 0.654 |
| 74 | 10.7 | 175.26 | 6.11 |
| 75 | 7.25 | 373.40 | 1.94 |
| 76 | 4.52 | 291.15 | 1.55 |
| 77 | 9.28 | 18.25 | 50.8 |
| 78 | 2.58 | 213.32 | 1.21 |
| 79 | 8.98 | 63.48 | 14.1 |
| 80 | 21.1 | 141.36 | 14.9 |
| 81 | 5.72 | 131.08 | 4.36 |
| 82 | 12.2 | 260.22 | 4.69 |
| 83 | 1.65 | 275.83 | 0.598 |
| 84 | 44.6 | 114.38 | 39.0 |
| 85 | 16.8 | 200.13 | 8.39 |
| 86 | 21.7 | 41.04 | 52.9 |
| 87 | 3.48 | 282.78 | 1.23 |
| 88 | 20.7 | 126.47 | 16.4 |
| 89 | 10.4 | 252.59 | 4.12 |
| 90 | 23.3 | 74.48 | 31.3 |
| 91 | 19.1 | 204.41 | 9.34 |
| 92 | 12.7 | 161.75 | 7.85 |
| 93 | 20.1 | 126.90 | 15.8 |
| 94 | 33.6 | 324.66 | 10.3 |
| 95 | 8.76 | 268.35 | 3.26 |
| 96 | 24.5 | 176.87 | 13.9 |
| 97 | 0.00 | 167.28 | 0.000 |
| 98 | 9.42 | 210.13 | 4.48 |
| 99 | 11.9 | 116.99 | 10.2 |
| 100 | 15.0 | 195.90 | 7.66 |
| 101 | 21.1 | 297.99 | 7.08 |
| 102 | 19.2 | 237.02 | 8.10 |
| 103 | 13.4 | 230.51 | 5.81 |
| 104 | 6.87 | 318.93 | 2.15 |
| 105 | 38.9 | 86.23 | 45.1 |
| 106 | 18.9 | 188.80 | 10.0 |
| 107 | 48.7 | 156.59 | 31.1 |
| 108 | 10.7 | 33.16 | 32.3 |
| 109 | 0.00 | 209.67 | 0.000 |
| 110 | 5.15 | 151.98 | 3.39 |
| 111 | 6.75 | 160.22 | 4.21 |
| 112 | 30.1 | 184.70 | 16.3 |
| 113 | 31.9 | 221.70 | 14.4 |
| 114 | 23.1 | 120.39 | 19.2 |
| 115 | 15.8 | 207.79 | 7.60 |
| 116 | 30.8 | 50.30 | 61.2 |
| 117 | 4.26 | 230.64 | 1.85 |
| 118 | 16.3 | 136.44 | 11.9 |
| 119 | 13.4 | 109.57 | 12.2 |
| 120 | 3.98 | 126.04 | 3.16 |
| 121 | 1.34 | 193.23 | 0.693 |
| 122 | 5.97 | 83.13 | 7.18 |
| Mean Concentration (pg/mL) | 16.122 | 165.545 | 14.726 |
| Standard Deviation | 22.355 | 83.945 | 20.876 |

Selectivity. To demonstrate selectivity, potential interferents in the presence of Prostaglandin D2 were analyzed. Multiple replicates of an accuracy sample were processed as normal and the interferents were added individually to the 12×75 glass tubes prior to sample addition and pre-SPE processing. Baseline samples (with no added interferent) were analyzed in triplicate and samples containing interferents were analyzed in singlicate. Recovery in the presence of interferents was based on the mean concentration of the baseline sample. Results are summarized in TABLE 11. Not all potential interferents passed selectivity study acceptance criteria. Δ12-Prostaglandin D2 and 15(R)-Prostaglandin D2 had >85-115% recovery from baseline and therefore did not meet acceptance criteria (TABLE 4). Δ12-Prostaglandin D2 is one of the initial chemical decomposition products of PGD2. The retention time of Δ12-Prostaglandin D2 is 1.14 minutes with the retention time of Prostaglandin D2 being in the range of 1.58-1.71 minutes (Refer to TABLE 12 for retention times). The measured concentration in TABLE 12 is most likely due to a result of chemical impurities in the commercially available product. While 15(R)-Prostaglandin D2 is commercially available it has not been reported at as an endogenous metabolite of Prostaglandin D2. It will therefore not cause interference issues with the assay platform when analyzing human urine.

TABLE 11

Selectivity
Method Validation: Selectivity
Component(s): Prostaglandin D2 with Potential Interferents
Sample Matrix: Charcoal Stripped Human Urine spiked with
Prostaglandin D2 and Potential Interferents
Validation Batch: PGD2_VB9_060820 and PGD2_VB10_061520

| Sample Identification | Measured Concentration (pg/mL) | Mean Measured Concentration (pg/mL) |
|---|---|---|
| No Interferent- Sample Baseline | 18.7 | 18.2 |
| | 16.4 | |
| | 19.4 | |
| Interferent Identification | Measured Concentration (pg/mL) | % Recovery from Sample Baseline |
| Specificity 1 (2,3-dinor-11b-Prostaglandin F2a) | 17.5 | 96.3% |
| Specificity 2 (13,14-dihydro-15-keto Prostaglandin D2) | 15.5 | 85.3% |
| Specificity 3 (PGDM) | 18.9 | 104.0% |
| Specificity 4 (Δ2-Prostaglandin J2) | 17.8 | 98.0% |
| Specificity 5 (tetranor-PGJM) | 16.4 | 90.3% |
| Specificity 6 (11b-13,14-dihydro-15-keto Prostaglandin F2a) | 19.6 | 107.9% |
| Specificity 7 (5-trans Prostaglandin D2) | 19.1 | 105.1% |
| Specificity 8 (Prostaglandin F2a) | 19.0 | 104.6% |
| No Interferent- Sample Baseline | 18.7 | 18.2 |
| | 16.4 | |
| | 19.4 | |
| Specificity 9 (8-isoProstaglandin F2a) | 16.3 | 89.7% |
| Specificity 10 (15-deoxy-Δ12,14-Prostaglandin D2) | 15.7 | 86.4% |
| Specificity 11 (Δ12-Prostaglandin D2) | 164 | 902.8% |
| Specificity 12 (ent-Prostaglandin F2a) | 18.5 | 101.8% |
| Specificity 13 (15(R)-Prostaglandin D2) | 653 | 3594.5% |
| No Interferent- Sample Baseline | 15.7 | 15.7 |
| | 16.8 | |
| | 14.6 | |

TABLE 11-continued

Selectivity
Method Validation: Selectivity
Component(s): Prostaglandin D2 with Potential Interferents
Sample Matrix: Charcoal Stripped Human Urine spiked with
Prostaglandin D2 and Potential Interferents
Validation Batch: PGD2_VB9_060820 and PGD2_VB10_061520

| Sample Identification | Measured Concentration (pg/mL) | Mean Measured Concentration (pg/mL) |
|---|---|---|
| Specificity 14 (Prostaglandin E2) | 15.1 | 96.2% |

Specificity. To demonstrate specificity, blank matrix spiked with potential interferents were analyzed. All samples were analyzed in singlicate. Not all potential interferents passed specificity study acceptance criteria. Δ12-Prostaglandin D2 recovered at 14.7% and 15(R)-Prostaglandin D2 recovered at 31.3% did not meet acceptance criteria (TABLE 4). Δ12-Prostaglandin D2 is one of the initial chemical decomposition products of PGD2. The retention time of Δ12-Prostaglandin D2 is 1.14 minutes with the retention time of Prostaglandin D2 being in the range of 1.58-1.71 minutes. While 15(R)-Prostaglandin D2 is commercially available it has not been reported at as an endogenous metabolite of Prostaglandin D2. It will therefore not cause interference issues with the assay platform when analyzing human urine.

TABLE 12

Specificity

Method Validation: Specificity
Component(s): Prostaglandin D2
Sample Matrix: Charcoal Stripped Human Urine Spiked with Potential Interferents
Assay Date: PGD2_VB9_060820 and PGD2_VB10_061520

| Sample ID | Interferent Compound | Molecular Weight | Spiked Concentration (pg/mL) | Retention Time (Minutes) | Measured Concentration (pg/mL) | % Recovery |
|---|---|---|---|---|---|---|
| Specificity 1 | 2,3-dinor-11β-Prostaglandin F2α | 326.4 | 1000 | Not in Window | 0.176 | 0.0% |
| Specificity 2 | 13,14-dihydro-15-keto Prostaglandin D2 | 352.5 | 1000 | Not in Window | 0.136 | 0.0% |
| Specificity 3 | PGDM | 328.4 | 1000 | Not in Window | 0.228 | 0.0% |
| Specificity 4 | Δ12-Prostaglandin J2 | 334.5 | 1000 | 1.04 | 0.191 | 0.0% |
| Specificity 5 | tetranor-PGJM | 310.3 | 1000 | Not in Window | 0.228 | 0.0% |
| Specificity 6 | 11β-13,14-dihydro-15-keto Prostaglandin F2α | 354.5 | 1000 | Not in Window | 0.191 | 0.0% |
| Specificity 7 | 5-trans Prostaglandin D2 | 352.5 | 1000 | 1.40 | 25.2 | 2.5% |
| Specificity 8 | Prostaglandin F2α | 354.5 | 1000 | Not in Window | 0.541 | 0.1% |
| Specificity 9 | 8-isoProstaglandin F2α | 354.5 | 1000 | Not in Window | 0.227 | 0.0% |
| Specificity 10 | 15-deoxy-Δ12,14-Prostaglandin D2 | 316.4 | 1000 | Not in Window | 0.348 | 0.0% |
| Specificity 11 | Δ12-Prostaglandin D2 | 352.5 | 1000 | 1.14 | 147 | 14.7% |
| Specificity 12 | ent-Prostaglandin F2α | 354.5 | 1000 | Not in Window | 0.495 | 0.0% |
| Specificity 13 | 15(R)-Prostaglandin D2 | 352.5 | 1000 | 1.66 | 313 | 31.3% |
| Specificity 14 | Prostaglandin E2 | 352.5 | 352.5 | 0.72 | No Peak | 0.0% |

Retention time of Prostaglandin D2 ranged from 1.58-1.71 minutes for batches that Selectivity Samples were run in.

Calibration or standard curve accuracy and precision. Eleven standard points (ten of which were non-zero) were included in each run to define the calibration curve. A standard curve was generated using ten standards having concentrations of 0, 1, 2, 5, 10, 30, 50, 100, 300, 500 and 1000 pg/mL. The lowest non-zero point has a target concentration of 1 pg/mL Prostaglandin D2. Analyst software was used to plot the data using a quadratic fit function with 1/x weighting. Standard curve back-fit data from all ten validation batches was tabulated (with 13 total standard curves tabulated—the autosampler stability batch had more than one set of standards and one of the standard curves was re-injected for autosampler reinjection stability). The correlation coefficient was greater than 0.99 for all replicates. Calibrator/Standard Curve results met acceptation criteria for bias and precision.

Example 3. Measurement of PGD2 in Serum by SPE-LC-MS/MS

Specimens. All studies were performed using serum samples. Acceptable sample volumes are shown in TABLE 13.

TABLE 13

Specimen Collection

| Adult: | 5 mL serum is acceptable |
| Pediatric: | 2.5 mL serum is acceptable |
| Minimum: | 1 mL serum is acceptable |

Serum samples were collected into red top tubes and frozen immediately. Specimens were stored according to the following conditions:

Short Term Storage
  Serum Frozen (≤−10° C. and ≤−55° C.): 7 days
  Serum Refrigerated (2-8° C.): Strictly frozen storage. Do not store refrigerated.
  Serum Room Temperature (15-30° C.): Strictly frozen storage. Do not store at room temperature.

Serum Freeze/Thaw (≤−10° C.): 2 Cycles (three total thaws)

Long Term Storage
  Serum Frozen (≤−10° C.): 70 days

Shipping Conditions:
  Serum Frozen (≤−10° C.): on dry ice

Assay parameters. The assay was conducted according to the parameters provided in TABLE 14.

TABLE 14

Assay Parameters

| Parameter | | Value or Criteria | |
|---|---|---|---|
| Reportable Range | AMR (LLOQ-ULOQ) | Maximum Dilution/Concentration | Units of Measure |
| Prostaglandin D2 | 1-1000 pg/mL | X5/5000 pg/mL | pg/mL |
| Alert/Critical Values | | Not Applicable. | |
| Repeat Rules | | Repeat at reduced volume if greater than 1000 pg/mL. | |
| Max Dilution | | Reduced volume down to 100 µL, is allowable. | |
| Preferred Specimen | | Serum collected in a red top tube is the only acceptable sample type. | |

Acceptance Criteria. No more than 25% of all standard curve values may be deleted. Previous standard curve data may be used to identify standard points to delete. Standard curve regression was based upon individual replicates, and each replicate was considered a point for acceptance rules.

Reduced volume analysis. Undiluted samples with results above 1000 pg/mL were retested at reduced volume. Samples can be analyzed using as little as 100 µL when necessary. Dilution factor must be applied.

Assay procedure—sample preparation. Standards, controls, and samples were thawed and then vortexed three times. 500 µL of standards, controls, and samples were pipetted into the appropriately labeled 12×75 glass tubes. Four double blank tubes were left empty. Using a repeater pipette, 100 µL of internal standard was added to each tube, except for the double blanks. The vials were then covered with parafilm and vortexed using a multi-tube vortex mixer 10 times. Next, 1.4 mL 1% formic acid in 10/90 acetonitrile/water was added to each tube and then the tubes were covered and vortexed for 10 minutes at 1200-1500 RPM. Tubes were then centrifuges at 3500 RPM for 10 minutes.

Assay procedure SPE plate processing. A Strata X Pro 96-well plate (Phenomenex Catalog #8E-5536-TGA, or equivalent) was placed on top of a waste collection plate. 1 mL of methanol was added to each well and the wells were drained by gravity without the use of positive pressure. 1 mL of 5% methanol in water was then added to each of the wells drained by gravity without the use of positive pressure. The entire volume of diluted standards, controls, and samples were added to the corresponding wells of the plate. The wells were first drained by gravity and then positive pressure was applied on low setting. 1 mL of 5% methanol in water was added to each of the wells of the 96-well plate and the wells were drained by gravity and then positive pressure was applied on low setting. 1 mL of 20% methanol in water with 2% ammonium hydroxide was then added to each of the wells and the wells drained by gravity and then positive pressure was applied on low setting. Next, 1 mL of 5% methanol in water was added to each of the wells and after the wells were drained by gravity positive pressure was applied on low setting. Next, 1 mL of 30% methanol in water with 2% formic acid was added to each of the wells and after the wells were drained by gravity, positive pressure was applied on low setting. 1 mL of 5% methanol in water was then added to each of the wells and the wells drained by gravity followed by positive pressure applied on low setting. Next, 1 mL of 40% methanol in water was added to each of the wells and the wells were drained by gravity and then positive pressure was applied on low setting. The positive pressure setting was switched to high for 1 minute. Next, the plate was placed on top of a new 1.2 mL 96-well collection plate and 300 µL of 2% acetic acid in chloroform was added to each of the wells of the sample/standard plate. The wells were drained by gravity and then positive pressure was applied on low setting. Again, 300 µL of 2% acetic acid in chloroform was added to each of the wells. The wells were again drained by gravity, and then positive pressure was applied on low setting. The 1.2 mL 96-well plate with collected samples was then placed into a TurboVap 96 Concentration Workstation (Biotage Life Sciences) for approximately 30 mins at 40° C. until samples were dry. Then, 120 µL of $PGD_2$ reconstitution solution (3.33 ng/mL $PGD_2$-$d_4$ internal standard in 1:3 methanol:10 mM ammonium acetate) was added to all wells, the plate was sealed, and mixed four times for 30 seconds (for a total of 2 minutes). The 96-well plate was then positioned in the LC-MS/MS Autosampler.

HTLC-MS/MS Procedure. For HTLC purification of $PGD_2$, a Phenomenex Kinetex 2.6 µm C18(2) 100 Å, 150×4.6 mm column was used. All LC system reagents were filled and LC pumps were primed to remove any bubbles from mobile phase lines or to remove mobile phase from previous assays. The mass spectrometer was then equilibrated for 1 minute. The Aria system (Aria OS Version 1.4 or greater, Cohesive Technologies (MA, USA)) was started. Aria TX4 HTLC System, Cohesive Technologies, (MA, USA) consisting of 4 each: 1100 Series Quaternary Pump, 1100 Series Binary Pump, 1100 Series Vacuum Degasser, or 8 Series 1200 Binary Pump and 4 Series 1200 Vacuum Degasser were started and primed at 5 mL per minute for 5 minutes for each solvent to be used. Test injections were performed using $UPGD_2$ system suitability test (SST). The loading pump was run using a gradient starting with 60% mobile phase A (0.1% formic acid in water) and 40% mobile phase B (100% acetonitrile) at a flow rate of 0.8 mL/min. The eluting pump was run with 100% mobile phase A and 0% mobile phase B at a flow rate of 0.00 mL/min.

For MS/MS, an AB SCIEX API5000 triple quadrupole mass spectrometer, operating in negative ion electrospray ionization (ESI) mode (Turboionspray) was used for detection. Quantification of analyte and internal standard was performed in selected reaction monitoring mode (SRM) with the use of ion summing. For $PGD_2$ the 351.3→233.1 transition was monitored. For the internal standard ($PGD_2$-$d_9$), the 360.4→232.9 transition was monitored. A resulting MS/MS scan of the $PGD_2$ system suitability test (SST) is shown in FIG. 5. For FIG. 5, $PGD_2$-$H_2O$ peaks of 351.300 and 333.100 and $PGD_2$ SST peaks of 351.298 and 233.100 were analyzed. The signal:noise (S/N) ratio was 5.5. The peak intensity was 7.7e+2 counts per second (cps) with a Ymax of 2.2e+2 cps and Ymin of 8.0e+1 cps.

For detection of multiple product ions from one or more precursor ions the mass spectrometer was operated in multiple reaction monitoring (MRM) mode. The following transitions were monitored for each of the analytes listed below:

PGD2-H2O: 351.300→333.100
d9-PGD2-H2O: 360.400→342.200
d4-PGD2-H2O: 355.400→337.000
PGD2-2H2O: 351.300→315.300
d9-PGD2-2H2O: 360.400→324.400
d4-PGD2-2H2O: 355.400→319.200
PGD2: 351.3→271.2; 351.298→271.200; 351.299→271.200; 351.301→271.200; 351.302→271.200; 351.299→233.100; 351.298→233.1; 351.301→233.100; 351.302→233.100; 351.300→189.100; 351.298→189.100; 351.299→189.100; 351.301→189.100; 351.302→189.100; 351.300→251.200; 351.298→251.200; 351.299→251.200; 351.301→251.200; 351.302→251.200
d9-PGD2: 360.400→280.100; 360.400→232.900; 360.400→189.000; 360.400→250.900
d4-PGD2: 355.400→275.300; 355.400→237.300; 355.400→193.201; 355.400→255.500

Calculations. Integration parameters were set using the Quantitation Wizard in the Analyst Version 1.4 or greater. Sciex, (CA, USA)) program. A standard curve was generated and a metric plot was generated with index on the x-axis vs. the internal standard on the y-axis. A standard curve was generated using ten standards having concentrations of 0, 1, 2, 5, 10, 30, 50, 100, 300, 500 and 1000 pg/mL. Standard curves were used to determine the amount of $PGD_2$ present in each sample. Duplicate calibration curves were used for each batch of samples. A total of 25% of standard points may be excluded from the combined curves if the back-calculated concentrations exceed the theoretical concentrations by >20% at the LLOQ or >15% at other concentrations. No result was reported below the lowest, or above the highest remaining standard. Samples with values less than the minimum reportable dose were calculated and reported as "less than" value. All chromatographic peak shapes were reviewed for consistency. Observation of peak distortion indicated the presence of a contaminant. Where multiple peaks were observed within the chromatogram, to ensure the correct peak was integrated, the retention of the peak integrated was confirmed to correspond to calibrators and quality control samples. Internal standard peak areas vs. index plot were visually reviewed for gross indications of processing and/or technical errors. All internal standard peak areas that visually appeared to be >50% of the neighboring peaks were considered for repeat analysis. All internal standard peak areas that visually appeared to be 33% less than the neighboring peaks were considered for repeat analysis. Such anomalies are good indicators of reagent addition or pipetting errors or technical malfunctions of equipment. The correlation coefficient was greater than 0.99 for all replicates.

Example 4. Validation of the Measurement of PGD2 in Serum by SPE-LC-MS/MS

Standard Material. The standard lots were prepared by diluting the material from two separate vials of commercially available Prostaglandin D2 MaxSpec Standard purchased from Cayman Chemical Company into 6% BSA with 3.6 μg/mL Indomethacin and 50 μg/mL BHT added for stability. The calibration standards used for validation ranged in concentration from 1-1000 pg/mL.

Controls. Clinical Quality Control pools used during this validation were prepared by diluting commercially available Prostaglandin D2 MaxSpec Standard purchased from Cayman Chemical Company into human serum pools. Four control pools were used in each validation batch.

Test procedures. The assay steps were performed according to Serum Prostaglandin D2 by SPE and LCMS, as described in Example 3. The validation was completed in 10 independent assays (one of which was analyzed twice for establishment of autosampler stability).

Acceptance Criteria. The acceptance criteria for each of the following validation assays are shown in TABLE 15.

TABLE 15

| | Acceptance Criteria | |
|---|---|---|
| PARAMETER | MATERIAL | ACCEPTANCE CRITERIA |
| Intra-assay Standard Accuracy and Precision | Five levels of Prostaglandin D2 diluted in 6% BSA at LLOQ, low, mid, high, and ULOQ target concentrations. Preparation of accuracy and precision samples was independent of standard preparation. Twenty replicates of each level were analyzed in a single batch. | Runs include an LLOQ calibrator level Exempt from QC acceptance criteria Bias ≤ ± 15%; (LLOQ 20%) CV ≤15%; (LLOQ ≤20%) |
| Inter-assay Standard Accuracy and Precision | The above samples were analyzed in six batches, with a minimum of three replicates at each level. Batch processing was performed using different reagent lots as available. | Runs include an LLOQ calibrator level Exempt from QC acceptance criteria Mean inter-assay bias ≤ ± 15%; (LLOQ 20%) and at least 2/3 of intra-assay bias values ≤ ± 15% CV ≤15%; (LLOQ ≤20%) and at least 2/3 of intra-assay CV values within range |
| Intra-assay Sample Precision | Human serum with high, medium and low concentrations of Prostaglandin D2. Six replicates of each level was analyzed in a single batch. | CV ≤15%; (LLOQ ≤20%) |

TABLE 15-continued

Acceptance Criteria

| PARAMETER | MATERIAL | ACCEPTANCE CRITERIA |
|---|---|---|
| Inter-assay Sample Precision | The above samples were analyzed three times on different days with different lots of reagent if possible. | CV ≤15%; (LLOQ ≤20%) and at least 2/3 of intra-assay CV values within range |
| Lower Limit of Quantitation (LLOQ) | Prostaglandin D2 diluted in 6% BSA. Inaccuracy and Imprecision data was used. | Lowest concentration meeting accuracy and precision criteria Response at LLOQ is ≥5 times the response of zero calibrator |
| Upper Limit of Quantitation (ULOQ) | Prostaglandin D2 diluted in 6% BSA. Inaccuracy and Imprecision data was used. | Highest concentration meeting accuracy and precision criteria |
| Blank Matrix Effect | Six lots of blank matrix were analyzed in triplicate | Blank and zero calibrator are free of interference at the retention times of analyte and Internal Standard Response of lowest standard is at least 5 times blank response Double blank response at the IS retention time is ≤5% of average IS of calibrators and QC in the same run |
| Internal Standard Interference | Internal Standard in blank matrix was injected as sample. | Blank with IS added < LLOQ. |
| Effect of, Icteric and Hemolyzed samples | Icteric, and hemolyzed samples were prepared by adding using the Sun Assurance ® Interference Kit as directed by the manufacturer. A minimum of 3 replicates were tested for each sample type. | Recovery from baseline is 85-115% in at least 2/3 of the samples tested at each condition. |
| LC system carry-over evaluation | The high standard (10000 pg/mL) followed by a double blank was analyzed in four runs, | Response of the blank following a high sample should be less than the LLOQ. |
| Spike and Recovery | Human serum and calibrator with low level concentrations of Prostaglandin D2 were spiked with Prostaglandin standard material to low, mid and high concentration. Baseline and spiked samples were tested in triplicate, | Mean % Recovery from expected (baseline concentration plus spike) 85-115% (80-120% at LLOQ) At least two-thirds of the sample replicates tested within 85-115% recovery. |
| Dilution Linearity (AMR verification) | Reduced volumes of human serum (250 uL, 100 uL, and 50 uL) were analyzed. Three serum samples were analyzed using the standard sample volume of 500 uL as well as the listed reduced volumes. Five replicates for each sample volume were analyzed for each serum sample. Dilution factors were applied. | CV ≤15%; (LLOQ ≤20%) 85-115% of expected values (based on measurement of neat, undiluted serum) at each dilution level (80-120% if near LLOQ) |
| Extraction Recovery | Serum samples were spiked before and after SPE processing at low, medium and high concentrations. Recovery of samples spiked before SPE processing was compared to those spiked after SPE processing (TABLE 20). | No other criteria |
| Autosampler Stability | Autosampler stability was evaluated using calibrators and quality control samples. Duplicate sample sets were included with the batch. The first sample set was injected, then after 3 days the entire batch was injected or re-injected. | Mean post-storage recovery 85-115% (80-120% at LLOQ) of the mean pre-storage concentration with at least two-thirds of the sample replicates tested within 85-115% recovery. |
| Short-term Stability | Short-term sample stability was determined by testing freshly collected human serum (spiked if necessary) that was stored under conditions likely to be encountered in sample handling and laboratory analysis. One aliquot of each sample was analyzed on the same day as preparation, and an additional aliquot of each sample was placed into storage at ≤55° C. The other aliquots were incubated at room temperature (15-30° C.), refrigerated (2-8° C.), and frozen (≤-10° C.) conditions, then placed into storage at ≤-55° C. until analysis. All samples were analyzed in triplicate. Excluding those tested on the same day as preparation, all samples for a given donor were analyzed in a single batch. | Mean % Recovery from baseline 85-115% (80-120% at LLOQ), with at least two-thirds of the sample replicates at a particular condition tested within 85-115% recovery. |

TABLE 15-continued

Acceptance Criteria

| PARAMETER | MATERIAL | ACCEPTANCE CRITERIA |
|---|---|---|
| Freeze/thaw Stability | Sample freeze/thaw stability was determined using aliquots of the collected human serum used to evaluate short-term stability. One set of aliquots at each level was analyzed on the day of draw, another set was stored at ≤-55° C., and the remaining set will be subjected to an additional 6 freeze/thaw cycles. All samples were analyzed in triplicate. Excluding those tested on the same day as preparation, all samples for a given donor were analyzed in a single batch. | Mean % Recovery from baseline 85-115% (80-120% at LLOQ), with at least two-thirds of the sample replicates at a particular condition tested within 85-115% recovery. |
| Long-term Stability | Baseline determination for long-term ≤-10° C. frozen stability will be performed as part of the short-term and freeze/thaw stability studies. Final measurements to be completed in a minimum of triplicate in future testing. | Mean % Recovery from baseline 85-115% (80-120% at LLOQ), with at least two-thirds of the sample replicates at a particular condition tested within 85-115% recovery. |
| Reference Interval Verification | 138 normal patients were analyzed. To qualify as normal, a subject must attest to being in good health and not have a known history of related disease or conditions. | Use EP Evaluator or other appropriate method to establish reference interval. |
| Selectivity | Potential interferents in presence of Prostaglandin D2. A low sample was spiked with candidate substances and analyzed in singlicate. | Spiked specimen has 85-115% of expected values for analyte |
| Specificity | Potential interferents were analyzed in absence of analyte by diluting potential interferents in reconstitution buffer. | The measured concentration will be calculated from the standard curve. The percent cross-reaction will be calculated as the ratio of the measured concentration to the actual spike concentration of each substance, expressed as a percentage. Insignificant cross-reaction will be defined by a value of <5%. Response < LLOQ |
| Sample Tube Type | Red top serum and SST serum from three donors were analyzed and measured in triplicate. | Recovery from red top serum is 85-115% in at least 2/3 of the samples tested for the SST serum. |
| Freeze/thaw Stability of Calibrators | Calibrator freeze/thaw stability was determined by including an aliquot of spiked calibrator material in the freeze thaw cycles that were performed for the serum samples. At the end of each thaw cycle an aliquot of calibrator material was made and placed into storage at ≤-55° C. until final analysis. | Mean % Recovery from target 85-115% (80-120% at LLOQ), with at least two-thirds of the sample replicates at a particular condition tested within 85-115% recovery. |
| Calibration or Standard Curve Precision | Serum Prostaglandin D2 calibrators. | Minimum of six points per curve generated. Goodness of fit is demonstrated by standard curve back-fit calculations. An average variability in concentration of <15% of the expected value is acceptable (20% at LLOQ). |
| Units of measure to report | | pg/mL |
| ULOQ | | 1,000 pg/mL |
| LLOQ | | 1 pg/mL |
| AMR (Analytical Measurement Range) | | 1-5,000 pg/mL |
| Max Dilution Limit | | X5 |
| Primary sample type used | | serum |

Inter- and intra-assay standard accuracy and precision. Six levels of Prostaglandin D2 spiked into 6% BSA were assayed over six assay batches. All levels were analyzed twenty times in a single batch and six times in 5 batches. A total of 300 individual results (20×6+30×6) were collected and analyzed. The samples were chosen to fall within different regions of the reportable range. Accuracy and precision results are summarized in Table 16 for the six concentrations ranging from 1-1000 pg/mL. Inter- and Intra-assay study results met acceptance criteria for accuracy and precision.

TABLE 16

Accuracy and Precision: Intra-Assay

Method Validation: Inaccuracy and Imprecision
Component: Prostaglandin D2
Sample Matrix: Prostaglandin D2 diluted with 6% BSA

| Sample Identification | A1 | A2 | A3 | A4 | A5 | A6 |
|---|---|---|---|---|---|---|
| Target Concentration (pg/mL) | 1.00 | 2.00 | 10.0 | 250 | 500 | 1000 |
| 85% (80% at A1) of Target Concentration (pg/mL) | 0.800 | 1.70 | 8.50 | 213 | 425 | 850 |
| 115% (120% at A1) of Target Concentration (pg/mL) | 1.20 | 2.30 | 11.5 | 288 | 575 | 1150 |
| Batch # | \multicolumn{6}{c}{Measured Concentration (pg/mL)} | | | | | |
| PGD2_Serum_100820_Batch 1 | | | | | | |
| Intra-assay Mean | 0.967 | 2.12 | 9.7 | 260.3 | 516.0 | 1025.7 |
| Intra-assay Standard Deviation | 0.215 | 0.23 | 0.6 | 19.9 | 22.5 | 47.0 |
| Intra-assay Inaccuracy (% Bias) | −3.3 | 5.9 | −3.1 | 4.1 | 3.2 | 2.6 |
| Intra-assay Imprecision (% CV) | 22.2 | 11.1 | 5.8 | 7.6 | 4.4 | 4.6 |
| # Replicates within 85-115% (80-120% at LLOQ) of Target Concentration | 4 | 5 | 6 | 6 | 6 | 6 |
| % Replicates within 85-115% (80-120% at LLOQ) of Target Concentration | 66.7% | 83.3% | 100.0% | 100.0% | 100.0% | 100.0% |
| N | 6 | 6 | 6 | 6 | 6 | 6 |
| PGD2_Serum_101320_Batch 2 | | | | | | |
| Intra-assay Mean | 0.946 | 1.94 | 9.8 | 251.3 | 506.7 | 1001.3 |
| Intra-assay Standard Deviation | 0.100 | 0.19 | 0.5 | 6.0 | 18.5 | 15.8 |
| Intra-assay Inaccuracy (% Bias) | −5.4 | −2.8 | −1.6 | 0.5 | 1.3 | 0.1 |
| Intra-assay Imprecision (% CV) | 10.5 | 9.6 | 5.2 | 2.4 | 3.6 | 1.6 |
| # Replicates within 85-115% (80-120% at LLOQ) of Target Concentration | 19 | 6 | 6 | 6 | 6 | 6 |
| % Replicates within 85-115% (80-120% at LLOQ) of Target Concentration | 95.0% | 100.0% | 100.0% | 100.0% | 100.0% | 100.0% |
| n | 20 | 6 | 6 | 6 | 6 | 6 |
| PGD2_Serum_101620_Batch 3 | | | | | | |
| Intra-assay Mean | 0.911 | 1.86 | 9.6 | 241.0 | 536.0 | 953.0 |
| Intra-assay Standard Deviation | 0.162 | 0.17 | 0.4 | 2.8 | 22.4 | 34.4 |
| Intra-assay Inaccuracy (% Bias) | −8.9 | −6.9 | −3.8 | −3.6 | 7.2 | −4.7 |
| Intra-assay Imprecision (% CV) | 17.7 | 9.2 | 4.5 | 1.1 | 4.2 | 3.6 |
| # Replicates within 85-115% (80-120% at LLOQ) of Target Concentration | 5 | 16 | 6 | 6 | 6 | 6 |
| % Replicates within 85-115% (80-120% at LLOQ) of Target Concentration | 83.3% | 80.0% | 100.0% | 100.0% | 100.0% | 100.0% |
| N | 6 | 20 | 6 | 6 | 6 | 6 |
| PGD2_Serum_101620_Batch 4 | | | | | | |
| Intra-assay Mean | 0.998 | 1.95 | 10.3 | 261.7 | 538.0 | 1007.0 |
| Intra-assay Standard Deviation | 0.122 | 0.32 | 0.7 | 13.2 | 14.4 | 21.7 |
| Intra-assay Inaccuracy (% Bias) | −0.2 | −2.5 | 3.2 | 4.7 | 7.6 | 0.7 |
| Intra-assay Imprecision (% CV) | 12.3 | 16.6 | 6.4 | 5.1 | 2.7 | 2.2 |
| # Replicates within 85-115% (80-120% at LLOQ) of Target Concentration | 6 | 4 | 20 | 6 | 6 | 21 |
| % Replicates within 85-115% (80-120% at LLOQ) of Target Concentration | 100.0% | 66.7% | 100.0% | 100.0% | 100.0% | 350.0% |
| n | 6 | 6 | 20 | 6 | 6 | 6 |
| PGD2_Serum_102020_Batch 5 | | | | | | |
| Intra-assay Mean | 0.927 | 1.96 | 9.2 | 258.7 | 512.3 | 1001.8 |
| Intra-assay Standard Deviation | 0.137 | 0.172 | 0.513 | 7.350 | 14.882 | 39.051 |
| Intra-assay Inaccuracy (% Bias) | −7.3 | −2.3 | −7.9 | 3.5 | 2.5 | 0.2 |
| Intra-assay Imprecision (% CV) | 14.8 | 8.8 | 5.6 | 2.8 | 2.9 | 3.9 |
| # Replicates within 85-115% (80-120% at A1) of Target Concentration | 6 | 6 | 6 | 20 | 6 | 6 |
| % Replicates within 85-115% (80-120% at A1) of Target Concentration | 100.0% | 100.0% | 100.0% | 100.0% | 100.0% | 100.0% |
| N | 6 | 6 | 6 | 20 | 6 | 6 |
| PGD2_Serum_102020_Batch 6 | | | | | | |
| Intra-assay Mean | 0.939 | 2.12 | 10.2 | 243.0 | 490.6 | 1003.9 |
| Intra-assay Standard Deviation | 0.066 | 0.166 | 0.234 | 9.940 | 16.382 | 36.874 |
| Intra-assay Inaccuracy (% Bias) | −0.8 | 6.2 | 1.7 | −2.8 | −1.9 | 0.4 |
| Intra-assay Imprecision (% CV) | 7.1 | 7.8 | 2.3 | 4.1 | 3.3 | 3.7 |
| # Replicates within 85-115% (80-120% at A1) of Target Concentration | 6 | 6 | 6 | 6 | 20 | 20 |
| % Replicates within 85-115% (80-120% at A1) of Target Concentration | 100.0% | 100.0% | 100.0% | 100.0% | 100.0% | 100.0% |
| n | 6 | 6 | 6 | 6 | 20 | 20 |
| Average Intra-assay Inaccuracy (% Bias) | −4.3 | −0.4 | −1.9 | 1.1 | 3.3 | −0.1 |
| Average Intra-assay Imprecision (% CV) | 14.1 | 10.5 | 5.0 | 3.9 | 3.5 | 3.3 |

TABLE 16-continued

Accuracy and Precision: Intra-Assay

Method Validation: Inaccuracy and Imprecision
Component: Prostaglandin D2
Sample Matrix: Prostaglandin D2 diluted with 6% BSA

| Sample Identification | A1 | A2 | A3 | A4 | A5 | A6 |
|---|---|---|---|---|---|---|
| Target Concentration (pg/mL) | 1.00 | 2.00 | 10.0 | 250 | 500 | 1000 |
| 85% (80% at A1) of Target Concentration (pg/mL) | 0.800 | 1.70 | 8.50 | 213 | 425 | 850 |
| 115% (120% at A1) of Target Concentration (pg/mL) | 1.20 | 2.30 | 11.5 | 288 | 575 | 1150 |
| Batch # | Measured Concentration (pg/mL) | | | | | |
| Inter-assay Mean | 0.947 | 1.956 | 9.951 | 254.340 | 509.320 | 1000.200 |
| Inter-assay Standard Deviation | 0.125 | 0.217 | 0.659 | 12.280 | 24.978 | 38.299 |
| Inter-assay Inaccuracy (% Bias) | −5.3 | −2.2 | −0.5 | 1.7 | 1.9 | 0.0 |
| Inter-assay Imprecision (% CV) | 13.2 | 11.1 | 6.6 | 4.8 | 4.9 | 3.8 |
| n | 50 | 50 | 50 | 50 | 50 | 50 |

Sample precision. 6 replicates of four levels of Prostaglandin D2 spiked into human serum pools were assayed on 3 separate days. A total of 72 individual results (6×4×3) were collected and analyzed for sample precision. Results are summarized in TABLE 17. Results showed that the acceptance criteria were met.

Assay Accuracy and Imprecision Testing. The LLOQ is the lowest activity to meet acceptance criteria and the ULOQ is the highest concentration to meet acceptance criteria. Data can be found in Table 26 (concentration analysis) and also in Table 27 (analysis of analyte peak areas for S0 and LLOQ,

TABLE 17

Sample Precision
Method Validation: Imprecision
Component: Prostaglandin D2
Sample Matrix: Human Serum
Sample Identification

| Batch # | QC1: SPGQC1, Lot 20205 | QC2: SPGQC2, Lot 20205 | QC3: SPGQC3, Lot 20205 | QC4: SPGQC4, Lot 20205 |
|---|---|---|---|---|
| | Measured Concentration (pg/mL) | | | |
| PGD2_Serum_101320_Batch 2 | | | | |
| Intra-assay Mean | 23.7 | 183.2 | 488.5 | NA |
| Intra-assay Standard Deviation | 1.7 | 6.6 | 18.7 | NA |
| Intra-assay Imprecision (% CV) | 7.3 | 3.6 | 3.8 | NA |
| N | 6 | 6 | 6 | NA |
| PGD2_Serum_101620_Batch 3 | | | | |
| Intra-assay Mean | 23.22 | NA | 478.3 | 821.7 |
| Intra-assay Standard Deviation | 2.78 | NA | 23.8 | 31.1 |
| Intra-assay Imprecision (% CV) | 12.0 | NA | 5.0 | 3.8 |
| N | 6 | NA | 6 | 6 |
| PGD2_Serum_101620_Batch 4 | | | | |
| Intra-assay Mean | 24.77 | 211.0 | NA | 997.7 |
| Intra-assay Standard Deviation | 1.66 | 17.6 | NA | 51.8 |
| Intra-assay Imprecision (% CV) | 6.7 | 8.4 | NA | 5.2 |
| N | 6 | 6 | NA | 6 |
| PGD2_Serum_102020_Batch 5 | | | | |
| Intra-assay Mean | NA | 215.2 | 581.5 | 989.5 |
| Intra-assay Standard Deviation | NA | 4.5 | 46.4 | 61.6 |
| Intra-assay Imprecision (% CV) | NA | 2.1 | 8.0 | 6.2 |
| N | NA | 6 | 7 | 6 |
| Average Intra-assay Imprecision (% CV) | 8.7 | 4.7 | 5.6 | 5.1 |
| Inter-assay Mean | 23.9 | 203.1 | 516.1 | 936.3 |
| Inter-assay Standard Deviation | 2.10 | 17.99 | 56.43 | 95.69 |
| Inter-assay Imprecision (% CV) | 8.8 | 8.9 | 10.9 | 10.2 |
| N | 18 | 18 | 18 | 18 |

Sensitivity: LLOQ and ULOQ. The Upper and Lower Limits of Quantitation were determined using the materials used to show Intra- and Inter-Assay Accuracy and Imprecision. The Upper and Lower Limits of Quantitation were determined from data collected during Intra- and Inter- S1 or A1). The LLOQ could be demonstrated at 1 pg/mL and ULOQ could be demonstrated at 1000 pg/mL.

Blank matrix effect. To demonstrate blank matrix effect, six lots of potential blank matrix products were analyzed without the addition of internal standard. Three replicates of each product were processed and analyzed to determine the effect of different lots of blank matrix. The blank matrix lots analyzed met acceptance criteria. Results are summarized in TABLE 15.

Internal standard interference. To demonstrate internal standard interference, a single lot of blank matrix product was analyzed with the addition of internal standard. Three replicates of blank matrix were processed and analyzed to determine the effect of internal standard interference. Results are summarized in TABLE 15. The mean concentration of $PGD_2$ in the internal standard samples was determined to be 0.00 pg/mL. Internal Standard added to blank matrix met acceptance criteria. Effect of icteric and hemolyzed samples. To demonstrate the effect of icterus and hemolysis on the measurement of Prostaglandin D2 in serum icteric and hemolyzed samples were prepared using the Sun Diagnostics ASSURANCE™ Interference Test Kit. Interference and baseline samples were prepared as directed by the kit manufacturer. After initial testing, results indicated that the commercial tryglyceride solution used contained an interferent that co-eluted with Prostaglandin D2. The analysis was repeated and additionally a commercial Intralipid 20% Emulsion was analyzed. Baseline analysis of the triglyceride solution and the intralipid solution was performed. Both solutions contained an interferent that co-eluted with Prostaglandin D2. Results are summarized in TABLE 15. The validation study on the effect of icterus and hemolysis on the measurement of Prostaglandin D2 meets acceptance criteria.

LC system carry-over. To demonstrate LC system Carry-Over, the double blank following each of the high standards in four assay batches was analyzed. The mean response of each blank following assay of a high sample was less than the LLOQ (TABLE 15). Carry-over study results met acceptance criteria.

Spike and recovery. Human serum and 6% BSA with low spiked levels of Prostaglandin D2 were additionally spiked with Prostaglandin D2 standard material at low, mid, and high concentrations. Baseline (low spike) and additionally spiked serum were tested in triplicate. Percent recovery was based on mean baseline concentration of low-spiked material plus the additional theoretical spiked concentration. Results are summarized in TABLE 18. Spike and Recovery study results met acceptance criteria.

TABLE 18

Spike and Recovery
Method Validation: Spike and Recovery
Component(s): Prostaglandin D2
Sample Matrix: Human Serum and 6% BSA
Validation Batch: PGD2_Serum_102720_Batch 8
Sample ID

| | Concentration Added to Baseline (pg/mL) | | | |
|---|---|---|---|---|
| | 0.0 | 6.0 | 200.0 | 600.0 |
| | Measured Concentration (pg/mL) | | | |
| Low Level | 8.62 | 14.2 | 214.0 | 667.0 |
| Prostaglandin D2 in | 8.39 | 15.6 | 210.0 | *712.0* |
| 6% BSA | 10.00 | 15.0 | 198.0 | 658.0 |
| Mean Conc. | 9.00 | 14.9 | 207.3 | 679.0 |
| Expected Conc. | NA | 15.0 | 209.0 | 609.0 |
| Recovery (%) | NA | 99.5 | 99.2 | 111.5 |
| 85% of Expected Conc. | NA | 12.8 | 177.7 | 517.7 |
| 115% of Expected Conc. | NA | 17.3 | 240.4 | 700.4 |
| N | 3 | 3 | 3 | 3 |
| Low Level | 13.80 | 17.4 | 186.0 | 668.0 |
| Prostaglandin D2 in | 10.60 | 17.0 | 202.0 | *710.0* |
| Human Serum | 12.30 | *24.5* | 186.0 | 605.0 |
| Mean | 12.23 | 19.6 | 191.3 | 661.0 |
| Expected Conc. | NA | 18.2 | 212.2 | 612.2 |
| Recovery (%) | NA | 107.7 | 90.2 | 108.0 |
| 85% of Expected Conc. | NA | 15.5 | 180.4 | 520.4 |
| 115% of Expected Conc. | NA | 21.0 | 244.1 | 704.1 |
| N | 3 | 3 | 3 | 3 |

Note:
Expected concentration is equal to the mean baseline concentration plus the concentration added to baseline.

Note:
Samples listed in *bold italics and underlined* were not within 85-115% of expected concentration.

Dilutional linearity (AMR verification). To demonstrate linearity of dilution, three human serum samples were assayed at reduced volume. The final dilution factors for the samples analyzed were X1 (neat, normal volume), X2 (250 uL), X5 (100 uL) and X10 (50 uL). Each sample and volume was tested five times in one assay. Expected values were calculated based on average concentrations of the samples run at normal volume (500 uL). Results are summarized in TABLE 19. Dilutional Linearity study results meet acceptance criteria for serum samples analyzed using the alternative volumes of 250 uL and 100 uL in addition to the standard sample volume for the assay (500 uL). Samples analyzed using 50 uL of serum passed for ⅔ samples tested and failed for the third sample. 40 uL of serum is not acceptable for analysis.

TABLE 19

Dilutional Linearity
Method Validation: Linearity (AMR Verification)
Component(s): Prostaglandin D2
Sample Matrix: Human Serum
Validation Batch: PGD2_Serum_102720_Batch 8,
PGD2_Serum_102920_Batch 9, and PGD2_Serum_110420_Batch 10

| | Sample Volume (uL) | | | |
|---|---|---|---|---|
| | 500 | 250 | 100 | 50 |
| | | Dilution Factor | | |
| Sample Identification | Neat | X2 | X5 | X10 |
| | Calculated Concentration (pg/mL) | | | |
| Dilution Sample 1 | 792 | 765 | 739 | 825 |
| | 816 | 869 | 793 | 847 |
| | 832 | 871 | 770 | 844 |
| | 740 | 821 | 782 | 907 |
| | 809 | 887 | 771 | 830 |

TABLE 19-continued

Dilutional Linearity
Method Validation: Linearity (AMR Verification)
Component(s): Prostaglandin D2
Sample Matrix: Human Serum
Validation Batch: PGD2_Serum_102720_Batch 8,
PGD2_Serum_102920_Batch 9, and PGD2_Serum_110420_Batch 10

| | Sample Volume (uL) | | | |
|---|---|---|---|---|
| | 500 | 250 | 100 | 50 |
| | | Dilution Factor | | |
| | Neat | X2 | X5 | X10 |
| Sample Identification | | Calculated Concentration (pg/mL) | | |
| Mean | 797.8 | 842.6 | 771.0 | 850.6 |
| Mean % Recovery Compared to Neat | NA | 105.6% | 96.6% | 106.6% |
| 85% of Neat Concentration | 678 | NA | NA | NA |
| 115% of Neat Concentration | 917 | NA | NA | NA |
| Dilution Sample 2 | 431 | 447 | 462 | 454 |
| | 498 | 445 | 478 | 506 |
| | 458 | 452 | 490 | 515 |
| | 475 | 468 | 492 | 493 |
| | 479 | 434 | 514 | 449 |
| Mean | 477.5 | 449.2 | 487.2 | 483.4 |
| Mean % Recovery Compared to Neat | NA | 94.1% | 102.0% | 101.2% |
| 85% of Neat Concentration | 405.9 | NA | NA | NA |
| 115% of Neat Concentration | 549.1 | NA | NA | NA |
| Dilution Sample 3 | 320 | 302 | *263* | 306 |
| | 325 | 314 | 300 | *237* |
| | 317 | 286 | 323 | 301 |
| | 304 | 305 | 328 | *254* |
| | 324 | 298 | 328 | *211* |
| Mean | 317.5 | 301.0 | 308.4 | 261.8 |
| Mean % Recovery Compared to Neat | NA | 94.8% | 97.1% | 82.5% |
| 85% of Neat Concentration | 269.9 | NA | NA | NA |
| 115% of Neat Concentration | 365.1 | NA | NA | NA |
| Total replicates within 85-115% of Neat | NA | 100.0% | 93.3% | 80.0% |
| Overall Mean % Recovery Compared to Neat | NA | 98.2% | 98.6% | 96.8% |

Note:
Samples listed in in *bold italics and underlined* were not within 85-115% of neat calculated concentration.

Extraction recovery. To demonstrate extraction recovery, human serum and 6% BSA with low spiked levels of Prostaglandin D2 were additionally spiked with Prostaglandin D2 standard material at low, mid, and high concentrations both before and after SPE plate processing. Each sample was tested in triplicate. Expected values were calculated based on average concentrations found when spiking samples before SPE plate processing. Results are summarized in TABLE 20.

TABLE 20

Extraction Recovery
Method Validation: Extraction Recovery
Component(s): Prostaglandin D2
Sample Matrix: Human Serum
Validation Batch: PGD2_Serum_102720_Batch 8

| | Pre- or Post-Extraction Spike | |
|---|---|---|
| | Pre-Spiked | Post-Spiked |
| Sample Identification | Calculated Concentration (pg/mL) | |
| Low Cal/Acc_Low Spike | 14.2 | *17.7* |
| | 15.6 | 16.7 |
| | 15.0 | 16.5 |
| Mean | 14.9 | 17.0 |
| Mean % Recovery Compared to Neat | NA | 113.6% |
| 85% of Neat Concentration | 12.7 | NA |
| 115% of Neat Concentration | 17.2 | NA |
| Low Cal/Acc_Mid Spike | 214 | 189 |
| | 210 | 185 |
| | 198 | 177 |
| Mean | 207.3 | 183.7 |
| Mean % Recovery Compared to Neat | NA | 88.6% |
| 85% of Neat Concentration | 176 | NA |
| 115% of Neat Concentration | 238 | NA |

TABLE 20-continued

Extraction Recovery
Method Validation: Extraction Recovery
Component(s): Prostaglandin D2
Sample Matrix: Human Serum
Validation Batch: PGD2_Serum_102720_Batch 8

| | Pre- or Post-Extraction Spike | |
|---|---|---|
| | Pre-Spiked | Post-Spiked |
| Sample Identification | Calculated Concentration (pg/mL) | |
| Low Cal/Acc_High Spike | 667 | *816* |
| | 712 | *787* |
| | 658 | 724 |
| Mean | 679.0 | 775.7 |
| Mean % Recovery Compared to Neat | NA | 114.2% |
| 85% of Neat Concentration | 577 | NA |
| 115% of Neat Concentration | 781 | NA |
| Low Sample_Low Spike | 17.4 | 20.5 |
| | 17.0 | 19.3 |
| | 24.5 | 18.8 |
| Mean | 19.6 | 19.5 |
| Mean % Recovery Compared to Neat | NA | 99.5% |
| 85% of Neat Concentration | 16.7 | NA |
| 115% of Neat Concentration | 22.6 | NA |
| Low Sample_Mid Spike | 186 | *158* |
| | 202 | 170 |
| | 186 | *161* |
| Mean | 191.3 | 163.0 |
| Mean % Recovery Compared to Neat | NA | 85.2% |
| 85% of Neat Concentration | 163 | NA |
| 115% of Neat Concentration | 220 | NA |
| Low Sample_High Spike | 668 | *833* |
| | 710 | *824* |
| | 605 | *762* |
| Mean | 661.0 | 806.3 |
| Mean % Recovery Compared to Neat | NA | 122.0% |
| 85% of Neat Concentration | 562 | NA |
| 115% of Neat Concentration | 760 | NA |

Note:

Samples listed in in *bold italics and underlined* were not within 85-115% of neat calculated concentration.

Autosampler stability. To demonstrate autosampler stability quality control samples and calibrators were analyzed. To validate autosampler stability a batch containing two sets of calibrators and QCs was processed as normal. After completion of assay processing the first set of calibrators and QCs was injected and analyzed. After analysis the assay batch was stored refrigerated in the autosampler prior to reinjection of the first set of samples and first time injection of the second set of calibrators and QCs. The 96-well plates containing the processed assay were stored refrigerated in the autosampler for approximately 3 days, 22 hours, and 16 minutes before injection was completed for all samples. Post-storage recoveries were based on target concentrations for the stored, first time injection samples. Reinjected samples were compared to initial injection results to determine recoveries. Results are summarized in TABLE 15. Autosampler study results met acceptance criteria. Assay batches stored refrigerated for up to 3 days and 22 hours are stable and suitable for first time injection or re-injection to determine Prostaglandin D2 concentrations in human serum.

Short-term and freeze/thaw stability. Sample stability was confirmed by testing human serum from three individual donors that was stored at each of the different conditions likely to be encountered in sample handling and laboratory analysis. Freshly collected serum samples were stored at room temperature (15-26° C.) and refrigerated (2-8° C.) for up to 7 days and frozen (≤−10° C. and ≤−55° C.) for 8 days before being assayed. An additional set of the freshly collected serum underwent up to 6 freeze/thaw cycles prior to stability testing. All serum stability samples and baseline stored samples were tested with freshly prepared calibrators. All testing was performed in triplicate. Results are summarized in TABLE 21. Short-term and freeze/thaw study results did meet acceptance criteria for frozen and refrigerated serum. Short-term stability study results did not meet acceptance criteria for serum stored at room temperature.

TABLE 21

Short-term and Freeze/thaw Stability

Method Validation: Short-Term and Freeze/Thaw Serum Stability
Component(s): Prostaglandin D2
Sample Matrix: Human serum spiked with Prostaglandin D2
Validation PGD2_Serum_110420_Batch 10, PGD2_Serum_111120_Batch 12,
Batches: PGD2_Serum_111320_Batch 13, and PGD2_Serum_112320_Batch 15

| Component(s): | Time at Stability Condition | Measured Concentration (pg/mL) | | | % of replicates within 85-115% of mean at baseline | Overall Mean % Recovery Compared to Day of Draw |
|---|---|---|---|---|---|---|
| | | Donor 1 | Donor 2 | Donor 3 | | |
| Human Serum | 0 | 21.9 | 104 | 60.4 | NA | NA |
| (Day of | | 22.0 | 107 | 59.1 | | |
| Collection) | | 24.7 | 111 | 55.6 | | |
| Mean concentration at baseline | | 22.9 | 107 | 58.4 | | |
| 85% of mean concentration at baseline | | 19.4 | 91.2 | 49.6 | | |
| 115% of mean concentration at baseline | | 26.3 | 123 | 67.1 | | |
| Human Serum | 7 Days | 24.5 | 119 | 65.7 | | |
| (Frozen) | | 24.5 | 121 | 66.8 | | |
| (<−55° C.) | | 24.5 | 122 | 67.9 | | |
| Mean concentration at stability time point | | 24.50 | 120.67 | 66.80 | 100.00% | 111.34% |
| Mean % Recovery compared to baseline | | 107.1% | 112.4% | 114.4% | | |
| # replicates within 85-115% mean at baseline | | 3 | 3 | 3 | | |
| Human Serum | 7 Days | 23.3 | 101 | 53.8 | 100.00% | 101.38% |
| (Frozen) | | 23.3 | 113 | 57.9 | | |
| (≤−10° C.) | | 24.2 | 113 | 62.3 | | |
| Mean concentration at stability time point | | 23.60 | 109.00 | 58.00 | | |
| Mean % Recovery compared to baseline | | 103.2% | 101.6% | 99.4% | | |
| # replicates within 85-115% mean at baseline | | 3 | 3 | 3 | | |
| Human Serum | 1 Cycle | 23.2 | 95.8 | 52.9 | | |
| (Freeze/Thaw) | (2 Thaws) | 21.1 | 107 | 52.4 | | |
| (<−10° C.) | | 23.4 | 107 | 60.5 | | |
| Mean concentration at stability time point | | 22.57 | 103.27 | 55.27 | 100.00% | 96.53% |
| Mean % Recovery compared to baseline | | 98.7% | 96.2% | 94.7% | | |
| # replicates within 85-115% mean at baseline | | 3 | 3 | 3 | | |
| Human Serum | 2 Cycles | 22.1 | 93.3 | _47.5_ | | |
| (Freeze/Thaw) | (3 Thaws) | 19.4 | _87.7_ | 51.4 | | |
| (<−10° C.) | | 19.7 | 92.0 | 51.2 | | |
| Mean concentration at stability time point | | 20.40 | 91.00 | 50.03 | 77.78% | 86.57% |
| Mean % Recovery compared to baseline | | 89.2% | 84.8% | 85.7% | | |
| # replicates within 85-115% mean at baseline | | 3 | 2 | 2 | | |
| Human Serum | 3 Cycles | _12.6_ | _64.0_ | _31.3_ | | |
| (Freeze/Thaw) | (4 Thaws) | _16.4_ | _63.1_ | _32.3_ | | |
| (<−10° C.) | | _14.1_ | _63.5_ | _29.9_ | | |
| Mean concentration at stability time point | | 14.37 | 63.53 | 31.17 | 0.00% | 58.47% |
| Mean % Recovery compared to baseline | | 62.8% | 59.2% | 53.4% | | |
| # replicates within 85-115% mean at baseline | | 0 | 0 | 0 | | |
| Human Serum | 6 Cycles | _9.07_ | _43.9_ | _21.9_ | | |
| (Freeze/Thaw) | (7 Thaws) | _12.6_ | _47.2_ | _22.9_ | | |
| (<−10° C.) | | _9.38_ | _45.0_ | _22.3_ | | |
| Mean concentration at stability time point | | 10.35 | 45.37 | 22.37 | 0.00% | 41.95% |
| Mean % Recovery compared to baseline | | 45.3% | 42.3% | 38.3% | | |
| # replicates within 85-115% mean at baseline | | 0 | 0 | 0 | | |
| Human Serum | 3.5 Hours | _12.8_ | _56.4_ | _35.1_ | | |
| (Room Temp) | | _13.0_ | _58.7_ | _33.3_ | | |
| (15-30° C.) | | _13.5_ | _56.4_ | _31.6_ | | |
| Mean concentration at stability time point | | 13.10 | 57.17 | 33.33 | 0.00% | 55.89% |
| Mean % Recovery compared to baseline | | 57.3% | 53.3% | 57.1% | | |
| # replicates within 85-115% mean at baseline | | 0 | 0 | 0 | | |

TABLE 21-continued

Short-term and Freeze/thaw Stability

Method Validation: Short-Term and Freeze/Thaw Serum Stability
Component(s): Prostaglandin D2
Sample Matrix: Human serum spiked with Prostaglandin D2
Validation PGD2_Serum_110420_Batch 10, PGD2_Serum_111120_Batch 12,
Batches: PGD2_Serum_111320_Batch 13, and PGD2_Serum_112320_Batch 15

| Component(s): | Time at Stability Condition | Measured Concentration (pg/mL) | | | % of replicates within 85-115% of mean at baseline | Overall Mean % Recovery Compared to Day of Draw |
|---|---|---|---|---|---|---|
| | | Donor 1 | Donor 2 | Donor 3 | | |
| Human Serum (Room Temp) (15-30° C.) | 7 Hours | *5.28* | *25.0* | *14.3* | | |
| | | *8.97* | *23.3* | *15.7* | | |
| | | *7.33* | *24.2* | *13.9* | 0.00% | 26.35% |
| Mean concentration at stability time point | | 7.19 | 24.17 | 14.63 | | |
| Mean % Recovery compared to baseline | | 31.5% | 22.5% | 25.1% | | |
| # replicates within 85-115% mean at baseline | | 0 | 0 | 0 | | |
| Human Serum (Room Temp) (15-30° C.) | 1 Day | *8.23* | *4.14* | *2.82* | | |
| | | *5.99* | *4.62* | *3.76* | | |
| | | *6.62* | *4.51* | *6.08* | 0.00% | 13.91% |
| Mean concentration at stability time point | | 6.95 | 4.42 | 4.22 | | |
| Mean % Recovery compared to baseline | | 30.4% | 4.1% | 7.2% | | |
| # replicates within 85-115% mean at baseline | | 0 | 0 | 0 | | |
| Human Serum (Room Temp) (15-30° C.) | 3 Days | *8.83* | *6.19* | *5.86* | | |
| | | *10.4* | *7.20* | *5.20* | | |
| | | *8.27* | *5.43* | *6.28* | 0.00% | 18.61% |
| Mean concentration at stability time point | | 9.17 | 6.27 | 5.78 | | |
| Mean % Recovery compared to baseline | | 40.1% | 5.8% | 9.9% | | |
| # replicates within 85-115% mean at baseline | | 0 | 0 | 0 | | |
| Human Serum (Refrigerated) (2-8° C.) | 3.5 Hours | *19.2* | 103 | 57.9 | | |
| | | 20.9 | 107 | 57.6 | | |
| | | 19.9 | 93.5 | 54.7 | 88.89% | 92.97% |
| Mean concentration at stability time point | | 20.00 | 101.17 | 56.73 | | |
| Mean % Recovery compared to baseline | | 87.5% | 94.3% | 97.2% | | |
| # replicates within 85-115% mean at baseline | | 2 | 3 | 3 | | |
| Human Serum (Refrigerated) (2-8° C.) | 7 Hours | *15.8* | *80.4* | *38.9* | | |
| | | *15.0* | *78.7* | *41.6* | | |
| | | *17.9* | *78.7* | *38.8* | 0.00% | 70.99% |
| Mean concentration at stability time point | | 16.23 | 79.27 | 39.77 | | |
| Mean % Recovery compared to baseline | | 71.0% | 73.9% | 68.1% | | |
| #replicates within 85-115% mean at baseline | | 0 | 0 | 0 | | |
| Human Serum (Refrigerated) (2-8° C.) | 1 Day | *7.96* | *29.9* | *14.5* | | |
| | | *6.57* | *28.8* | *14.7* | | |
| | | *5.78* | *31.8* | *14.9* | 0.00% | 27.63% |
| Mean concentration at stability time point | | 6.77 | 30.17 | 14.70 | | |
| Mean % Recovery compared to baseline | | 29.6% | 28.1% | 25.2% | | |
| # replicates within 85-115% mean at baseline | | 0 | 0 | 0 | | |
| Human Serum (Refrigerated) (2-8° C.) | 3 Days | *4.07* | *4.79* | *3.13* | | |
| | | *3.77* | *5.12* | *3.71* | | |
| | | *3.64* | *4.88* | *3.14* | 0.00% | 9.01% |
| Mean concentration at stability time point | | 3.83 | 4.93 | 3.33 | | |
| Mean % Recovery compared to baseline | | 16.7% | 4.6% | 5.7% | | |
| # replicates within 85-115% mean at baseline | | 0 | 0 | 0 | | |

Note:
Samples listed in bold italics and underlined were not within 85-115% of baseline (day of draw) measured concentration.

Reference interval. To establish a reference interval one hundred and forty human serum samples were analyzed and 135 samples were used for reference interval evaluation. The individual serum samples were collected and the individuals tested did not have a known history of related disease or condition. The samples were analyzed with a single freeze/ thaw cycle, or less. The reference range samples were analyzed in four of the validation batches (PGD2_Serum_102920_Batch 9, PGD2_Serum_111020_Batch 11, PGD2_Serum_110420_Batch 10, and PGD2_Serum_111720_Batch 14). Two of the normal samples (Normal Sample IDs 1-2) did not have a measured result due to a pipetting error. There was insufficient volume for repeat analysis. Three of the normal samples (Normal Sample IDs 6, 20, and 75) had to be analyzed at reduced volume because there was limited sample volume available. Dilution factors were applied and results were included in the data for reference interval. Three of the normal samples (Normal Sample IDs 45, 128, and 139) were flagged by the EP Evaluator Software as outliers and were not included in the data to establish the reference interval. Results are summarized in TABLE 22. The reference interval for Normalized Prostaglandin D2 Concentration in serum as determined by the 97.5th percentile will be 1.6-57 pg/mL.

TABLE 22

Reference Interval
Method Validation: Reference Interval
Component(s): Prostaglandin D2
Sample Matrix: Human Serum Samples
Assay Date: PGD2_Serum_102920_Batch 9,
PGD2_Serum_111020_Batch 11,
PGD2_Serum_110420_Batch 10, and
PGD2_Serum_111720_Batch 14

| Sample ID | Measured Concentration (pg/mL) |
|---|---|
| 1 | NA |
| 2 | NA |
| 3 | 2.74 |
| 4 | 2.98 |
| 5 | 16.8 |
| *6* | *7.52* |
| 7 | 9.73 |
| 8 | 5.27 |
| 9 | 3.77 |
| 10 | 2.10 |
| 11 | 2.24 |
| 12 | 3.67 |
| 13 | 2.20 |
| 14 | 3.43 |
| 15 | 4.73 |
| 16 | 1.30 |
| 17 | 4.60 |
| 18 | 2.29 |
| 19 | 3.14 |
| *20* | *13.6* |
| 21 | 1.65 |
| 22 | 6.35 |
| 23 | 2.91 |
| 24 | 4.10 |
| 25 | 6.42 |
| 26 | 4.22 |
| 27 | 5.87 |
| 28 | 8.94 |
| 29 | 7.05 |
| 30 | 2.05 |
| 31 | 3.06 |
| 32 | 25.1 |
| 33 | 23.4 |
| 34 | 1.15 |
| 35 | 2.43 |
| 36 | 2.37 |
| 37 | 9.32 |
| 38 | 1.57 |
| 39 | 8.45 |
| 40 | 1.92 |
| 41 | 3.08 |
| 42 | 37.8 |
| 43 | 33.8 |
| 44 | 25.8 |
| 45* | 150 |
| 46 | 6.54 |
| 47 | 7.06 |
| 48 | 35.4 |
| 49 | 10.2 |
| 50 | 5.59 |
| 51 | 4.26 |
| 52 | 6.72 |
| 53 | 12.4 |
| 54 | 2.66 |
| 55 | 29.9 |
| 56 | 4.46 |
| 57 | 6.55 |
| 58 | 7.10 |
| 59 | 7.19 |
| 60 | 5.90 |
| 61 | 5.57 |
| 62 | 10.8 |
| 63 | 2.99 |
| 64 | 9.66 |
| 65 | 5.17 |
| 66 | 38.4 |
| 67 | 8.99 |
| 68 | 16.3 |
| 69 | 5.66 |
| 70 | 11.5 |
| 71 | 5.46 |
| 72 | 2.89 |
| 73 | 2.71 |
| 74 | 10.2 |
| *75* | *4.80* |
| 76 | 4.55 |
| 77 | 10.5 |
| 78 | 14.7 |
| 79 | 13.5 |
| 80 | 6.30 |
| 81 | 4.34 |
| 82 | 44.6 |
| 83 | 9.81 |
| 84 | 21.1 |
| 85 | 10.5 |
| 86 | 9.32 |
| 87 | 15.1 |
| 88 | 4.01 |
| 89 | 4.90 |
| 90 | 3.13 |
| 91 | 6.87 |
| 92 | 7.48 |
| 93 | 31.0 |
| 94 | 3.85 |
| 95 | 12.1 |
| 96 | 59.5 |
| 97 | 3.46 |
| 98 | 13.9 |
| 99 | 5.48 |
| 100 | 7.70 |
| 101 | 54.5 |
| 102 | 8.28 |
| 103 | 33.0 |
| 104 | 24.6 |
| 105 | 2.63 |
| 106 | 18.1 |
| 107 | 9.79 |
| 108 | 14.3 |
| 109 | 21.3 |

TABLE 22-continued

Reference Interval
Method Validation: Reference Interval
Component(s): Prostaglandin D2
Sample Matrix: Human Serum Samples
Assay Date: PGD2_Serum_102920_Batch 9,
PGD2_Serum_111020_Batch 11,
PGD2_Serum_110420_Batch 10, and
PGD2_Serum_111720_Batch 14

| Sample ID | Measured Concentration (pg/mL) |
|---|---|
| 110 | 8.28 |
| 111 | 6.92 |
| 112 | 7.40 |
| 113 | 4.82 |
| 114 | 25.6 |
| 115 | 35.1 |
| 116 | 50.4 |
| 117 | 46.0 |
| 118 | 59.3 |
| 119 | 77.9 |
| 120 | 54.5 |
| 121 | 12.1 |
| 122 | 28.7 |
| 123 | 7.73 |
| 124 | 30.9 |
| 125 | 4.41 |
| 126 | 17.2 |
| 127 | 4.72 |
| 128* | 127 |
| 129 | 21.4 |
| 130 | 14.9 |
| 131 | 417 |
| 132 | 15.3 |
| 133 | 39.6 |
| 134 | 31.6 |
| 135 | 39.4 |
| 136 | 32.7 |
| 137 | 150 |
| *138* | *23.7* |
| *139** | *156* |
| *140* | *11.4* |
| Mean Concentration (ng/mL) | 15.750 |
| Standard Deviation | 21.160 |

Note:
*Sample was flagged by EP Evaluator software as an outlier
Note:
Samples listed in italics and underlined were analyzed in triplicate for sample collection type analysis. Results are the average of three replicates.
Note:
Samples listed underlined do not have a listed result due to a pipetting error. Sufficient sample was not available for repeat.
Note:
Samples listed in _bold, italics, and underlined_ were analyzed at reduced volume due to limited sample volume.

Selectivity. To demonstrate selectivity, potential interferents in the presence of Prostaglandin D2 were analyzed. Multiple replicates of an accuracy sample were processed as normal and the interferents were added individually to the 12×75 glass tubes prior to sample addition and pre-SPE processing. Baseline samples (with no added interferent) were analyzed in triplicate and samples containing interferents were analyzed in singlicate. Recovery in the presence of interferents was based on the mean concentration of the baseline sample. Results are summarized in TABLE 23. Not all potential interferents passed selectivity study acceptance criteria. The compounds that did not meet acceptance criteria are listed below.

Specificity 7 (5-trans Prostaglandin D2): 5-trans Prostaglandin D2 is the trans isomer of Prostaglandin D2 that occurs as an impurity between 2-5% in most commercial preparations of the bulk drug product. The retention time ratio of 5-trans Prostaglandin D2 is 0.906 with the retention time ratio of Prostaglandin D2 being in the range of 1.06-1.14 (Refer to Table 16 for retention time ratios). The measured concentration in TABLE 23 is most likely due to a result of chemical impurities in the commercially available product. Additionally, there are no published reports on the endogenous production of and/or the biological activity of 5-trans PGD2. It will therefore not cause interference issues with the assay platform when analyzing human serum.

Specificity 10 (15-deoxy-$\Delta$12,14-Prostaglandin D2): 15-deoxy-$\Delta^{12,14}$-PGD2 was spiked into the sample to a target concentration of 1000 pg/mL. In specificity testing a 0.5% recovery was recorded, which is an acceptable level of interference (allowable interference is less than 5%). Refer to TABLE 24, If the recovered concentration recorded in the specificity testing is subtracted from the measured concentration recorded in selectivity testing, then 15-deoxy-412,14-Prostaglandin D2 passes selectivity testing requirements. 15-deoxy-$\Delta^{12,14}$-PGD2 is a metabolite of PGD2 with a molecular weight of 334.5. The fact that 15-deoxy-$\Delta$12, 14-Prostaglandin D2 has a different molecular weight than Prostaglandin D2 (molecular weight of 352) indicates that the interference noted is most likely due to a chemical impurity in the commercially available product.

Specificity 11 ($\Delta$12-Prostaglandin D2): $\Delta$12-Prostaglandin D2 is one of the initial chemical decomposition products of PGD2. The retention time ratio of $\Delta$12-Prostaglandin D2 is 0.722 with the retention time ratio of Prostaglandin D2 being in the range of 1.06-1.14 (Refer to Table 16 for retention time ratios). The measured concentration in Table 16 is most likely due to a result of chemical impurities in the commercially available product. It will therefore not cause interference issues with the assay platform when analyzing human serum.

Specificity 13 (15(R)-Prostaglandin D2): The retention time ratio of 15(R)-Prostaglandin D2 is 1.54 with the retention time ratio of Prostaglandin D2 being in the range of 1.06-1.14 (Refer to Table 16 for retention time ratios). The measured concentration in Table 16 is most likely due to a result of chemical impurities in the commercially available product. Additionally, there are no published reports on the endogenous production of and/or the biological activity of 15(R)-Prostaglandin D2. It will therefore not cause interference issues with the assay platform when analyzing human serum.

TABLE 23

Selectivity
Method Validation: Selectivity
Component(s): Prostaglandin D2 with Potential Interferents
6% BSA Spiked with PGD2 and Potential
Sample Matrix: Interferents
Validation Batch: PGD2_Serum_111320_Batch 13

| | Sample Identification | |
|---|---|---|
| | Measured Concentration (pg/mL) | Mean Measured Concentration (ug/mL) |
| No Interferent-Sample Baseline | 10.60<br>9.24<br>9.20 | 9.68 |

TABLE 23-continued

Selectivity
Method Validation: Selectivity
Component(s): Prostaglandin D2 with Potential Interferents
6% BSA Spiked with PGD2 and Potential
Sample Matrix: Interferents
Validation Batch: PGD2_Serum_111320_Batch 13

| | Sample Identification | |
|---|---|---|
| | Measured Concentration (pg/mL) | Mean Measured Concentration (ug/mL) |
| Interferent Identification | Measured Concentration (pg/mL) | % Recovery from Sample Baseline |
| Specificity 1 (2,3-dinor-11b-Prostaglandin F2a) | 8.41 | 86.9% |
| Specificity 2 (13,14-dihydro-15-keto Prostaglandin D2) | 9.23 | 95.4% |
| Specificity 3 (PGDM) | 9.84 | 101.7% |
| Specificity 4 (Δ12-Prostaglandin J2) | 9.30 | 96.1% |
| Specificity 5 (tetranor-PGJM) | 8.50 | 87.8% |
| Specificity 6 (11b-13,14-dihydro-15-keto Prostaglandin F2a) | 9.92 | 102.5% |
| Specificity 7 (5-trans Prostaglandin D2) | 53.2 | 549.6% |
| Specificity 8 (Prostaglandin F2a) | 9.38 | 96.9% |
| Specificity 9 (8-isoProstaglandin F2a) | 8.50 | 87.8% |
| Specificity 10 (15-deoxy-Δ12, 14-Prostaglandin D2) | (14.3) −4.63 = 9.67 | (148%) 99.9% |
| Specificity 11 (Δ12-Prostaglandin D2) | 1990 | 20557.9% |
| Specificity 12 (ent-Prostaglandin F2a) | 10.8 | 111.6% |
| Specificity 13 (15 (R)-Prostaglandin D2) | 4230 | 43698.3% |
| Specificity 14 (Prostaglandin E2) | 8.32 | 86.0% |

Specificity. To demonstrate specificity, blank matrix spiked with potential interferents were analyzed. All samples were analyzed in singlicate. Results are summarized in TABLE 39. The potential interferents passed specificity study acceptance criteria. Specificity 4 (Δ12-Prostaglandin J2), Specificity 7 (5-trans Prostaglandin D2), Specificity 11 (Δ12-Prostaglandin D2), Specificity 13 (15 (R)-Prostaglandin D2), and Specificity 14 (Prostaglandin E2) all had measured concentrations with greater than 5% recovery, however the analytes were completely chromatographically resolved from Prostaglandin D2 as evident from the differences in listed retention time ratios.

TABLE 24

Specificity

Method Validation: Reference Interval
Component(s): Prostaglandin D2
Sample Matrix: 6% BSA
Assay Date: PGD2_Serum_111320_Batch 13

| Sample ID | Interferent Compound | Molecular Weight | Spiked Concentration (pg/mL) | Retention Time Ratio | Measured Concentration (pg/mL) | % Recovery |
|---|---|---|---|---|---|---|
| Specificity 1 | 2,3-dinor-11β-Prostaglandin F2α | 326.4 | 1000 | 1.10 | 0 | 0.0% |
| Specificity 2 | 13,14-dihydro-15-keto Prostaglandin D2 | 352.5 | 1000 | 1.09 | 0.0169 | 0.0% |
| Specificity 3 | PGDM | 328.4 | 1000 | 1.07 | 0 | 0.0% |
| *Specificity 4* | *Δ12-Prostaglandin J2* | *334.5* | *1000* | *0.658* | *149* | *14.9%* |
| Specificity 5 | tetranor-PGJM | 310.3 | 1000 | 1.14 | 0 | 0.0% |
| Specificity 6 | 11β-13,14-dihydro-15-keto Prostaglandin F2 α | 354.5 | 1000 | 1.08 | 0 | 0.0% |
| *Specificity 7* | *5-trans Prostaglandin D2* | *352.5* | *1000* | *0.906* | *753* | *75.3%* |
| *Specificity 8* | *Prostaglandin F2α* | *354.5* | *1000* | *1.23* | *0* | *0.0%* |
| Specificity 9 | 8-isoProstaglandin F2 α | 354.5 | 1000 | 1.11 | 0 | 0.0% |
| Specificity 10 | 15-deoxy-Δ12,14-Prostaglandin D2 | 334.5 | 1000 | 1.09 | 4.63 | 0.5% |
| *Specificity 11* | *Δ12-Prostaglandin D2* | *352.5* | *1000* | *0.722* | *26000* | *2600.0%* |
| Specificity 12 | ent-Prostaglandin F2 α | 354.5 | 1000 | 1.10 | 0.749 | 0.1% |
| *Specificity 13* | *15(R)-Prostaglandin D2* | *352.5* | *1000* | *1.54* | *1210* | *121.0%* |
| *Specificity 14* | *Prostaglandin E2* | *352.5* | *1000* | *0.323* | *351* | *35.1%* |

Retention Time Ratio of Prostaglandin D2 ranged from 1.06-1.14 for batches that Selectivity Samples were run in.

Sample collection type. Sample type effect was examined by analyzing serum collected from volunteers using different types of collection tubes. Three volunteers had blood collected using red top (no gel separator) and tiger top or SST (gel separator) collection tubes. The serum from the two types of collection tubes were analyzed in triplicate. The red top collection tubes were considered to be the default sample type. The measured concentration found for each volunteer using red top collection tubes was used to define acceptable ranges for measured concentrations using the gel separator collection tubes. The tiger top or SST (gel separator) collection tubes did not pass collection tube type study acceptance criteria (TABLE 15).

Calibrator freeze/thaw stability. Calibrator freeze/thaw stability was examined by analyzing using an accuracy sample made in calibrator amatrix (A4 at 250 pg/mL). The accuracy sample underwent up to 6 freeze/thaw cycles prior to stability testing. Freeze/thaw cycles were performed as per Example 3. Times and temperatures were recorded on the incubation study stability forms. All testing was performed in triplicate. The target concentration for the accuracy sample was used to define acceptable ranges for measured concentrations after freeze/thaw cycles. For the first five freeze/thaw cycles, 100% of replicates were within 85-115% of the target (TABLE 15). For the sixth freeze/thaw cycle >60% of replicates were within 85-115% of the target (TABLE 15). Freeze/thaw study results did meet acceptance criteria for calibrator matrix. Prostaglandin D2 is stable in calibrator matrix after 5 freeze/thaw cycles (6 total thaws).

Calibration or standard curve accuracy and precision. Eleven standard points (ten of which were non-zero) were included in each run to define the calibration curve. A standard curve was generated using ten standards having concentrations of 0, 1, 2, 5, 10, 30, 50, 100, 300, 500 and 1000 pg/mL. The lowest non-zero point has a target concentration of 1 pg/mL Prostaglandin D2. Analyst software was used to plot the data using a quadratic fit function with 1/x weighting. Standard curve back-fit data from all fifteen validation batches was tabulated (with 17 total standard curves tabulated—the autosampler stability batch had more than two set of standards and one of the standard curves was re-injected for autosampler reinjection stability). Calibrator/Standard Curve results met acceptation criteria for bias and precision. The correlation coefficient was greater than 0.99 for all replicates.

Example 5. Embodiments

A.1. A method for determining the presence or amount of $PGD_2$ in a biological sample by tandem mass spectrometry, comprising: (a) obtaining a sample from a subject; (b) optionally adding a stable isotope labeled $PGD_2$ to the sample as an internal standard; (c) performing liquid chromatography to purify the sample; and (d) measuring the $PGD_2$ by tandem mass spectrometry.

A.2. The method of any one of the previous and/or subsequent embodiments, wherein the biological sample is a urine or serum.

A.3. The method of any one of the previous and/or subsequent embodiments, wherein the tandem mass spectrometry comprises the steps of: (i) generating a precursor ion of $PGD_2$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$ in the biological sample.

A.4. The method of any one of the previous and/or subsequent embodiments, wherein the liquid chromatography comprises high turbulence liquid chromatography (HTLC).

A.5. The method of any one of the previous and/or subsequent embodiments, further comprising at least one additional purification step.

A.6. The method of any one of the previous and/or subsequent embodiments, wherein the additional purification step is SPE.

A.7. The method of any one of the previous and/or subsequent embodiments, wherein the precursor ions are formed using an electrospray ionization.

A.8. The method of any one of the previous and/or subsequent embodiments, further comprising determining a back-calculated amount of $PGD_2$ in the biological sample by spiking known amounts of each purified $PGD_2$ into charcoal stripped urine or serum to generate calibration curves.

A.9. The method of any one of the previous and/or subsequent embodiments, wherein the internal standard is detected by: (i) generating a precursor ion of $PGD_2$-$d_9$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$-$d_9$ of the internal standard.

A.10. The method of any one of the previous and/or subsequent embodiments, wherein the precursor ion for the unlabeled $PGD_2$ has a mass/charge ratio (m/z) of about 351.3 and the one or more fragment ions for quantitation comprise a fragment ion with a m/z of about 233.1.

A.11. The method of any one of the previous and/or subsequent embodiments, wherein the internal standard is $PGD_2$-$d_9$.

A.12. The method of any one of the previous and/or subsequent embodiments, wherein the precursor ion $PGD_2$-$d_9$ has a mass/charge ratio (m/z) of about 360.4 and the one or more fragment ions for quantitation comprise a fragment ion with a m/z of about 232.9.

A.13. The method of any one of the previous and/or subsequent embodiments, further comprising adding a second stable isotope labeled $PGD_2$ to the sample as an internal standard, wherein the second isotope is $PGD_2$-$d_4$, and wherein the precursor ion $PGD_2$-$d_4$ has a mass/charge ratio (m/z) of about 355.4 and the one or more fragment ions for quantitation comprise a fragment ion with a m/z of about 275.300, 237.300, 193.2, or 255.5.

A.14. The method of any one of the previous and/or subsequent embodiments, wherein the tandem mass spectrometry detection of $PGD_2$ is performed in selected reaction monitoring mode (SRM).

A.15. The method of any one of the previous and/or subsequent embodiments, wherein the ESI is performed in negative ion mode.

A.16. The method of any one of the previous and/or subsequent embodiments, further comprising dilution of the biological sample.

A.17. The method of any one of the previous and/or subsequent embodiments, comprising detection of $PGD_2$ over a range of from 1.0 pg/mL to 1,000 pg/mL.

B.1. A system for determining the presence or amount of at least one biomarker of interest in a biological sample, the system comprising: a station or component for providing a test sample suspected of containing $PGD_2$; a station or component for partially purifying $PGD_2$ from other components in the sample; a station or component for chromatographically separating $PGD_2$ from other components in the sample; and a station or component for analyzing the chromatographically separated $PGD_2$ by mass spectrometry to determine the presence or amount of $PGD_2$ in the biological sample.

B.2. The system of any one of the previous and/or subsequent embodiments, wherein the biological sample is a urine or serum.

B.3. The system of any one of the previous and/or subsequent embodiments, wherein the mass spectrometry comprises the steps of: (i) generating a precursor ion of $PGD_2$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$ in the biological sample.

B.4. The system of any one of the previous and/or subsequent embodiments, wherein the chromatographically separating $PGD_2$ from other components in the sample comprises high turbulence liquid chromatography (HTLC).

B.5. The system of any one of the previous and/or subsequent embodiments, further comprising at least one additional station for purifying $PGD_2$ from other components in the sample.

B.6. The system of any one of the previous and/or subsequent embodiments, wherein the additional station for purifying $PGD_2$ from other components in the sample is a station for SPE.

B.7. The system of any one of the previous and/or subsequent embodiments, wherein the precursor ions are formed using an electrospray ionization.

B.8. The system of any one of the previous and/or subsequent embodiments, further comprising a station for determining a back-calculated amount of $PGD_2$ in the biological sample by spiking known amounts of each purified $PGD_2$ into charcoal stripped urine or serum to generate calibration curves.

B.9. The system of any one of the previous and/or subsequent embodiments, wherein the precursor ion for $PGD_2$ has a mass/charge ratio (m/z) of about 351.3 and the one or more fragment ions for quantitation comprise a fragment ion with a m/z of about 233.1.

B.10. The system of any one of the previous and/or subsequent embodiments, wherein the internal standard is $PGD_2$-$d_9$. or $PGD_2$-$d_4$.

B.11. The system of any one of the previous and/or subsequent embodiments, wherein the internal standard is detected by: (i) generating a precursor ion of $PGD_2$-$d_9$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$-$d_9$ of the internal standard.

B.12. The system of any one of the previous and/or subsequent embodiments, wherein the precursor ion for $PGD_2$-$d_9$ has a mass/charge ratio (m/z) of about 360.4 and the one or more fragment ions for quantitation comprise a fragment ion with a m/z of about 232.9.

B.13. The system of any one of the previous and/or subsequent embodiments, further comprising adding a second stable isotope labeled $PGD_2$ to the sample as an internal standard, wherein the second isotope is $PGD_2$-$d_4$, and wherein the precursor ion $PGD_2$-$d_4$ has a mass/charge ratio (m/z) of about 355.4 and the one or more fragment ions for quantitation comprise a fragment ion with a m/z of about 275.300, 237.300, 193.2, or 255.5.

B.14. The system of any one of the previous and/or subsequent embodiments, wherein the tandem mass spectrometry detection of $PGD_2$ is performed in selected reaction monitoring mode (SRM).

B.15. The system of any one of the previous and/or subsequent embodiments, wherein the ESI is performed in negative ion mode.

B.16. The system of any one of the previous and/or subsequent embodiments, further comprising a station for dilution of the biological sample.

B.17. The system of any one of the previous and/or subsequent embodiments, comprising detection of $PGD_2$ over a range of from 1.0 pg/mL to 1,000 pg/mL.

C.1. A computer-program product tangibly embodied in a non-transitory machine-readable storage medium, including instructions configured to cause one or more computers to perform actions to measure the presence or amount of $PGD_2$ in a biological sample comprising at least one of the following steps: (a) obtaining a biological sample from a subject; (b) optionally adding a stable isotope-labeled $PGD_2$ to the sample as an internal standard; (c) performing liquid chromatography; and (d) measuring $PGD_2$ by tandem mass spectrometry.

C.2. The computer-program product of any of the previous or subsequent embodiments, wherein the biological sample is a urine or serum.

C.3. The computer-program product of any one of the previous and/or subsequent embodiments, wherein the tandem mass spectrometry comprises the steps of: (i) generating a precursor ion of $PGD_2$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$ in the biological sample.

C.4. The computer-program product of any one of the previous and/or subsequent embodiments, wherein the liquid chromatography comprises high turbulence liquid chromatography (HTLC).

C.5. The computer-program product of any one of the previous and/or subsequent embodiments, wherein the actions to measure the presence or amount of $PGD_2$ in a biological sample further comprises at least one additional purification step.

C.6. The computer-program product of any one of the previous and/or subsequent embodiments, wherein the additional purification step is SPE.

C.7. The computer-program product of any one of the previous and/or subsequent embodiments, wherein the precursor ions are formed using an electrospray ionization.

C.8. The computer-program product of any one of the previous and/or subsequent embodiments, further comprising determining a back-calculated amount of $PGD_2$ in the biological sample by spiking known amounts of each purified $PGD_2$ into charcoal stripped urine or serum to generate calibration curves.

C.9. The computer-program product of any one of the previous and/or subsequent embodiments, wherein the internal standard is detected by: (i) generating a precursor ion of $PGD_2$-$d_9$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$-$d_9$ of the internal standard.

C.10. The computer-program product of any one of the previous and/or subsequent embodiments, wherein the $PDG_2$ precursor ion has a mass/charge ratio (m/z) of about 351.3 and the one or more fragment ions for quantitation comprise a fragment ion with a m/z of about 233.1.

C.11. The computer-program product of any one of the previous and/or subsequent embodiments, wherein the internal standard is $PGD_2$-$d_9$.

C.12. The computer-program product of any one of the previous and/or subsequent embodiments, wherein the precursor ion has a mass/charge ratio (m/z) of about 360.4 and the one or more fragment ions for quantitation comprise a fragment ion with a m/z of about 232.9.

C.13. The computer-program product of any one of the previous and/or subsequent embodiments, further comprising adding a second stable isotope labeled $PGD_2$ to the sample as an internal standard.

C.14. The computer-program product of any one of the previous and/or subsequent embodiments, wherein the tandem mass spectrometry detection of $PGD_2$ is performed in selected reaction monitoring mode (SRM).

C.15. The computer-program product of any one of the previous and/or subsequent embodiments, wherein the ESI is performed in negative ion mode.

C.16. The computer-program product of any one of the previous and/or subsequent embodiments, further comprising dilution of the biological sample.

C.17. The computer-program product of any one of the previous and/or subsequent embodiments, comprising detection of $PGD_2$ over a range of from 1.0 pg/mL to 1,000 pg/mL.

That which is claimed:

1. A method for determining the presence or amount of $PGD_2$ in a biological sample by tandem mass spectrometry, comprising:
   (a) obtaining a sample from a subject;
   (b) adding a stable isotope labeled $PGD_2$ to the sample as an internal standard;
   (c) performing liquid chromatography to purify the sample; and
   (d) measuring the $PGD_2$ by tandem mass spectrometry.

2. The method of claim 1, wherein the biological sample is a urine or serum.

3. The method of claim 1, wherein the tandem mass spectrometry comprises the steps of: (i) generating a precursor ion of $PGD_2$; (ii) generating at least one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$ in the biological sample.

4. The method of claim 1, wherein the liquid chromatography comprises high turbulence liquid chromatography (HTLC).

5. The method of claim 1, further comprising at least one additional purification step.

6. The method of claim 5, wherein the additional purification step is solid phase extraction (SPE).

7. The method of claim 3, wherein the precursor ions are formed using an electrospray ionization (ESI).

8. The method of claim 1, further comprising determining a back-calculated amount of $PGD_2$ in the biological sample by spiking known amounts of each purified $PGD_2$ into charcoal stripped urine or serum to generate calibration curves.

9. The method of claim 3, wherein the precursor ion has a mass/charge ratio (m/z) of about 351.3 and the one or more fragment ions for quantitation comprise a fragment ion with a m/z of about 233.1.

10. The method of claim 1, wherein the internal standard is $PGD_2$-$d_9$.

11. The method of claim 10, wherein the internal standard is detected by: (i) generating a precursor ion of $PGD_2$-$d_9$; (ii) generating at least one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$-$d_9$ of the internal standard.

12. The method of claim 11, wherein the precursor ion has a mass/charge ratio (m/z) of about 360.4 and the one or more fragment ions for quantitation comprise a fragment ion with a m/z of about 232.9.

13. The method of claim 1, further comprising adding a second stable isotope labeled $PGD_2$ to the sample as an internal standard.

14. The method of claim 1, wherein the measuring of $PGD_2$ by tandem mass spectrometry is performed in selected reaction monitoring mode (SRM).

15. The method of claim 7, wherein the ESI is performed in negative ion mode.

16. The method of claim 1, further comprising dilution of the biological sample.

17. The method of claim 1, comprising measuring the $PGD_2$ over a range of from 1.0 pg/mL to 1,000 pg/mL.

18. A system for determining the presence or amount of at least one biomarker of interest in a biological sample, the system comprising:
   station for providing a test sample suspected of containing $PGD_2$;
   a station for partially purifying $PGD_2$ from other components in the sample;
   a station for chromatographically separating $PGD_2$ from other components in the sample; and
   a station for analyzing the chromatographically separated $PGD_2$ by mass spectrometry to determine the presence or amount of $PGD_2$ in the biological sample.

19. A computer-program product tangibly embodied in a non-transitory machine-readable storage medium, including instructions configured to cause one or more computers to perform actions to measure the presence or amount of $PGD_2$ in a biological sample comprising at least one of the following steps:
   (a) obtaining a biological sample from a subject;
   (b) adding a stable isotope-labeled $PGD_2$ to the sample as an internal standard;
   (c) performing liquid chromatography; and
   (d) measuring $PGD_2$ by tandem mass spectrometry.

20. The computer-program product of claim 19, wherein the tandem mass spectrometry comprises the steps of: (i) generating a precursor ion of $PGD_2$; (ii) generating one or more fragment ions of the precursor ion; and (iii) detecting the presence or amount of the precursor ion generated in step (i) and/or the at least one or more fragment ions generated in step (ii), or both, and relating the detected ions to the presence or amount of the $PGD_2$ in the biological sample.

21. The computer-program product of claim 20, wherein the precursor ion has a mass/charge ratio (m/z) of about 351.3 and the one or more fragment ions for quantitation comprise a fragment ion with a m/z of about 233.1.

* * * * *